US006214817B1

(12) United States Patent
Riley et al.

(10) Patent No.: US 6,214,817 B1
(45) Date of Patent: Apr. 10, 2001

(54) SUBSTITUTED PYRIDINO PENTAAZAMACROCYLE COMPLEXES HAVING SUPEROXIDE DISMUTASE ACTIVITY

(75) Inventors: Dennis P. Riley, Chesterfield; William L. Neumann, Ballwin; Susan L. Henke; Patrick Lennon, both of Webster Groves; Karl W. Aston, Pacific; Daniela Salvemini, Chesterfield; James A. Sikorski, Des Peres; Yvette M. Fobian, Labadie, all of MO (US); Margaret Lanahan Grapperhaus, Troy; Carrie L. Kusturin, Edwardsville, both of IL (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/398,120

(22) Filed: Sep. 16, 1999

Related U.S. Application Data

(63) Continuation-in-part of application No. 09/057,831, filed on Apr. 9, 1998.
(60) Provisional application No. 60/050,402, filed on Jun. 20, 1997.

(51) Int. Cl.$^7$ ...................... C07D 487/22; A61K 31/675; A61K 47/16
(52) U.S. Cl. .......................... 514/186; 514/183; 514/184; 540/473; 540/474
(58) Field of Search ..................... 540/473, 474; 514/183, 184, 186

(56) References Cited

U.S. PATENT DOCUMENTS

| | | | |
|---|---|---|---|
| 3,930,867 | 1/1976 | Bigelow | 96/107 |
| 4,001,212 | 1/1977 | Richman | 260/239 |
| 4,702,998 | 10/1987 | Tanaka et al. | 430/430 |
| 4,968,616 | 11/1990 | Inoue et al. | 435/188 |
| 5,096,724 | 3/1992 | Zenner et al. | 426/124 |
| 5,322,681 | 6/1994 | Klaveness | 424/9 |
| 5,403,834 | 4/1995 | Malfroy-Camine et al. | 514/185 |
| 5,556,968 | 9/1996 | Carvalho et al. | 540/460 |
| 5,610,293 | 3/1997 | Riley et al. | 540/474 |
| 5,637,578 | 6/1997 | Riley et al. | 514/186 |
| 5,696,109 | 12/1997 | Malfroy-Camine et al. | 514/185 |
| 5,827,880 | 10/1998 | Malfroy-Camine et al. | 514/492 |
| 5,834,509 | 11/1998 | Malfroy-Camine et al. | 514/492 |
| 5,874,421 | 2/1999 | Riley et al. | 514/161 |

FOREIGN PATENT DOCUMENTS

| | | |
|---|---|---|
| 108806A | 6/1994 | (CN) . |
| 0 679155 B1 | 8/1997 | (EP) . |
| 0 598753 B1 | 3/1998 | (EP) . |
| WO 82/04252 | 12/1982 | (WO) . |
| WO 91/10645 | 7/1991 | (WO) . |
| WO 92/08707 | 5/1992 | (WO) . |
| WO 93/11800 | 6/1993 | (WO) . |
| WO 93/14093 | 7/1993 | (WO) . |
| WO 95/28968 | 11/1995 | (WO) . |
| WO 96/39396 | 12/1996 | (WO) . |
| WO 96/39409 | 12/1996 | (WO) . |
| WO 96/40658 | 12/1996 | (WO) . |
| WO 98/58636 | 12/1998 | (WO) . |

OTHER PUBLICATIONS

M. Dale Alexander, et al., "Managanese(II) Complexes of a Macrocyclic Ligand," 1970, (Inorganic Nuclear Chemistry Letters, vol. 6) pp. 445–448.

Jack E. Richman, et al., "Nitrogen Analogs of Crown Ethers," Apr. 3, 1974, (Journal of the American Chemical Society. vol. 96:7).

Stephen F. Brady, et al., "Practical Synthesis of Cyclic Peptides, with an Example of Dependence of Cyclization Yield Upon Linear Sequence," 1979, (Journal of Organic Chemistry, vol. 44, No. 18) pp. 3101–3105.

Eiichi Kimura, et al., "Superoxide Dismutase Activity of Macrocylic Polyamine Complexes," 1981 (Biochimica et Biophysica Acta, vol. 678) pp. 172–179.

Eiichi Kimura, et al., "Further Studies on Superoxide Dismutase Activities of Macrocyclic Polyamine Complexes of Copper(II)," 1983, (Biochemica et Biophysica Acta, vol. 745) pp. 37–43.

Eiichi Kimura, et al., "Superoxide Dismutase Activity of Macrocyclic Polyamine Complexes," 1982, (Chemical Abstracts, vol. 96) p. 270.

R. J. Gryglewski, et al., "Superoxide Anion is Involved in the Breakdown of Endothelium–Derived Vascular Relaxing Factor," Apr. 1986, (Nature, vol. 320) pp. 454–456.

Joe V. Bannister, et al., "Aspects of the Structure, Function, and Applications of Superoxide Dismutase," 1987, (CRC Critical Reviews in Biochemistry, vol. 22, Issue 2) pp. 111–180.

James E. Newton, et al., "Synthesis and Characterization of the Mn(II) Complex of [15]aneN$_5$," 1988, (J. Coord. Chem, vol. 19) pp. 265–277.

Joachim Cremer, et al., "Oxygen Free Radical Scavengers to Prevent Pulmonary Reperfusion Injury After Heart–Lung Transplantation," Jul./Aug. 1989, (The Journal of Heart Transplantation, vol. 8, No. 4) pp. 330–336.

(List continued on next page.)

Primary Examiner—Richard L. Raymond
Assistant Examiner—Pavanaram K Sripada
(74) Attorney, Agent, or Firm—Senniger, Powers, Leavitt & Roedel

(57) ABSTRACT

The present invention relates to compounds which are effective as catalysts for dismutating superoxide and, more particularly, the manganese or iron complexes of substituted, unsaturated heterocyclic pentaazacyclopentadecane ligands which catalytically dismutate superoxide.

31 Claims, 8 Drawing Sheets

OTHER PUBLICATIONS

Figure 1:
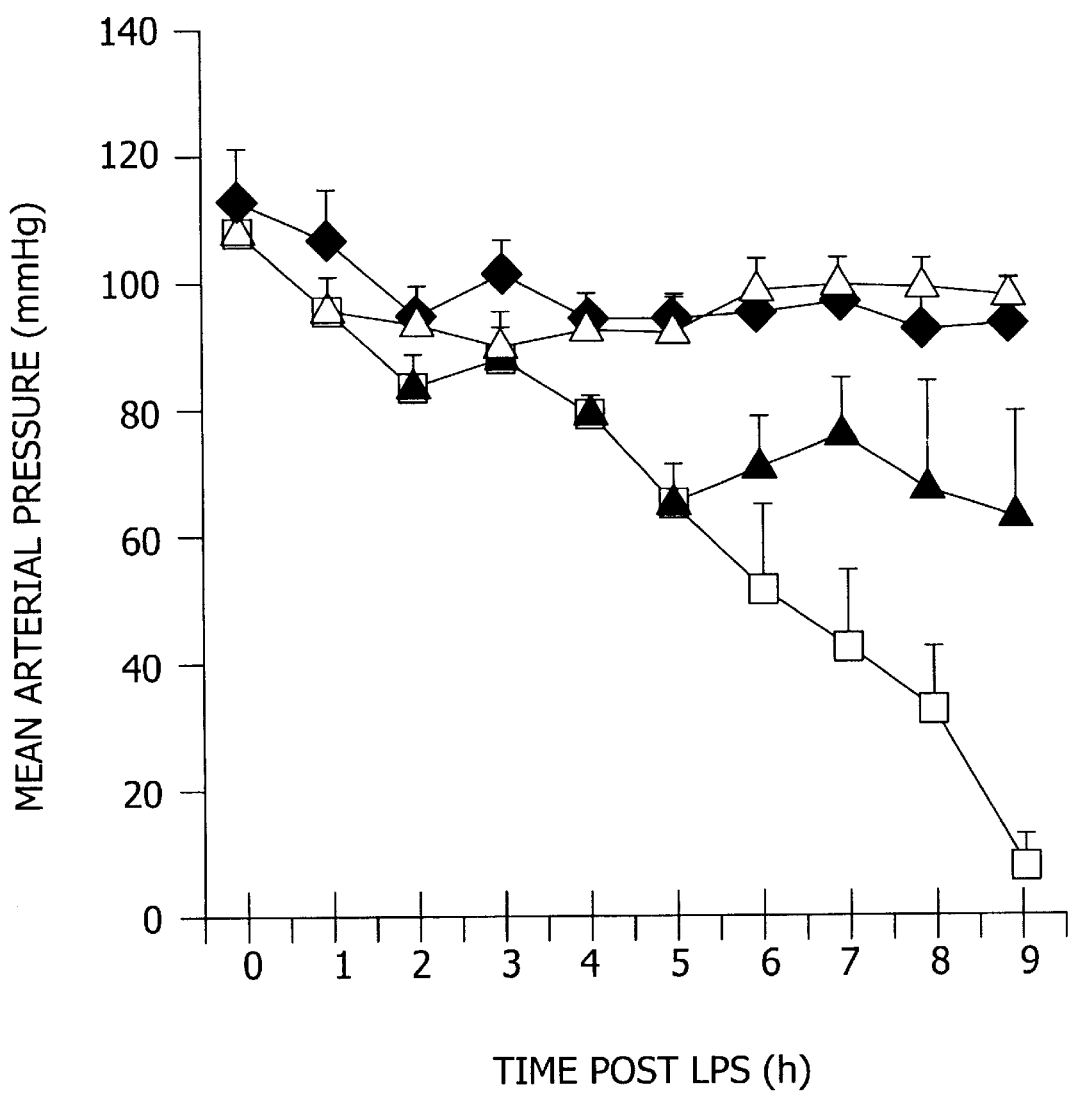

Jerald S. Bradshaw, et al., "A Simple Crab–Like Cyclization Procedure to Prepare Polyaza–Crowns and Cyclams with One or Two Unsubstituted Macroring Nitrogen Atoms or with a Hydroxy Group," Sep./Oct. 1989, (J. Heterocyclic Chem., vol. 26) pp. 1431–1435.

Leonard F. Lindoy, "The Chemistry of Macrocyclic Ligand Complexes," 1989 (The Press Syndicate of the University of Cambridge) pp. 17, and 40–43.

R. Ferrari, et al., "Superoxide Dismutase: Possible Therapeutic Use in Cardiovascular Disease," 1989, (Pharmalogical Research, vol. 21, Supplement 2) pp. 57–65.

Krzysztof E. Karkowiak, et al., "Preparation of Triaza–, Tetraaza– and Peraza–Crown Compounds Containing Aminoalkyl Side Groups or Unsubstituted Ring Nitrogen Atoms," 1990, (J. Org. Chem., vol. 55, No. 10) pp. 3364–3368.

Dennis P. Riley, et al., "Stopped–Flow Kinetic Analysis for Monitoring Superoxide Decay in Aqueous Systems," 1991, (Analytical Biochemistry, vol. 196) pp. 344–349.

Randy H. Weiss, et al., "Catalytic Efficacies of Agents that Dismutate Superoxide," 1991, (J. Cell. Biochem., Supplement 15C) p. 216.

D. J. Fretland, et al., "Superoxide Dismutase(SOD) Modulates Acetic Acid–Induced Colitis in Rodents," 1991 (Gastroenterology, vol. 100) p. A581.

Susan T. Shuff, et al., "Stable Superoxide Dismutase (SOD-)–Mimetic Ternary Human Serum Albumin–Cu(II)(3,5–Diisopropylsalicylate)$_2$/(3,5–Disopropylsalicylate)$_4$Complexes in Tissue Distribution of the Binary Complex," 1992, (Biochemical Pharmacology, vol. 43, No. 7) pp. 1601–1612.

Rina Varsano, et al., "Superoxide Dismutase Activity in Morphine– and Meperidine–Addicted Mice and Their Response to Paraquat Poisoning," 1992, (Fresenius Envir. Bull 1, Supplement) pp. S54–S59.

Patrick J. Lennon, et al., "New Conformationally Constrained Polyaza Macrocycles Prepared via the Bis(chloracetamide) Method," 1994, (Tetrahedron Letters, vol. 35, No. 6) pp. 853–856.

Karl W. Aston, et al., "Asymmetric Synthesis of Highly Functionalized Polyazamacrocycles via Reduction of Cyclic Peptide Precursors," 1994, (Tetrahedron Letters, vol. 35, No. 22) pp. 3687–3690.

Y. Lin, et al., "Use of Superoxide Dismutase (SOD) in Patients with Temporomandibular Joint Dysfunction—a Preliminary Study," 1994, (International Journal of Oral Maxillofacial Surgery, vol. 23) pp. 428–429.

Medora M. Hardy, et al., "Superoxide Dismutase Mimetics Inhibit Neutrophil–Mediated Human Aortic Endothelial Cell Injury in vitro*," 1994, (The Journal of Biological Chemistry, vol. 269, No. 28) pp. 18535–18540.

Gregory B. Bulkley, "Reactive Oxygen Metabolites and Reperfusion Injury: Aberrant Triggering of Reticuloendothelial Function," Oct. 1994, (The Lancet, vol. 344) pp. 934–936.

Gregory I. Elmer, et al., "Transgenic Superoxide Dismutase Mice Differ in Opioid–Induced Analgesia," 1995, European Journal of Pharmacology, vol. 283) pp. 227–232.

N. Goldstein, et al., "Exogenous Gaseous Superoxide Potentiates the Antinociceptve Effect of Opioid Analgesic Agents," 1996, (Inflamm. Res., vol. 45) pp. 473–478.

Michael Tal, "A Novel Antioxidant Alleviates Heat Hyperalgesia in Rats with an Experimental Painful Peripheral Neuropathy," May 1996, (NeuroReport, vol. 7, No. 8) pp. 1382–1384.

B. M. Babior, "Superoxide: a Two–Edged Sword," 1997, (Brazilian Journal of Medical and Biological Research, vol. 30), pp. 141–155.

SUBSTITUTED PYRIDINO PENTAAZAMACROCYLE COMPLEXES HAVING SUPEROXIDE DISMUTASE ACTIVITY

This application is a continuation in part of U.S. application Ser. No. 09/057,831, filed Apr. 9, 1998, pending, which claims the benefit of Provisional Application No. 60/050,402, filed Jun. 20, 1997, now abandoned.

BACKGROUND OF THE INVENTION

1. Field of the Invention

The present invention relates to compounds which are effective as catalysts for dismutating superoxide and, more particularly, the manganese or iron complexes of substituted, unsaturated heterocyclic pentaazacyclopentadecane ligands which catalytically dismutate superoxide.

2. Related Art

The enzyme superoxide dismutase catalyzes the conversion of superoxide into oxygen and hydrogen peroxide according to equation (1) (hereinafter referred to as dismutation).

$$2O_2^- + 2H^+ \rightarrow O_2 + H_2O_2 \tag{1}$$

Reactive oxygen metabolites derived from superoxide have been demonstrated to contribute to the tissue pathology in a number of inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Simic, M. G., et al, Oxygen Radicals in Biology and Medicine, Basic Life Sciences, Vol. 49, Plenum Press, New York and London, 1988; Weiss, J. Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V. et al, Crit. Rev. Biochem., 22, 111 (1987).

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of hypertension, vasospasm, thrombosis and atherosclerosis. See, for example, Gryglewski, R. J. et al., "Superoxide Anion is Involved in the Breakdown of Endothelium-derived Vascular Relaxing Factor", Nature, Vol. 320, pp. 454–56 (1986) and Palmer, R. M. J. et al., "Nitric Oxide Release Accounts for the Biological Activity of Endothelium Derived Relaxing Factor", Nature, Vol. 327, pp. 523–26 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity, short half-lives in vivo, immunogenicity of nonhuman derived enzymes, and poor tissue distribution.

In an effort to overcome the problems associated with superoxide dismutase enzymes, several investigations have been made into the design of non-proteinaceous catalysts for the dismutation of superoxide, and their use in various superoxide-related ailments. One group of catalysts which has been shown to be nearly as effective catalysts as the native superoxide dismutase enzymes are the manganese and iron complexes of pentaazacyclopentadecane ligands, described in U.S. Pat. Nos. 5,610,293, 5,637,578, and 5,874,421. These ligands are described as a pentaazacyclopentadecane macrocycle with various substituents on the carbons of the macrocycle, or with cyclic or heterocyclic structures attached to the carbons of the macrocycle. These compounds have been shown to possess catalytic superoxide dismutating activity as well as anti-inflammatory activity and to prevent oxidative damage. In addition, these compounds have been shown to possess analgesic activity in the rat-paw carrageenan hyperalgesia model, U.S. application Ser. No. 09/057,831. Two such described analgesic SOD mimic compounds are Compound A and Compound B:

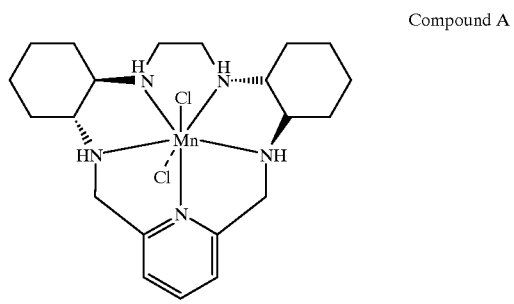

Compound A

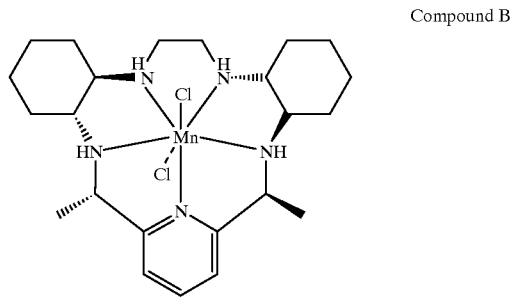

Compound B

SUMMARY OF THE INVENTION

Applicants have found that, surprisingly, the addition of substituents to an unsaturated nitrogen-containing heterocyclic moiety on the pentaazacyclopentadecane macrocycle of the above complexes can drastically alter both the superoxide dismutase catalytic activity and increase the efficacy of these complexes as pharmaceutical agents. Applicants have found that compounds of the present invention comprising substituted, unsaturated, nitrogen-containing heterocyclic moieties unexpectedly exhibit a marked increase in potency for the prevention or reversal of opioid tolerance as compared to the previously disclosed complexes with unsubstituted nitrogen-containing heterocyclic moieties. In addition, these substituted, unsaturated, nitrogen-containing heterocyclic compounds are up to ten times more potent as pharmaceutical agents for anti-inflammatory and analgesic compositions and are as good as, or often better than, the parent unsubstituted compounds in applications such as the treatment of endotoxin-induced refractory hypotension. Thus, the compounds of the present invention demonstrate unanticipated improvements in characteristics important for pharmaceuticals over the previously described pentaazacyclopentadecane complexes with unsubstituted nitrogen-containing heterocyclic moieties.

The present invention is directed to low molecular weight catalysts for the dismutation of superoxide radicals (SOD mimics) useful as therapeutic agents for inflammatory disease states and disorders in which superoxide anions are implicated. The SOD mimics of the present invention are manganese or iron complexes of nitrogen-containing fifteen-membered macrocyclic ligands which comprise a substituted, unsaturated, nitrogen-containing heterocyclic moiety, most preferably those with cyclohexyl, hydroxyl alkyl thio, alkyl (2-thioacetic acid) ester, benzyloxy, methoxyarylthio, alkoxycarbonylarylthio, and aryl (2-thioacetic acid) ester substituents. Preferably, the nitrogen-containing heterocyclic moiety is aromatic, more preferably a pyridino moiety.

The present invention is also directed to the pentaazacyclopentadecane macrocycles which comprise a substituted, unsaturated, nitrogen-containing heterocyclic moiety which are precursor ligands of these complexes.

The present invention is also directed to methods of making the above SOD mimics, specifically, novel methods of modifying the substituents on the heterocyclic moiety after chelation with the transition metal ion.

The present invention is also directed towards pharmaceutical compositions comprising the SOD mimics of the present invention in amounts sufficient for the treatment or prevention of disease states or disorders.

In addition, the present invention is directed to methods of using these catalysts to treat various disease states and disorders in which superoxide anions are implicated.

Other objects and features will be in part apparent and in part pointed out hereinafter.

BRIEF DESCRIPTION OF DRAWINGS AND DEFINITIONS

Drawings

FIG. 1: A chart of mean arterial pressure data from endotoxemic rats, Example 16. ♦ Group received saline (control); □ Group received LPS only; Δ Group received LPS and an infusion of 0.25 mg/kg/hr of Compound A at 1 hour; ▲ Group received LPS and an infusion of 0.25 mg/kg/hr of Compound A at 5 hours.

Figure 2:
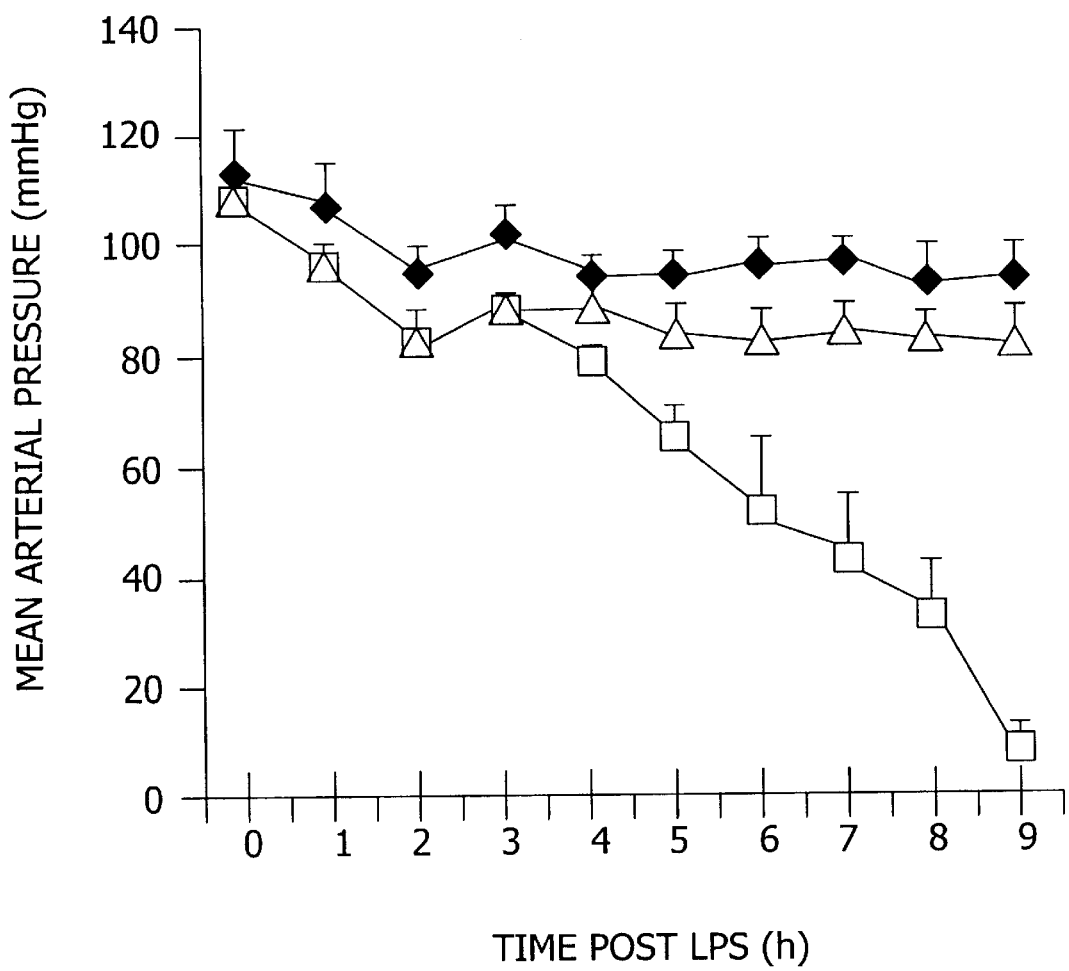

FIG. 2: A chart of mean arterial pressure data from endotoxemic rats, Example 16. ♦ Group received saline (control); □ Group received LPS only; Δ Group received LPS and an infusion of 0.075 mg/kg/hr of Compound 25 at 3 hours.

Figure 3:
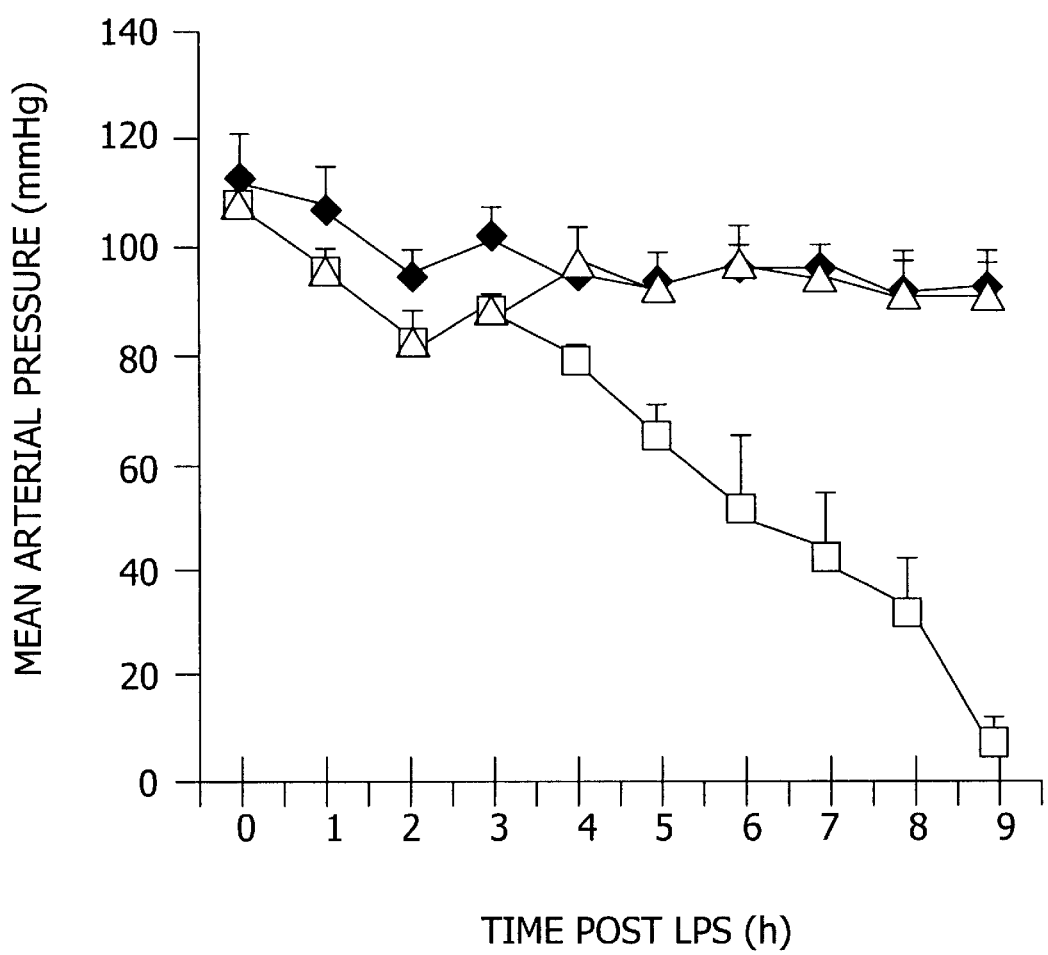

FIG. 3: A chart of mean arterial pressure data from endotoxemic rats, Example 16. ♦ Group received saline (control); □ Group received LPS only; Δ Group received LPS and an infusion of 0.075 mg/kg/hr of Compound 31 at 3 hours.

Figure 4:
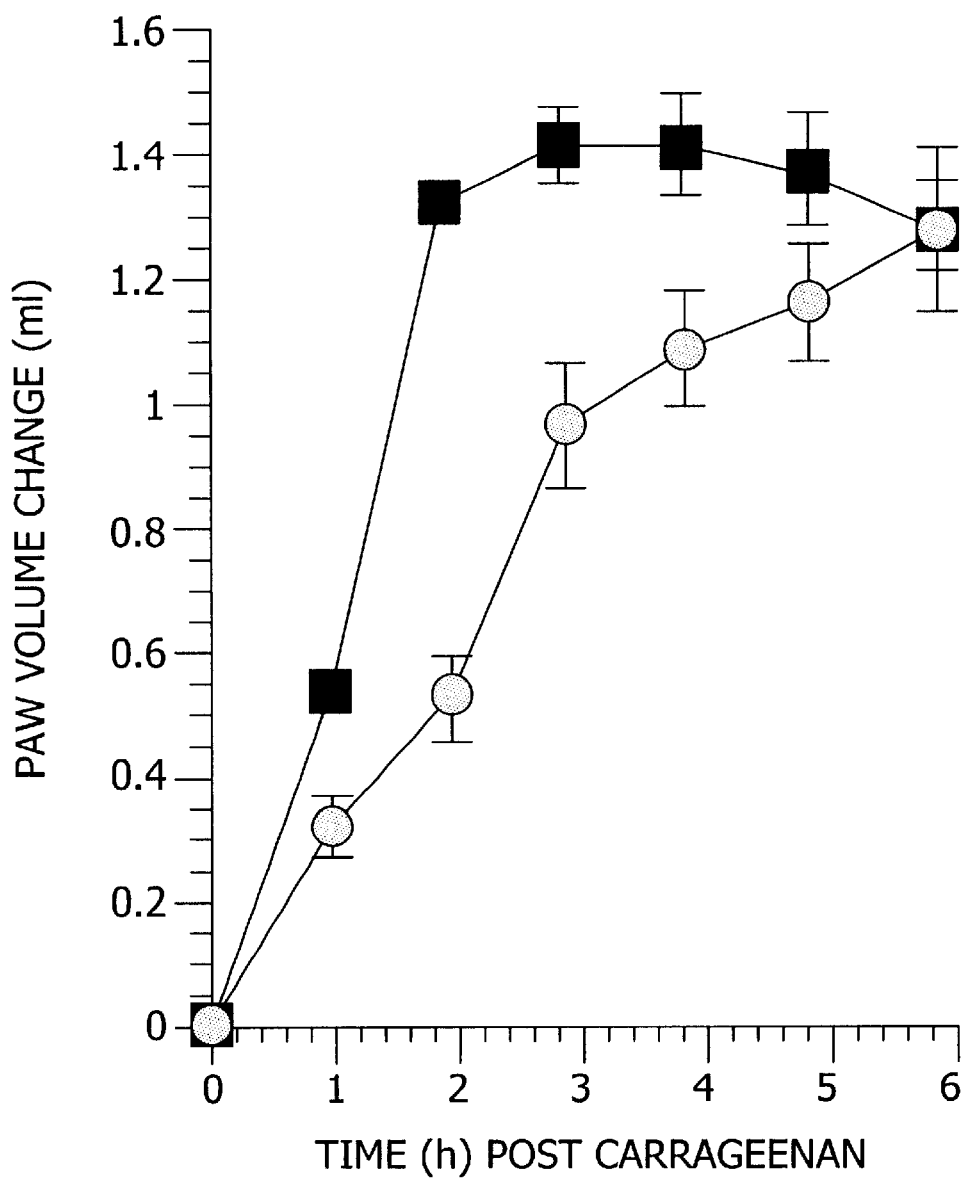

FIG. 4: A chart of paw volume change in the rat paw carrageenan model, Example 14. ■ Group received carrageenan injection only; ● Group received an infusion of 6 mg/kg/hr of Compound A 15 minutes before carrageenan injection.

Figure 5:
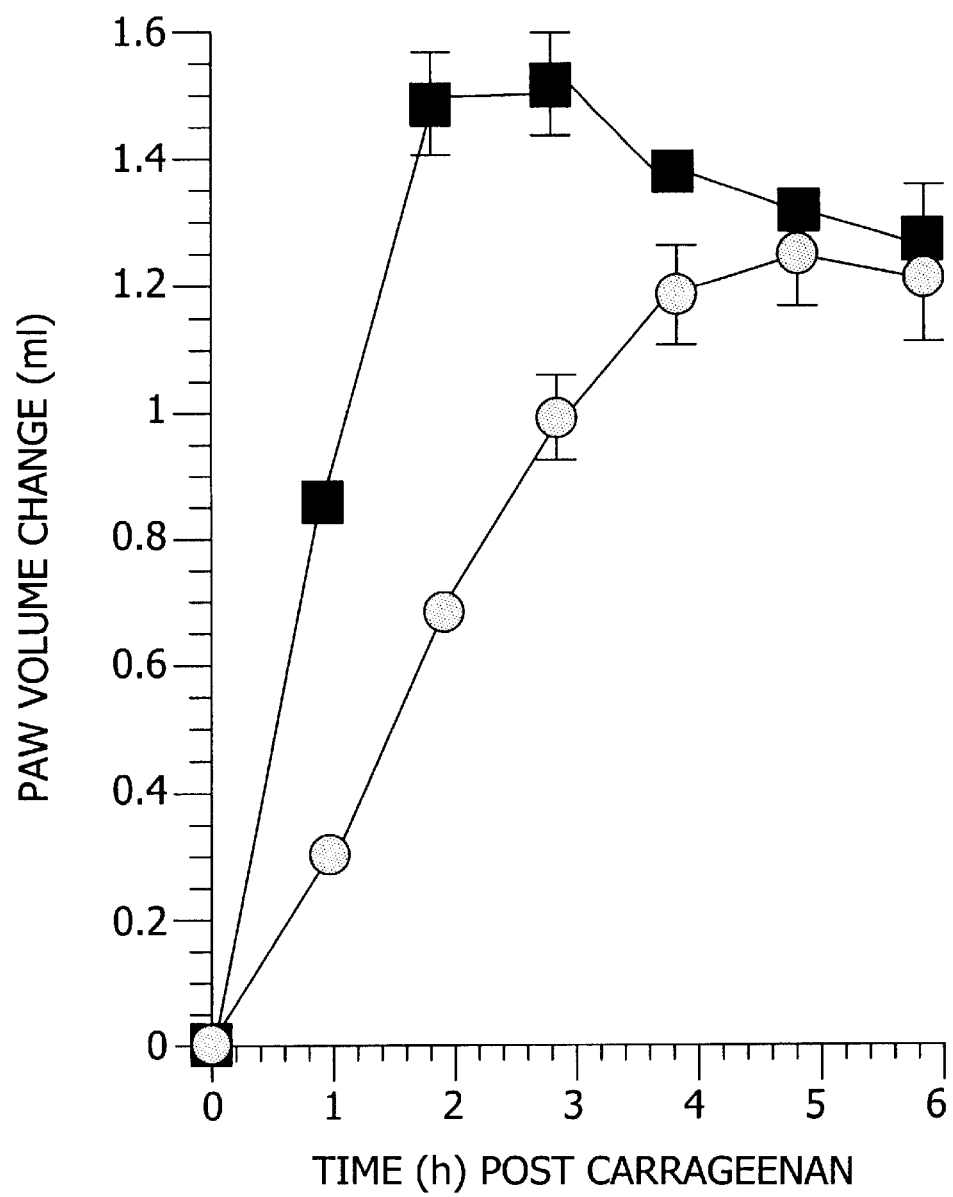

FIG. 5: A chart of paw volume change in the rat paw carrageenan model, Example 14. ■ Group received carrageenan injection only; ● Group received an infusion of 10 mg/kg/hr of Compound 13 15 minutes before carrageenan injection.

Figure 6:
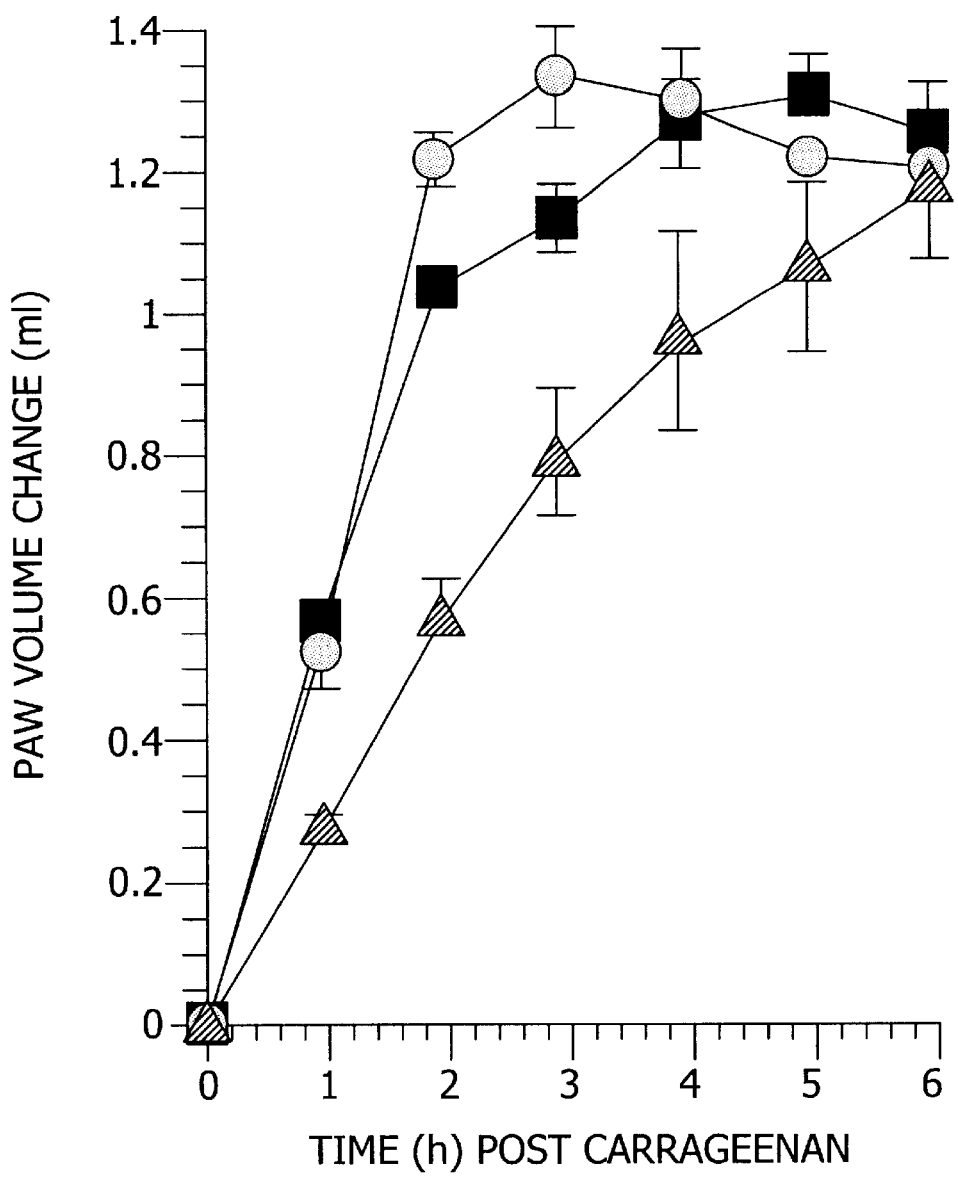

FIG. 6: A chart of paw volume change in the rat paw carrageenan model, Example 14. ■ Group received carrageenan injection only; ● Group received an infusion of 1 mg/kg/hr of Compound 14 15 minutes before carrageenan injection, ▲ Group received an infusion of 10 mg/kg/hr of Compound 14 15 minutes before carrageenan injection.

Figure 7:
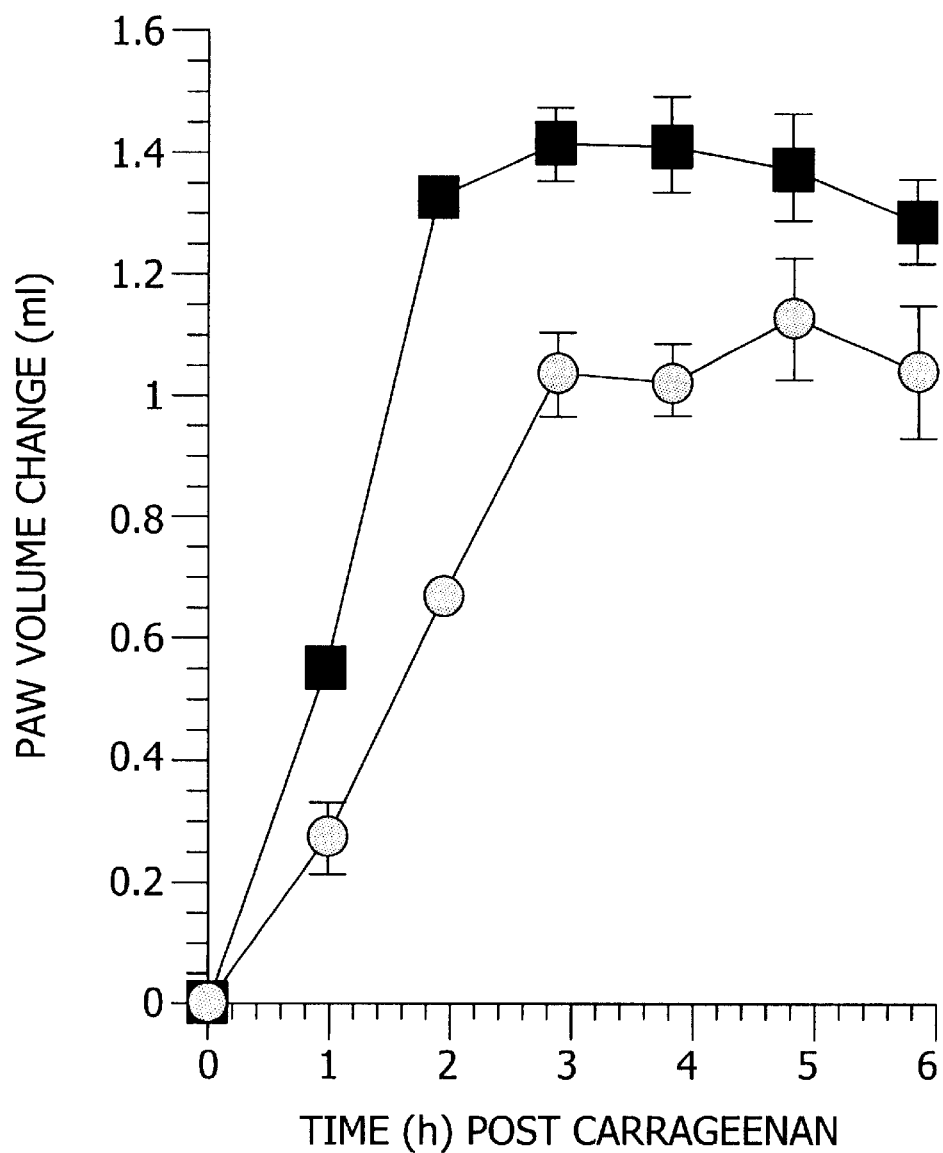

FIG. 7: A chart of paw volume change in the rat paw carrageenan model, Example 14. ■ Group received carrageenan injection only; ● Group received an infusion of 10 mg/kg/hr of Compound 25 15 minutes before carrageenan injection.

Figure 8:
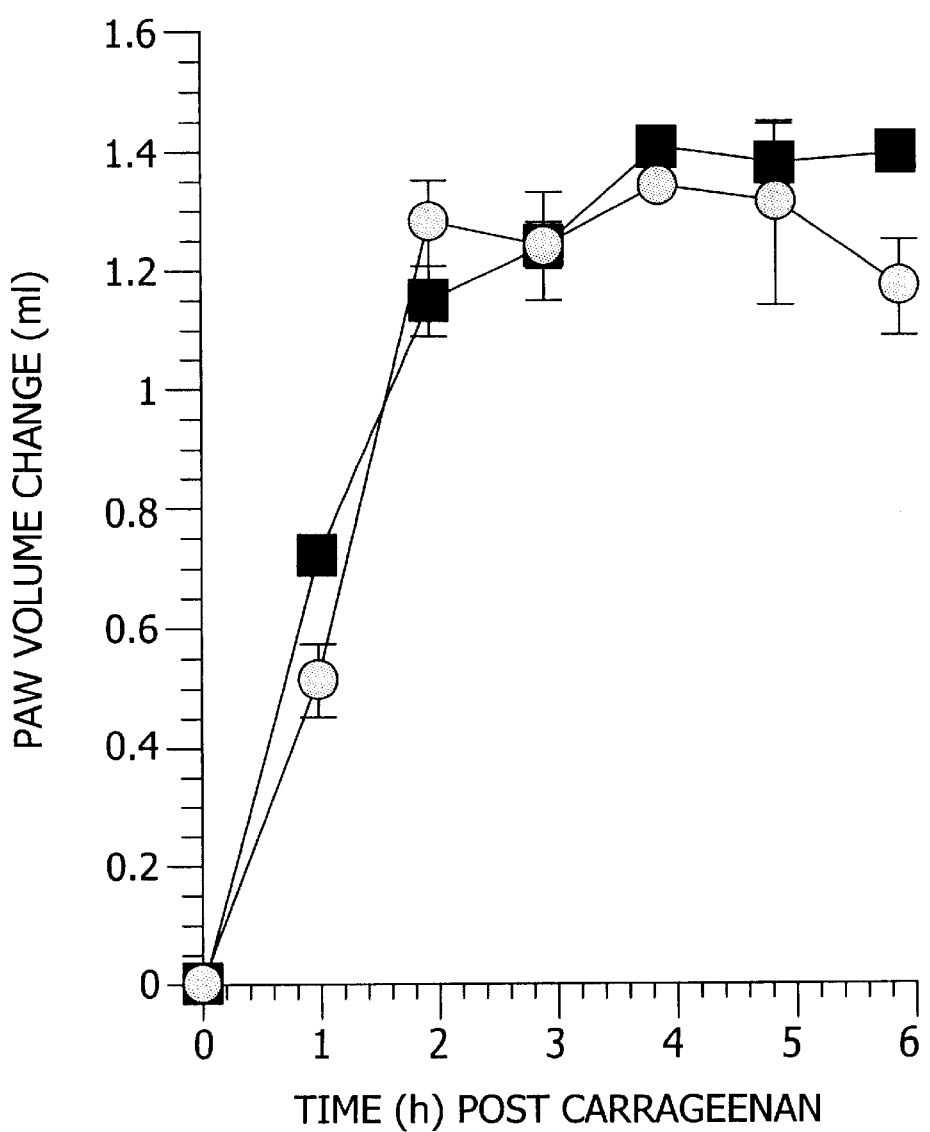

FIG. 8: A chart of paw volume change in the rat paw carrageenan model, Example 14. ■ Group received carrageenan injection only; ● Group received an infusion of 10 mg/kg/hr of Compound 31 15 minutes before carrageenan injection.

DEFINITIONS

As utilized herein, the term "SOD mimic" means a low-molecular-weight catalyst for the conversion of superoxide anions into hydrogen peroxide and molecular oxygen. These catalysts consist of an organic ligand having a pentaazacyclopentadecane portion and a chelated transition metal ion, preferably manganese or iron. The term may include catalysts containing short-chain polypeptides (under 15 amino acids), or macrocyclic structures derived from amino acids, as the organic ligand. The term explicitly excludes a superoxide dismutase enzyme obtained from any natural sources.

The term "precursor ligand" means the organic ligand of a SOD mimic without the chelated transition metal cation and charge neutralizing anions.

The term "substituted" means that the described moiety has one or more substituents comprising at least 1 carbon or heteroatom, and further comprising 0 to 22 carbon atoms, more preferably from 1 to 15 carbon atoms, and comprising 0 to 22, more preferably from 0 to 15, heteroatoms selected from the group consisting of: O, S, N, P, Si, B, F, Cl, Br, or I. These atoms may be arranged in a number of configurations, creating substituent groups which are unsaturated, saturated, or aromatic. Examples of such substituents include branched or unbranched alkyl, alkenyl, or alkynyl, cyclic, hetercyclic, aryl, heteraryl, allyl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, amide, nitrile, halo, thiol, sulfoxide, sulfone, sulfonic acid, sulfide, disulfide, phosphonic acid, phosphinic acid, acrylic acid, sulphonamides, amino acids, peptides, proteins, carbohydrates, nucleic acids, fatty acids, lipids, nitro, hydroxylamines, hydroxamic acids, thiocarbonyls, thiocarbonyls, borates, boranes, boraza, silyl, silaza, siloxy, and combinations thereof.

The term "alkyl", alone or in combination, means a straight-chain or branched-chain alkyl radical containing from 1 to about 22 carbon atoms, prafarably from about 1 to about 18 carbon atoms, and most preferably from about 1 to about 12 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4- hexadienyl, 5,8,11,14-eicosatetraenyl, and 9,12,15-octadecatrienyl.

The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

The term "cycloalkyl", alone or in combination means a cycloalkyl radica containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and perhydronaphthyl.

The term "cycloalkylalkyl" means an alkyl radical as defined above which is substituted by a cycloalkyl radical as defined above. Examples of cycloalkylalkyl radicals include, but are not limited to, cyclohexylmrthyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl.

The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl.

The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-1-yl)hexyl, 1-(1-cyclopenten-1-yl)nonyl and 1-(1-cyclohexen-1-yl)nonyl.

The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl or cycloalkyl radical as defined above in which one hydrogen atom is replaced by an aryl radical as defined above, such as benzyl, 2-phenylethyl, and the like.

The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring.

The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms.

The term "nitrogen containing heterocycle" means ring structures in which 2 carbons and a nitrogen of the ring are also part of the fifteen-membered macrocyclic ligand. The ring 10 structure can contain 2 to 20, preferably 4 to 10, carbon atoms, can be substituted or unsubstituted, partially or fully unsaturated or saturated, and can also contain nitrogen, oxygen and/or sulfur atoms in the portion of the ring which is not also part of the fifteen-membered macrocyclic ligand.

The term "disease states and disorders in which superoxide anions are implicated" means any disease state or disorder in which superoxide anions, or the products of reactions involving superoxide anions (such as peroxynitrate), are known or suspected to be a factor in the progression of the disease state or disorder. Examples of such disease states and disorders are inflammation and ischemic reperfusion injury.

The term "organic acid anion" refers to carboxylic acid anions having from about 1 to about 18 carbon atoms.

The term "halide" means chloride, floride, iodide, or bromide.

As used herein, "R" groups means all of the R groups attached to the carbon atoms of the macrocycle, i.e., R, R', R1, R'1, R2, R'2, R3, R'3, R4, R'4, R5, R'5, R6, R'6, R7, R'7, R8, R'8, R9.

All references cited herein are explicitly incorporated by reference.

Corresponding reference characters indicate corresponding parts throughout the drawings.

DETAILED DESCRIPTION OF THE INVENTION

The present invention is directed to nitrogen-containing fifteen-membered macrocyclic ligands, and their complexes with transition metals, which are described by the formula:

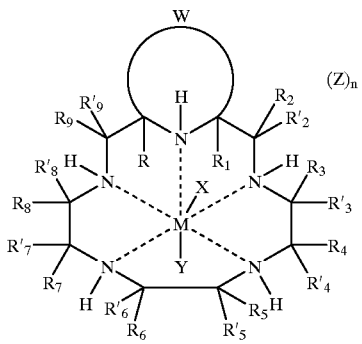

wherein a nitrogen of the macrocycle and the two adjacent carbon atoms to which it is attached independently form a substituted, unsaturated, nitrogen containing heterocycle W having 2 to 20 carbon atoms, more preferably 4 to 10 carbon atoms, which may be an aromatic heterocycle wherein the hydrogen attached to the nitrogen which is both part of the heterocycle and the macrocycle and the R groups attached to the carbon atoms which are both part of the heterocycle and the macrocycle are absent;

and wherein R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently represent hydrogen, or substituted or unsubtituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals;

and, optionally, one or more of $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 2 to 20 carbon atoms, which may be an aromatic heterocycle wherein the hydrogen attached to the nitrogen which is both part of the heterocycle and the macrocycle and the R groups attached to the carbon atoms which are both part of the heterocycle and the macrocycle are absent;

and, optionally, one or more of $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a saturated, partially saturated, or unsaturated cyclic or heterocyclic ring having 3 to 20 carbon atoms;

and, optionally, one of R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula

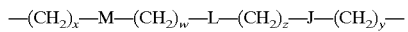

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof; and combinations of any of the above;

wherein M is a cation of a transition metal, preferably manganese or iron;

and wherein X, Y, and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y, and Z may be independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, lactate, gluconate, ascorbate, saccharinate, amino acid, hydroxamic acid, thiotosylate, and anions of ion exchange resins. The preferred ligands from which X, Y and Z are selected include halide, organic acid, nitrate and bicarbonate anions.

Thus, the SOD mimics of the present invention can have any combinations of substituted or unsubstituted R groups, saturated, partially saturated or unsaturated cyclics, ring structures, nitrogen containing heterocycles, or straps as defined above.

Also within the present invention are the unchelated precursor ligands of the complexes described above, which are described by the following formula:

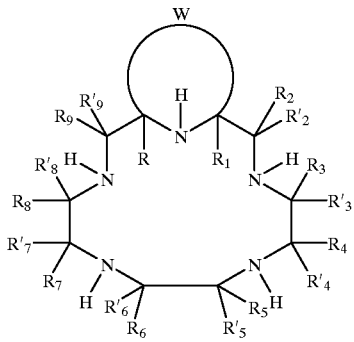

Wherein the "R" groups and W are as defined above.

The "R" groups attached to the carbon atoms of the macrocycle can be in the axial or equatorial position relative to the macrocycle. When the "R" group is other than hydrogen or when two adjacent "R" groups, i.e., on adjacent carbon atoms, together with the carbon atoms to which they are attached form a saturated, partially saturated or unsaturated cyclic or a nitrogen containing heterocycle, or when two R groups on the same carbon atom together with the carbon atom to which they are attached form a saturated, partially saturated or unsaturated ring structure, it is preferred that at least some of the "R" groups are in the equatorial position for reasons of improved activity and stability. This is particularly true when the complex contains more than one "R" group which is not hydrogen.

Preferred compounds of the present invention are those described by the following formula:

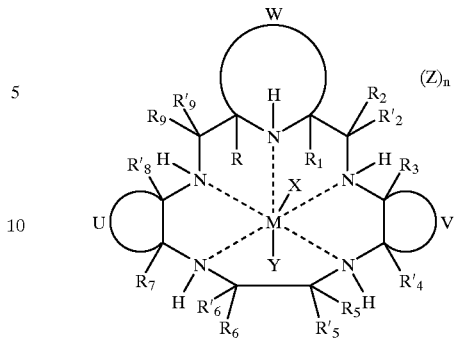

wherein the R groups, W, M, X, Y, and Z are as defined above, and wherein U and V are saturated cyclic structures, containing between 3 and 20, preferably between 4 and 10 carbon atoms and forming a cycloalkyl ring with the carbon atoms to which they are attached. In more preferred embodiments of the invention, U and V are two trans-cyclohexano fused rings. In more preferred embodiments of the invention, W is a substituted pyridine, and R, $R_1$, and the H on the nitrogen of the macrocycle within W are absent. In particularly preferred embodiments of the present invention, W is a substituted pyridine, and U and V are trans-cyclohexano fused rings. Preferred substituents on W are those which increase the potency of the catalyst for pharmaceutical applications. For instance, lipophilic substituents are preferred when the target of the catalyst is a hydrophobic tissue of the patient. In addition to altering the catalytic activity or log P and the concomitant targeting/pharmokinetic effects, applicants have discovered that certain substituents generally increase the potency of the catalyst for use in pharmaceutical compositions. These preferred substituents include cyclohexyl, hydroxyl alkyl thio, alkyl (2-thioacetic acid) esters, benzyloxy, methoxyarylthio, alkoxycarbonylarylthio, and aryl (2-thioacetic acid) esters. Examples of complexes of the invention include, but are not limited to, compounds having the following formulas:

| | TABLE OF COMPOUNDS | | | |
|---|---|---|---|---|
| COMPOUND | | MOL. WT. | $k_{cat}$ pH 7.4 $\times 10^{-7} M^{-1} s^{-1}$ | Log P |
| 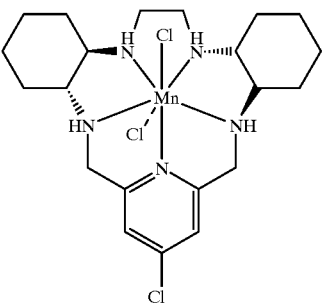 | | 517.83 | 1.18 | 0.46 |

-continued

| TABLE OF COMPOUNDS | | | |
|---|---|---|---|
| COMPOUND | MOL. WT. | $k_{cat}$ pH 7.4 $\times 10^{-7} M^{-1} s^{-1}$ | Log P |
| [structure: Mn complex with methoxy-substituted pyridine] | 512.00 | 1.90 | −0.02 |
| [structure: Mn complex with cyclohexyl-substituted pyridine] | 457.37 | 3.75 | 2.27 |
| [structure: Mn complex with octahydroacridine] | 563.50 | 0.74 | 1.56 |
| [structure: Mn complex with phenyl-substituted octahydroacridine] | 639.61 | 0.29 | 1.94 |

-continued

TABLE OF COMPOUNDS

| COMPOUND | MOL. WT. | $k_{cat}$ pH 7.4 × $10^{-7} M^{-1} s^{-1}$ | Log P |
|---|---|---|---|
| [structure] | 571.55 | 0.80 | 1.48 |
| [structure] | 627.00 | 0.53 | 1.05 |
| [structure] | 584.00 | 2.85 | |
| [structure] | 679.76 | 1.02 | 2.53 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| [structure] | 629.59 | 2.12 | 1.59 |
| [structure] | 568.50 | 6.24 | 0.00 |
| [structure] | 614.52 | | 0.14 |
| [structure] | 589.51 | 1.08 | 1.27 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| [structure] | 597.60 | 2.41 | 2.55 |
| [structure] | 681.61 | 1.39 | 1.88 |
| [structure] | 587.51 | 2.99 | 0.11 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| [structure] | 566.52 | 7.32 | |
| [structure] | 963.95 | 0.93 | 1.94 |
| [structure] | 586.53 | 0.80 | −0.50 |
| [structure] | 651.54 | 1.82 | 1.57 |

-continued
TABLE OF COMPOUNDS
| COMPOUND | MOL. WT. | $k_{cat}$ pH 7.4 $\times 10^{-7} M^{-1} s^{-1}$ | Log P |
|---|---|---|---|
| 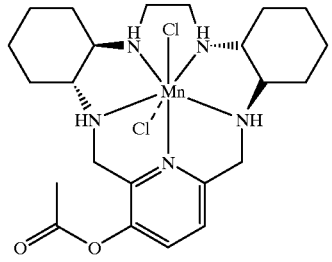 | 541.43 | 1.93 | −0.43 |
| 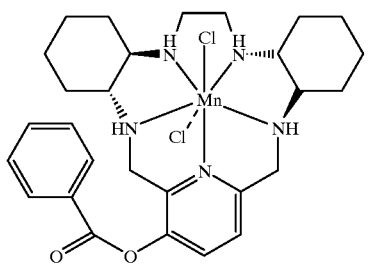 | 603.49 | 0.95 | 0.87 |
| 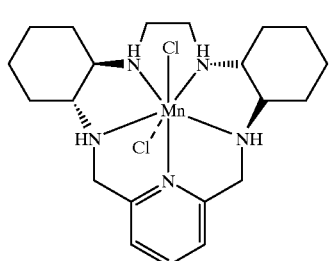 | 562.28 | 1.68 | 0.63 |
| 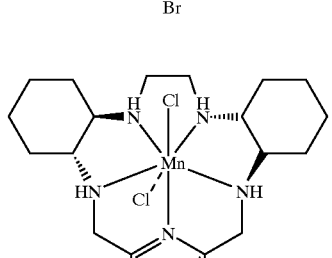 | 641.50 | 1.31 | 0.31 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| [structure with S-CH2CH2CH2-OH substituent] | 573.53 | 3.97 | 0.19 |
| [structure with S-CH2-COOH substituent] | 537.02 | 3.01 | −0.04 |
| [structure with cyclohexyl substituent] | 579.56 | 2.68 | 2.29 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| (structure with isopropylthio substituent) | 557.55 | 1.86 | 1.44 |
| (structure with sec-butylthio substituent) | 571.56 | 1.85 | |
| (structure with ethyl thioacetate substituent) | 601.53 | 3.32 | 0.57 |
| (structure with 2-(hydroxymethyl)phenylthio substituent) | 620.00 | | |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| | 634.00 | 2.16 | 2.05 |
| | 620.00 | 2.32 | |
| | 620.00 | 2.12 | 1.56 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| | 634.00 | | |
| | 624.51 | 0.70 | 2.41 |
| | 705.61 | 0.80 | 2.77 |

-continued

TABLE OF COMPOUNDS

| COMPOUND | MOL. WT. | $k_{cat}$ pH 7.4 $\times 10^{-7} M^{-1} s^{-1}$ | Log P |
|---|---|---|---|
| (structure) | 639.60 | 1.89 | 1.42 |
| (structure) | 645.61 | 1.45 | 2.17 |
| (structure) | 683.58 | 2.40 | 0.28 |

Activity of these catalysts for the dismutation of superoxide can be demonstrated using the stopped-flow kinetic analysis technique as described in Example 3, and in Riley, D. P., Rivers, W. J. and Weiss, R. H., "Stopped-Flow Kinetic Analysis for Monitoring Superoxide Decay in Aqueous Systems," Anal. Biochem., 196, 344–349 (1991), which is incorporated by reference herein. Stopped-flow kinetic analysis is an accurate and direct method for quantitatively monitoring the decay rates of superoxide in water. The catalytic constants given for the exemplary compounds in the table above were determined using this method.

As can be observed from the table, a wide variety of substituted, unsaturated heterocyclic complexes with superoxide dismutating activity may be readily synthesized. The commonly accepted mechanism of action of the manganese-based SOD enzymes involves the cycling of the manganese center between the two oxidation states (II, III). See J. V. Bannister, W. H. Bannister, and G. Rotilio, Crit. Rev. Biochem., 22, 111–180 (1987).

$$Mn(II)+HO_2 \rightarrow Mn(III)+HO_2^- \quad 1)$$

$$Mn(III)+O_2^- \rightarrow Mn(II)+O_2 \quad 2)$$

The formal redox potentials for the $O_2^-/O_2$ and $HO_2/HO_2^-$ couples at pH=7 are −0.33 v and 0.87 v, respectively. See A. E. G. Cass, in Metalloproteins: Part 1, Metal Proteins with Redox Roles, ed. P. Harrison, P. 121. Verlag Chemie (Weinheim, GDR) (1985). For the above disclosed mechanism, these potentials require that a putative SOD catalyst be able to rapidly undergo oxidation state changes in the range of −0.33 v to 0.87 v. Thus, as long as the redox potential of the ion is in a range in which superoxide anion can reduce the oxidized metal and protonated superoxide can oxidize the reduced metal, and steric hindrance of the approach of the superoxide anion is minimal, the catalyst will function with a $k_{cat}$ of about $10^{-6}$ to $10^{-8}$.

The complexes derived from Mn(II) and the general class of C-substituted [15]aneN$_5$ ligands described herein have been characterized using cyclic voltammetry to measure their redox potential. The C-substituted complexes described herein have reversible oxidations of about +0.7 v (SHE). Coulometry shows that this oxidation is a one-electron process; namely it is the oxidation of the Mn(II) complex to the Mn(III) complex. Thus, for these complexes to function as SOD catalysts, the Mn(III) oxidation state is involved in the catalytic cycle. This means that the Mn(III) complexes of all these ligands are equally competent as SOD catalysts, since it does not matter which form (Mn(II) or Mn(III)) is present when superoxide is present because superoxide will simply reduce Mn(III) to Mn(II), liberating oxygen.

Without limiting themselves to any particular theory, applicants propose that the mechanism described in Riley, et al., 1999, is a reasonable approximation of how these catalysts dismutate superoxide. In order for the complex to exhibit superoxide dismutase activity, the ligand should be able to fold into a conformation that allows the stabilization of an octahedral complex between an axial ligand and the five nitrogens of the ligand ring. If a compound contains several conjugated double bonds within the main 15-membered ring of the ligand, which hold the ring in a rigid conformation, the compound would not be expected to exhibit catalytic activity. R groups attached to the macrocyclic ligand which lock it in a planar conformation would be expected to be poor catalysts. One of ordinary skill in the art would not be surprised that these types of derivatives would lack superoxide dismutase activity Specifically, one of skill in the art would avoid materially changing the flexibility of the macrocycle by adding many large groups which would cause steric hindrance, or placing too many double bonds into the main ring. This effect would also be present in certain geometric arrangements of smaller R groups which constrain the complex to a rigid, planar geometry. Given these examples and guidelines, one of ordinary skill would be able to recognize which of the described pentaazacyclopentadecane complexes of the present invention would retain superoxide dismutating activity.

The catalysts of the present invention may be produced by the methods disclosed in U.S. Pat. No. 5,610,293. However, it is preferred that the catalysts of the present invention be synthesized by the template method, diagrammed below. This synthesis method is advantageous over previously disclosed methods in that cyclization yields utilizing the template method are usually about 90%, as compared to about 20% with previous methods. Several diamines are commercially available as starting materials, or a diamine may be synthesized. The diamines are reacted with titryl chloride in anhydrous methylene chloride at 0° C. and allowed to warm to room temperature overnight, with stirring. The product is then combined with glyoxal in methanol and stirred for 16 hours. The glyoxal bisimine product is then reduced with a borohydride in THF. If a symmetrical product is desired, one diamine may be used as the starting material. In addition, a substituted glyoxal may be used if groups pendant from the macrocycle opposite the pyridine are desired ($R_5$ and $R_6$) Commercially available tetraamines may also be used in place of the reduced glyoxal bisimine. After reduction of the glyoxal bisimine, the product is combined with a 2,6 dicarbonyl substituted pyridine, such as 2,6-dicarboxaldehyde pyridine or 2,6 diacetylpyridine, and a salt of manganese or iron under basic conditions. The transition metal ion serves as a template to promote cyclization of the substituted pyridine and the tetraamine. Several 2,6 dicarbonyl substituted pyridines are available commercially, allowing for the facile production of a variety of ligands with groups pendant from the macrocycle proximal to the pyridine ($R_2$ and $R_9$). Pyridines with one or more substituents ($R_A$, $R_B$ and $R_C$) are used when synthesizing the catalysts of the present invention in order to obtain the substituted, unsaturated heterocyclic moiety. After cyclization, the product is reduced with ammonium formate and a palladium catalyst over a period of 3–4 hours. Alternatively, in a less preferred embodiment of this method of making the compounds of the present invention, the bisimine may be reduced with a hydride reductant such as NaBH$_4$, or with hydrogen gas and a metal catalyst. In addition to the "R" substitutions, "R'" groups may also be substituted at the same carbons. "R" and "R'" groups may be any of those indicated above. The process may be varied according

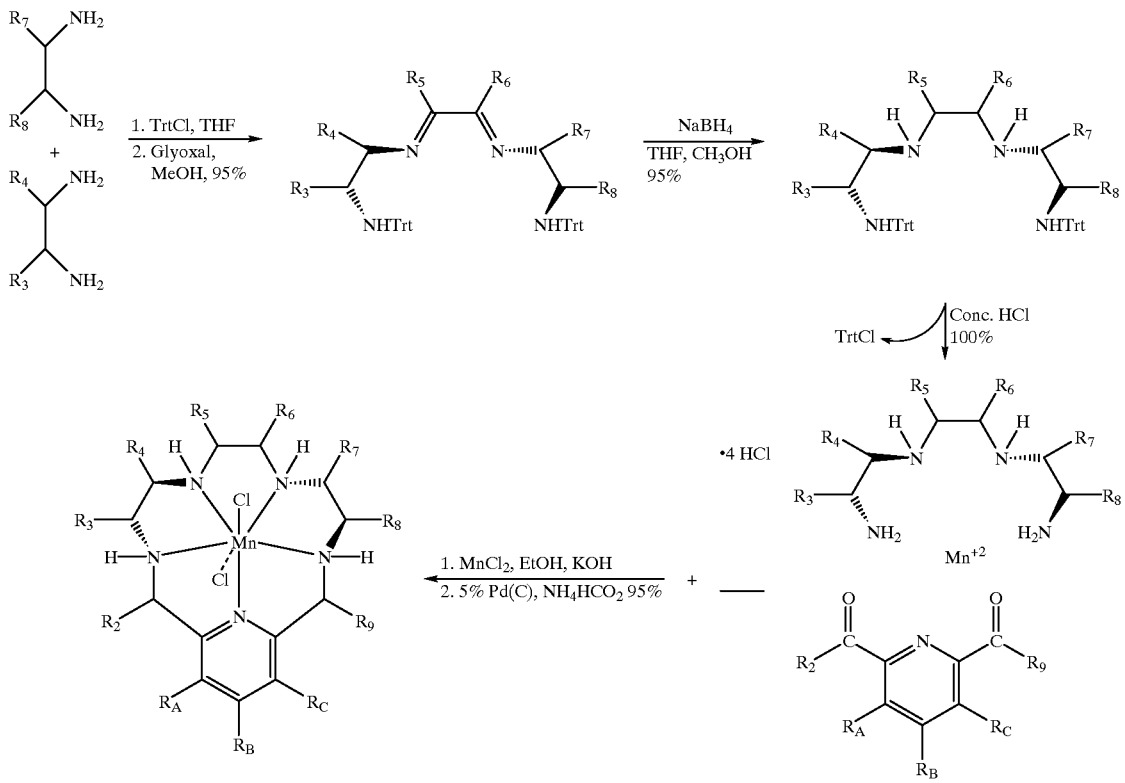

to principles well known to one of ordinary skill in the art in order to accommodate various starting materials.

Although the bisimine produced in the template cyclization reaction step above may be reduced by more conventional means using hydrogen gas, it is preferred that the bisimine be reduced with ammonium formate in the presence of a catalyst, as illustrated in Example 2. The preferred catalyst for use in this process comprises palladium, although a catalyst comprising other catalytic metals such as nickel, rhodium, platinum, platinum oxide, and ruthenium would also be potentially suitable. This process offers the advantages of increased safety and high reduction efficiency of the imine bonds, while preserving the double bonds of the pyridine groups in the heterocyclic moiety of the preferred compounds. In addition, this method can be accomplished in a more concentrated medium as compared to hydrogen or borohydride reduction, allowing for faster reaction times.

Another synthesis method which is useful in making several catalysts of the present invention is the post-chelation nucleophilic substitution scheme outlined in Example 7. Several advantages are realized by using this process of the present invention. First, one is able to use commercially available or relatively easily synthesized reactants in the above template cyclization synthesis, such as 4-chloro-2,6 dicarboxaldyhyde pyridine, and then modify the resultant chelated macrocyclic ligand without side reactions with the substituted group. Second, because this method allows modification of the chelated ligand, no post-modification reaction with manganese chloride is necessary, simplifying the synthesis process. A leaving-group-substituted pyridine pentaazacyclopentadecane chelated ligand is used as the starting material in the modification reaction. Preferred nucleophilic 4-pyridino substituents which are good leaving groups are the halides. Cl, Br, and I are more preferred substituents. To the SOD mimic catalyst in DMF (or another appropriate solvent) at reduced temperature is added a nucleophile (1 eq.), dropwise, and the reaction mixture stirred overnight. The solvent is then removed, in vacuo, the resulting mixture extracted with methylene chloride, and then concentrated down, in vacuo. The SOD mimic catalyst may then be purified by flash column chromatography. Nucleophiles for use in this modification reaction may be any strong nucleophile. Applicants have found that thiolates have provided a wide array of post-chelation modification reagents useful for making the compounds of the present invention. Although this method has been used primarily with the preferred pyridino compounds, the same synthesis method could be used with other SOD mimics of the present invention which have nucleophile substituted nitrogen containing aryl moieties, such as a 4-chloro pyrimidino complex.

Although manganese is usually used as the chelated transition metal ion in the examples of this disclosure, it is to be understood that the disclosed ligands may be just as easily complexed with iron (II) or iron (III) cations obtained from salts such as $FeCl_3$. In general, better catalytic activity has been observed with the use of manganese as the chelated transition metal ion, although $k_{cat}$'s which are as high as $10^{-7}$ are still observed with the use of iron. Thus, manganese is preferred as the chelated transition metal ion in the complexes of the present invention.

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The compounds of the present invention have been shown to have remarkable potency and utility in several models of disease. In Example 14, the utility of the present compounds for the treatment of pain and inflammation is demonstrated in the rat paw carrageenan model. The substituted, unsaturated, nitrogen-containing heterocyclic compounds sometimes differ remarkably from the base compound (compound A) in terms of their potency, onset of analgesia, and duration of effect. As may be noted, the substitution of various small ester groups on the nitrogen containing heterocyclo moiety produces a very rapid onset of analgesic action. In addition, the benzyl ether substituted complex is particularly potent in this model as compared to Compound A or B, both of which have higher rates of catalytic superoxide dismutation. Because of the different analgesia time profiles of these compounds, these compounds may find special applications in different areas of pain treatment. Or, several of these may be combined in order to provide a steady level of pain relief. Overall, the compounds exhibit a remarkable variety of effects as compared to the parent Compound A.

In Example 15, the efficacy of the compounds in a murine model of opioid tolerance reversal is shown by both iv and subcutaneous administration. As compared to the previously disclosed Compounds A and B, several of the compounds of the present invention show astounding efficacy in the prevention of morphine tolerance in this model. For instance, in iv administration, Compounds 13 and 14 show a very significant reversal of morphine tolerance at $\frac{1}{30}$ of the concentration necessary to achieve roughly ½ the effect with Compound A. Compound 28 is shows a 100% reversal of morphine tolerance at $\frac{1}{100}$ the concentration needed for the same effect with Compound A, in iv administration. Similar results were obtained with subcutaneous administration, in which Compound 3 showed 100% reversal of morphine tolerance at $\frac{1}{100}$ the dose necessary to achieve the same effect with Compound A. Thus, the compounds of the present invention show remarkable utility for preventing or reversing opioid tolerance.

In addition, Compounds 25 and 31 were also tested for their ability to prevent refractory hypotension in an endotoxemic rat model, Example 16. Both of these compounds were effective at preventing hypotension in endotoxemic animals at ⅓ the dose used to achieve a similar effect with Compound A.

As demonstrated by Examples 14, 15, and 16, the compounds or complexes of the present invention are can be utilized to treat numerous disease states and disorders in a patient in need thereof. The terms "patient" and "subject" includes human and non-human animals in need of treatment. Such disease states and disorders include, but are not limited to: reperfusion injury to an ischemic organ, such as reperfusion injury to the ischemic myocardium, general inflammation, inflammatory bowel disease, rheumatoid arthritis, osteoarthritis, hypertension, psoriasis, organ transplant rejections, refractory hypotension, organ preservation, radiation-induced injury, platelet aggregation, stroke, autoimmune diseases, adult respiratory distress, carcinogenesis, severe chronic pain, hyperalgesia, and sepsis. The complexes of this invention are excellent analgesics and can be used to treat or prevent pain in a subject arising from any hyperalgesic state. The complexes further have activity to prevent or reduce tolerance to opiates, and to potentiate the analgesic activity of opiates without potentiating the respiratory depression associated with opiates. In addition, the complexes are useful in treating withdrawal symptoms associated with addiction to opiates, nicotine, or other drugs. The complexes of this invention can also be used systemically or topically to prevent or reverse free oxygen radical-mediated symptoms of aging, such as skin wrinkling, and to prevent or reverse environmental damage caused by exposure to ultraviolet radiation or chemical agents.

Total daily dose administered to a subject in single or divided doses may be in amounts, for example, from about 0.00025 to about 20 mg/kg body weight daily, more preferably from about 0.001 to about 10 mg/kg body weight daily, and more usually about 0.01 to about 3 mg/kg body weight daily, when given as a parenteral injection or continuous infusion. Dosage unit compositions may contain such amounts of sub-multiples thereof to make up the daily dose. The amount of active ingredient that may be combined with the carrier materials to produce a single dosage form will vary depending upon the subject treated and the particular mode of administration. For instance, systems such as transdermal administration or oral administration, which are substantially less efficient delivery systems, may require dosages at least an order of magnitude above those required for parenteral administration. The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above. Those of ordinary skill in the art can readily determine appropriate dosages for any particular subject based on the teachings in this specification and routine analysis of the subject.

The compounds of the present invention may be administered by any technique known to those of ordinary skill, including but not limited to, orally, parenterally, by inhalation spray, rectally, topically or by nasal, vaginal or ocular administration, in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrastemal injection, intrathecal or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug. Solid dosage forms for oral administration may include capsules, tablets, pills, powders, granules and gels. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

As shown in Table 1, the compounds of the present invention make exceptional catalysts for the dismutation of superoxide. Thus, they can be used in this catalytic capacity in a variety of in vivo and in vitro applications where a reduction in superoxide concentration is desired.

The SOD mimic compounds of the present invention can also be added to rinse or storage solutions for organs and tissues, such as for organ transplantation or for surgical rinses. For example, excised organs are often placed in a preservation solution prior to transplant into a recipient. Inclusion of at least one species of SOD mimic in a preservation solution, usually at a concentration of about 0.01 mM to 10 mM, is desirable for reducing damage due to ischemia during storage and reperfusion injury following reimplantation in the recipient. Various solutions described in the art are suitable for the inclusion of these compounds of the invention, including but not limited to those described in U.S. Pat. No. 5,145,771; Beyersdorf(1990) Chem Abst. 113: 84849w; U.S. Pat. No. 4,879,283; U.S. Pat. No. 4,873,230; and U.S. Pat. No. 4,798,824, incorporated herein by reference. The compounds of the present invention can also be added to extravasated blood for transfusion to inhibit oxyradical damage to the blood cells and components during storage; similarly, these compounds can also reduce oxyradical damage to blood cells in vivo.

Typically the SOD mimic of the present invention is present in the rinse or storage solution at a concentration of about 0.001 mM to about 10 mM, and most usually is present at 1 mM. For example, but not to limit the invention, a suitable rinse solution comprises Ringer's solution (102 mM NaCl, 4 mM KCl, 3 mM CaCl2, 28 mM sodium lactate, pH 7.0) or Ringer's solution with 0.1 mM adenosine, and Compound 1 at a final concentration of 1 mM. The rinse solution can further comprise additional antioxidants (e.g., glutathione, allopurinol). Preservation or rinse solutions containing a SOD mimic of the present invention can be used to provide enhanced storage or irrigation of organs (e.g., kidney, liver, pancreas, lung, fetal neural tissue, heart, vascular grafts, bone, ligament, tendon, skin)which is believed to enhance the viability of the tissue and increase resistance to oxidative damage (e.g., as a consequence of ischemia/reperfusion).

Alternatively, the capacity of the compounds of the present invention to catalyze the decomposition of reactive oxygen species can be used to advantage to inhibit or slow damage to biological tissues and cells. For example, oxyradical-induced damage to connective tissues (e.g., collagen) attendant to exposure to UV light, cigarette smoking, and senescence may be reduced by administration of an SOD mimic compound of the present invention approximately concomitant with the exposure to UV light, cigarette smoking, or other oxyradical-generating process (e.g., cellular senescence).

The SOD mimics of the present invention can also be formulated into a lipophilic base (or, if desired, an aqueous carrier) for topical application in cosmetics or sunburn-prevention creams and lotions. A typical cosmetic or sunburn-prevention cream or lotion will comprise about between 1 mg to 50 mg of SOD mimic compound per gram of cosmetic or sunburn-prevention cream or lotion. The compounds of the present invention can be formulated into a cosmetic base for topical application and/or for reducing oxidation of the cosmetic by molecular oxygen and oxyradicals. The pharmaceutical/cosmetic compositions of the present invention formulated as solutions typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the salen-metal compound, and optionally also an anti-inflammatory agent, also possesses acceptable safety (e.g. irritation and sensitization characteristics), as well as good aesthetic properties (e.g., does not feel greasy or tacky). The most typical example of such a solvent is isopropanol. Examples of other suitable organic solvents include: propylene glycol, polyethylene glycol (200-600), polypropylene glycol (425-2025), glycerol, 1,2,4-butanetriol, sorbitol esters, 1,2,6-hexanetriol, ethanol, butanediol, water and mixtures thereof. These solutions contain from about 0.001% to about 20%, preferably from about 0.1% to about 10%, antioxidant salen-metal complex, from about 0.01% to about 5%, preferably from about 0.5% to about 2% of an anti-inflammatory agent, and from about 80% to about 99%, preferably from about 90% to about 98%, of an acceptable organic solvent.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials. Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives.

The invention also provides methods for preventing food spoilage and oxidation by applying to foodstuffs an effective amount of at least SOD mimic compound of the present invention, optionally in combination with at least one additional food preservative agent (e.g., butylated hydroxytoluene, butylated hydroxyanisole, sulfates, sodium nitrite, sodium nitrate). In another aspect, the invention relates to antioxidant compositions and methods of use in inhibiting formation of undesired hydrocarbon polymers generated via free radical-mediated polymerization mechanisms, especially oxyradical-mediated polymerization and/or oxyradical-mediated rancidification or gum formation. The SOD mimic compounds of the invention can be applied to a variety of hydrocarbons to reduce undesired oxidation and/or polymerization, or to quench a polymerization reaction at a desired state of polymer formation (e.g., at a desired average chain length). For example and not to limit the invention, examples of such saturated and unsaturated hydrocarbons include: petroleum distillates and petrochemicals, turpentine, paint, synthetic and natural rubber, vegetable oils and waxes, animal fats, polymerizable resins, polyolefin, and the like.

The compounds of the present invention may also be used to protect cells and tissues from free radical-producing agents, such as ionizing radiation and chemotherapeutic agents (e.g., bleomycin). Preferably, a protective dosage comprising at least about 0.001 mg of SOD mimic/kg body weight is administered by one or more of several routes (e.g., oral, intravenous, intraperitoneal, intragastric lavage, enema, portal vein infusion, topical, or inhalation of mist) to protect normal cells, for example, against free radical toxicity associated with chemotherapy or radiotherapy of a neoplasm. The compounds of the present invention are preferably pre-administered to the patient prior to the commencement of the chemotherapy and/or radiotherapy, usually within about 24 hours of commencement, and preferably within about 3–6 hours of commencement of the chemotherapy and/or radiotherapy. The compounds may be continually administered to the patient during the course of therapy.

The SOD mimics of the present invention also can be administered to individuals to prevent radiation injury or chemical injury by free radical generating agents. Military personnel and persons working in the nuclear, nuclear medicine, and/or chemical industries may be administered the compounds of the present invention prophylactically. These may also be used as chemoprotective agents to prevent chemical carcinogenesis; particularly by carcinogens which form reactive epoxide intermediates (e.g., benzo->a!-pyrene, benzanthracene) and by carcinogens or promoting agents which form free radicals directly or indirectly (e.g., phenobarbital, TPA, benzoyl peroxiprolieroxisome proliferators: ciprofibrate, clofibrate). Persons exposed to such chemical carcinogens are pretreated with the compounds of the present invention to reduce the incidence or risk of developing neoplasia.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

General Experimental

Analytical thin layer chromatography (TLC) was performed on Analtech 0.15 mm silica gel 60-GF plates. Visualization was accomplished with UV light, exposure to iodine or by oxidation with phosphomolybdic acid. Solvents for extractions were HPLC or ACS grade. Chromatography was performed by the method of Still with Merck silica gel 60 (230–400 mesh) with the indicated solvent system. All reactions were performed under a positive pressure of Argon. NMR spectra were collected on Varian Unity 400, VXR-400, and VXR-300 spectrometers. $^1$H NMR spectra are reported in ppm from tetramethylsilane on the δ scale. Data are reported as follows: chemical shift, multiplicity (s=singlet, d=doublet, t=triplet, q=quartet, m=multiplet, br=broadened, obs=obscured), coupling constants (Hz) and relative integration. $^{13}$C NMR spectra are reported in ppm from the central deuterated solvent peak (e.g. 39.0 ppm for DMSO-$d_6$). Data are reported as follows: chemical shift, multiplicity.

Example 1

Synthesis of Dicyclohexyl Tetraamine Tetrahydrochloride

A. Synthesis of N-(triphenylmethyl)-(1R, 2R)-diaminocyclohexane.

To a solution of(1R,2R)-diaminocyclohexane (250 g, 2.19 mol) in anhydrous CH2Cl2 (3.5 L) at 0° C. was added a solution of trityl chloride (254 g, 912 mol) in anhydrous $CH_2Cl_2$ (2 L) dropwise over 4 hours. The resulting mixture was allowed to warm to room temperature and stirred overnight. The reaction mixture was washed with water until the pH of the aqueous washes was below 8.0 (4×2000 ml) and dried over $Na_2SO_4$. Filtration and concentration of the solvent afforded 322.5 g (99% yield) of N-(triphenylmethyl)-(1R, 2R)-diaminocyclohexane as a glass: $^1$H NMR (300 MHz, DMSO-$d^6$) d 7.50 (d, J=7.45 Hz, 6 H), 7.26 (app t, J=7.45 Hz, 6 H), 7.16 (app t, J=7.25 Hz, 3 H), 2.41 (dt, J=10.3, 2.62 Hz, 1 H), 1.70 (m, 1 H), 1.54–0.60 (complex m, 8 H). 13$_C$ NMR (75 MHz, DMSO-$d^6$) dc 147.2 (s), 128.4 (d), 127.3 (d), 69.9 (s), 59.0 (d), 54.4 (d), 36.6 (t), 32.5 (t), 24.6 (t), 24.3 (t). MS (LR-FAB) m/z=363 [M+Li]+.

B. Glyoxal bisimine of N-(triphenylmethyl)-(1R, 2R)-diaminocyclohexane.

To a solution of N-(triphenylmethyl)-(1R, 2R)-diaminocyclohexane (322.5 g, 905 mmol) in methanol (4 L) was added glyoxal (51.9 ml of a 40% solution in water, 452.3 mmol), dropwise over 30 minutes. The resulting mixture was stirred for 16 hours thereafter. The precipitated product was isolated by filtration and dried under vacuum to afford 322.1 g (97 % yield) of bisimine as a white solid: $1_H$ NMR (300 MHz, CDCl₃) d 7.87 (s, 2 H), 7.51 (d, J=8.1 Hz, 12 H), 7.16–7.05 (m, 18 H), 2.95 (bm, 2 H), 2.42 (bm, 2 H), 1.98–0.81 (complex m, 18 H). $13_C$ NMR (100 MHz, CDCl₃) dc 161.67 (d), 147.24 (s), 147.22 (s), 128.90 (d), 128.81 (d), 127.73 (d), 127.61 (d), 126.14 (d), 73.66 (s), 70.86 (d), 70.84 (d), 56.74 (d), 32.45 (t), 31.77 (t), 24.02 (t), 23.62 (t). MS (LR-ESI) m/z 757 [M+Na]+.

C. N,N'-Bis{(1R,2R)-[2-(Triphenylmethylamino)]cyclohexyl}-1,2-diaminoethane.

The glyoxal bisimine of N-(triphenylmethyl)-(1R,2R)-diaminocyclohexane (586 g, 798 mmol) was dissolved in THF (6 L) and treated with LiBH4 (86.9 g, 4.00 mol) at room temperature. The mixture was stirred for 12 hours at room temperature and warmed to 40° C. for 4 hours thereafter. The reaction was carefully quenched with water (1 L) and the THF was removed under reduced pressure. The residual slurry was partitioned between CH₂Cl₂ (3 L) and water (1 additional L). The layers were separated and the aqueous was extracted again with CH₂Cl₂ (1 L). The combined CH₂Cl₂ layers were dried (MgSO4), filtered and concentrated to afford 590 g (100% yield) of N,N'-bis{(1R,2R)-[2-(triphenylmethylamino)]cyclohexyl}-1,2-diaminoethane as a white foam: MS (LR-ESI) m/z 739 [M+H]+.

D. N,N'-Bis{(1R,2R)-[2-(amino)]cyclohexyl}-1,2-diaminoethane tetrahydrochloride.

To a solution of N,N'-bis{(1R,2R)-[2-(triphenylmethylamino)]cyclohexyl}-1,2-diaminoethane (590 g, 798 mmol) in acetone (3 L) was added concentrated HCl (1.5 L). The reaction was stirred for 2 hours and concentrated. The residue was partitioned between water (2 L) and CH₂Cl₂ (1 L). The layers were separated and the aqueous was concentrated and dried under vacuum to afford 257 g (80% yield) of the tetrahydrochloride as a granular off-white solid: $1_H$ NMR (300 MHz, CDCl₃) d 3.82–3.57 (complex m, 8 H), 2.42 (d, J=9.9 Hz, 2 H), 2.29 (d, J=9.3 Hz, 2 H), 2.02–1.86 (complex m, 4 H), 1.79–1.60 (complex m, 4 H), 1.58–1.42 (complex m, 4 H). $13_C$ NMR (75 MHz, CDCl₃) dc 59.1 (d), 51.3 (d), 40.8 (t), 29.2 (t), 26.0 (t), 22.3 (t), 22.2 (t). MS (LR-FAB) m/z 255 [M+H]+.

Example 2

Use of Catalytic Ammonium Formate Reduction in the Synthesis of the Compounds of the Invention The purified bisimine precursor to Compound B (15.0 g, 29.6 mmol) was dissolved in 1.5 L of anhydrous MeOH and the flask flushed with nitrogen for a few minutes, then 3% Pd/C (7.5 g, 50% by weight) was added. As the suspension was heated, solid ammonium formate (7.5 g, 118.9 mmol, 4 equiv.) was carefully added. One hour after reflux was attained, a second portion of formate (3.75 g, 59.5 mmol, 2 equiv.) was added. The black suspension was allowed to cool to RT after 2.5 h of reflux (at this point the supernatant was virtually colorless), and filtered through a ½-inch bed of alumina (Al₂O₃, Brockmann grade, neutral, and previously washed with MeOH). The bed of catalyst and alumina was washed with MeOH (2×100 mL), and the combined solvent removed under reduced pressure. Upon drying in vacuo at RT overnight, the residual light yellow foam was stirred with CH₂Cl₂ (500 mL) for 15–20 min., then filtered through a 10μ filter. Upon solvent removal, 14.7 g of a light yellow foam were isolated. The foam was dissolved in 600 mL of deionized water and the pH of the green solution brought up from the initial 4.9 to ca. 7.5 with 0.5N aq. NaOH. Then, 90 g of NaCl were added to bring the NaCl content up to 15%. Once a solution had resulted, extraction with CH₂Cl₂ followed (4×250 mL). the combined organic extracts were dried over 10 g of anhydrous Na₂SO₄ for 15 min., then filtered, and the solvent removed under reduced pressure to afford a light yellow-green foam (14.5 g, 96% yield). HPLC of this material indicated a 3.8:1 ratio of S,S- to S,R-isomers and a combined purity of ≧98%.

Hydrogen Transfer Results

| Concentration (mM)[a] | Catalyst (% Pd/C)[b] | % by Wt. | Time (hours)[c] | HCO₂⁻ (eq.) | % Area by HPLC[d] | | | | |
|---|---|---|---|---|---|---|---|---|---|
| | | | | | Free Ligand | Mono-imine | SS-isomer | SR-isomer | Ratio |
| 20 | 10 | 50 | 2 | 25 | — | — | 68 | 32 | 2.13 |
| 20 | 5 | 50 | 2 | 25 | 2 | — | 75 | 23 | 3.26 |
| 20 | 5 | 10 | 4 | 25 | 2 | 7 | 64 | 27 | 2.37 |
| 20 | 3 | 50 | 2 | 25 | 2 | 2 | 75 | 21 | 3.57 |
| 20 | 1 | 50 | 4[e] | 16 | — | 55 | 26 | 21 | 1.24 |
| 20[f] | 3 | 50 | 2 | 16 | 1 | — | 70 | 28 | 2.50 |
| 20 | 3 | 50 | 3 | 6 | — | <1 | 79 | 21 | 3.76 |
| 28[g] | 3/5 | 50 | 2.5 | 8 | 3 | — | 72 | 23 | 3.13 |
| 20[h] | 3 | 50 | 2 | 6 | 3 | — | 76 | 21 | 3.62 |
| 50 | 3 | 50 | 2 | 16 | 4 | — | 70 | 25 | 2.80 |
| 100 | 3 | 50 | 2 | 16 | 9 | <1 | 64 | 26 | 2.46 |

[a]Solvent is anhydrous MeOH.
[b]Available form Aldrich.
[c]Reflux time.
[d]Conditions: 3 mL/min. 10–50% B over 9 min. B is (8:2 v/v) MeCN: water, A is 0.5N aq. NaCl. UV-detection at 265 mn.
[e]Supernatant was still colored yellow after 4 hours.
[f]Solvent was anhydrous DtOH, and crude bisimine was used.
[g]Crude bisimine was used.
[h]Scale was 15 grams of purified bisimine.

Example 3

Evaluation of Superoxide Dismutase Activity by Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196: 344–349 1991). For the attainment of consistent and accurate measurements all reagents were biologically clean and metal-free. To achieve this, all buffers (Calbiochem) were biological grade, metal-free buffers and were handled with utensils which had been washed first with 0.1N HCl, followed by purified water, followed by a rinse in a 10–4 M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (about 100 mg). The powder was then ground with a few drops of DMSO and the slurry transferred to a flask containing an additional 25 ml of DMSO. The resultant slurry was stirred for ½ h and then filtered. This procedure gave reproducibly about 2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and $1.0 \times 10^{-6}$ M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanoohms/cm2.

The stopped-flow spectrometer system was designed and manufactured by Kinetic Instruments Inc. (Ann Arbor, Mich.) and was interfaced to a MAC IICX personal computer. The software for the stopped-flow analysis was provided by Kinetics Instrument Inc. and was written in Quick-Basic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60–120 μM. Since the published extinction coefficient of superoxide in H2O at 245 nm is .about.2250M-1 cm-1 (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was filled with 5 ml of the DMSO solution while the other was filled with 5 ml of the aqueous buffer solution. The entire injection block, mixer, and spectrometer cell were immersed in a thermostated circulating water bath with a temperature of 21.0°±0.5° C. Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was about 1.2 times 10–4 M, we wanted to use a manganese (II) complex concentration that was at least 20 times less than the substrate superoxide. Consequently, we generally screened compounds for superoxide dismutating activity using concentrations ranging from $5 \times 10^{-7}$ to $8 \times 10^{-6}$ M. Data acquired from the experiment was imported into a suitable math program (e.g., Cricket Graph) so that standard kinetic data analyses could be performed. Catalytic rate constants for dismutation of superoxide by manganese(II) complexes were determined from linear plots of observed rate constants (kobs) versus the concentration of the manganese(II) complexes. kobs values were obtained from linear plots of ln absorbance at 245 nm versus time for the dismutation of superoxide by the manganese(II) complexes.

Example 4

Synthesis of Compound 3

A. Synthesis of Dimethyl 4-chloro-2,6-pyridinedicarboxylate.

To a stirred suspension of chelidamic acid (200 g, 1.10 mol) in $CHCl_3$ (2.00 L) was added $PCl_5$ (1.00 kg, 4.80 mol) in portions over 2 hours at room temperature under an nitrogen atmosphere. The mixture was then refluxed for 3 hours and the clear brown solution was allowed to cool to room temperature overnight. The solution was then cooled to 0° C. and a solution of triethylamine (215 mL, 1.54 mol) in MeOH (2.30 L) was added dropwise over 5–6 hours with the temperature being maintained at 0 to –10° C. After stirring an additional 1.5 hours, the mixture was allowed to warm to room temperature overnight. Concentration of the solution in vacuo resulted in the crystallization of a white solid, which was filtered and dried to give 110 g (43% yield) of the product as colorless needles: mp 141-2° C.; $^1H$ NMR ($CDCl_3$, 300 MHz), δ 8.31 (s, 2 H), 4.05 (s, 6 H); $^{13}C$ NMR ($CDCl_3$, 75 MHz) δ 164.09, 149.44, 146.79, 128.29, 53.48; FAB mass spectrum (NBA–Li) m/z (relative intensity) 252 (30) $[M+Na]^+$, 236 (91) $[M+Li]^+$, 230 (100) $[M+H]^+$.

B. Synthesis of Dimethyl 4-cyclohexyl-2,6-pyridine-dicarboxylate.

To a stirred solution of cyclohexylmagnesium chloride (78.5 mL of 2M in ethyl ether, 157 mmol) at –78° C. was added a soution of $ZnBr_2$ (35.5 g, 157 mmol) in anhydrous THF (150 mL) at –78° C. The mixture was stirred for 1 hour at –78° C. and then allowed to warm to room temperature. A solution of tetrakis-(triphenylphosphine)palladium(0) (7.50 g, 6.47 mmol) in anhydrous THF (100 mL) was then added at room temperature, followed by dimethyl 4-chloro-2,6-pyridinedicarboxylate (30.0 g, 131 mmol) in anhydrous THF (150 mL). The mixture was then warmed to 50° C. for 3 hours and allowed to stand at room temperature overnight. The reaction was then quenched with saturated $NH_4Cl$ (250 mL) and $H_2O$ (50 mL). The layers were separated and the aqueous layer was extracted with ethyl acetate (3×80 mL). The combined organic layers were washed with saturated NaCl (2×50 mL) and dried over $MgSO_4$. Filtration and removal of the solvent in vacuo gave 41 g of a dark brown solid. The impure material was purified by flash chromatography (silica gel, 60:40 to 50:50 hexanes-$CH_2Cl_2$ gradient), followed by crystallization from ethyl acetate-hexanes to give 17.9 g (49.3% yield) of the product as an off-white solid: mp 113–5° C.; $^1$H NMR (CDCl$_3$, 300 MHz) δ 8.16 (s, 2 H), 4.02 (s, 6 H), 2.64–2.73 (m, 1 H), 1.88–1.96 (m, 4 H), 1.77–1.81 (m, 1 H), 1.22–1.56 (m, 5 H); $^{13}$C NMR (CDCl$_3$, 75 MHz) δ 165.44, 159.72, 148.24, 126.79, 53.13, 44.88, 33.23, 26.35, 25.72; FAB mass spectrum (NBA–Li) m/z (relative intensity) 561 (13) [2M+Li]$^+$, 300 (9) [M+Na]$^+$; 284 (27) [M+Li]$^+$, 278 (100) [M+H]$^+$, 218 (18) [M–HCO$_2$CH$_3$]$^+$;

Anal. Calcd for $C_{15}H_{19}NO_4$: C, 64.97; H, 6.91; N, 5.05. Found: C, 64.98; H, 6.84; N, 5.05.

C. Synthesis of 4-Cyclohexyl-2,6-pyridinedimethanol.

To a stirred solution of dimethyl 4-cyclohexyl-2,6-pyridinedicarboxylate (6.50 g, 22.5 mmol) in anhydrous THF (225 mL) was added LiBH$_4$ (1.96 g, 90.2 mmol) at room temperature, moderating the temperature with an ice bath. The orange solution was stirred under an argon atmosphere for 1.5 hours and then quenched by the slow addition of H$_2$O (100 mL). The solvent was removed in vacuo and the residue was dissolved in a mixture of ethyl acetate (500 mL) and H$_2$O (250 mL). The layers were separated and the ethyl acetate layer was washed with saturated NaHCO$_3$ (2×250 mL), saturated NaCl (250 mL) and was dried over Na$_2$SO$_4$. Filtration and removal of the solvent in vacuo gave a white crystalline solid which was purified by recrystallization from ethyl acetate-hexanes to give 4.65 g (92.7% yield) of the product as colorless needles: mp 106–8° C.; $^1$H NMR (400 MHz, CDCl$_3$) δ 7.04 (s, 2 H), 4.73 (s, 4 H), 3.85 (s, 2 H), 2.52 (m, 1 H), 1.74–1.87 (m, 5 H), 1.19–1.47 (m, 5 H); $^{13}$C NMR (100 MHz, CDCl$_3$) δ 158.89, 158.32, 118.13, 64.35, 44.06, 33.50, 26.48, 25.89; FAB mass spectrum (NBA–Li) m/z 228 [M+Li]$^+$.

D. Synthesis of 4-Cyclohexyl-2,6-pyridinedicarboxaldehyde.

To a stirred solution of oxalyl chloride (11.1 g, 87.2 mmol) in anhydrous CH$_2$Cl$_2$ (50 mL) at −60° C. was added a solution of anhydrous DMSO (14.9 g, 190 mmol) in anhydrous CH$_2$Cl$_2$ (25 mL) dropwise over 5 minutes. After stirring for 10 minutes at −60° C., a solution of 4-cyclohexyl-2,6-pyridinedimethanol (4.39 g, 19.8 mmol) in anhydrous DMSO (25 mL) was added dropwise over 5 minutes, and the resulting mixture was stirred at −60° C. for 20 minutes. Then, triethylamine (111 mL, 796 mmol) was added over 5 minutes and after stirring for 5 minutes at −60° C. the mixture was allowed to warm to room temperature. After 2 hours, H$_2$O (300 mL) was added and the mixture was extracted with CH$_2$Cl$_2$ (3×250 mL). The extracts were combined, washed with saturated NaCl (250 mL) and dried over Na$_2$SO$_4$. Filtration and removal of the solvent invacuo gave 5.38 g of a tan solid which was purified by flash chromatography (silica gel (98:2 CH$_2$Cl$_2$:MeOH) to give 3.86 g, (89.7% yield) of the product as a tan crystalline solid: $^1$H NMR (400 MHz, C$_6$D$_6$) δ 10.05 (s, 2 H), 7.72 (s, 2 H), 1.97 (d(t), J=9.7, 3.5 Hz, 1 H), 1.50–1.54 (m, 3 H), 1.33–1.37 (m, 2 H), 0.83–1.08 (m, 5 H); $^{13}$C NMR (100 MHz, C$_6$D$_6$) δ 192.32, 159.31, 153.55, 123.31, 43.49, 33.00, 26.38, 25.64; FAB mass spectrum (NBA–Li) m/z 224 [M+Li]$^+$; HR mass spectrum (ESI) m/z 218.1124 [M+H]$^+$ (218.1181 calcd for $C_{13}H_{16}NO_2$).

E. Synthesis of Manganese(II)dichloro 4R,9R,14R, 19R-3, 10,13,20,26-pentaaza-24-cyclohexyltetracyclo-[20.3.1.0$^{4,9}$.0$^{14,19}$]hexacosa-1(25),22(26),23-triene.

To a stirred suspension of tetraamine tetrahydrochloride prepared as in Example 1 (2.80 g, 7.00 mmol) in absolute ethanol (70 mL) was added KOH (1.79 g–88%, 28.0 mmol) and the mixture was stirred at room temperature under an argon atmosphere. After 30 minutes, MnCl$_2$ (881 mg, 7.00 mmol) was added and the suspension was stirred for an additional 30 minutes. 4-Cyclohexyl-2,6-pyridinedicarboxaldehyde (1.52 g, 7.00 mmol) was then added to the dark green mixture which was refluxed. After 65 hours, the reaction had gone to completion; only the bis(imine) was seen: mass spectrum (ESI) m/z (relative intensity) 525 (100) [M−Cl]$^+$, 245 (73) [M−2Cl]$^{++}$. Methanol (35 mL) was then added to the orange mixture and upon cooling to 0° C., NaBH$_4$ (1.06 g, 28 mmol) was added. The mixture was stirred for 1 hour at 0° C. and then allowed to warm to room temperature. After 5 hours, additional NaBH$_4$ (1.06 g, 28.0 mmol) was added and the mixture was stirred for 18 hours. The mixture was again cooled to 0° C., additional NaBH$_4$ (1.06 g, (28.0 mmol) was added and the mixture was stirred an additional 3 days. The solvent was removed in vacuo and the residue was dissolved in a mixture of H$_2$O (50 mL), saturated NaCl (250 mL) and CH$_2$Cl$_2$ (250 mL). The layers were separated and the aqueous solution was extracted with CH$_2$Cl$_2$ (250 ml). The extracts were combined, washed with saturated NaCl (250 ml) and dried over MgSO$_4$. Filtration and removal of the solvent in vacuo gave a brown solid. The crude product was purified by flash chromatography (silica gel, 98:2 CH$_2$Cl$_2$:MeOH) to give 2.22 g (56.1% yield) of the product as an off-white solid: ESI mass spectrum m/z (relative intensities) 529 (78) [M−Cl]$^+$, 247 (100) [M−2Cl]$^{++}$; HR mass spectrum (ESI) m/z (relative intensity) 531.2738 (31)/529.2748 (100) [M−Cl]$^+$ (531.2714/529.2744 calcd. for $C_{27}H_{45}N_5$MnCl). HPLC (Vydac 218TP54 protein and peptide C18; 82% H$_2$O with 0.1% TFA/20% CH$_3$CN to 100% H$_2$O with 0.1% TFA over 10 min; flow=2 mL/min; 5 μL inj. vol.) T$_r$=15.2 min. (100% purity).

Example 5

Synthesis of Compound 28

A. Synthesis of N,N'-Bis{(1R,2R)-2-[(triphenylmethyl) amino]cyclohexyl}-(1R)-methyl-1,2-diiminoethane.

To a stirred solution of N-(triphenylmethyl)-(1R,2R)-diaminocyclohexane synthesized as in Example 1 (224 g, 628 mmol) in 1.50 L MeOH was added a solution of pyruvic aldehyde (48.0 mL–40% in H$_2$O, 314 mmol) at room temperature under an argon atmosphere. The preciptate which formed within 30 minutes was crushed and allowed to stand for 16 hours. The solid was filtered, washed with MeOH and dried in vacuo to give 170 g (72.3% yield) of the product as a tan powder: mass spectrum (ESI) m/z (relative intensity) 755 (1) [M+Li]$^+$, 243 (100) [(C$_6$H$_5$)$_3$C]$^+$; HR mass spectrum (ESI) m/z 7.49.4597 [M+H]$^+$ (749.4583 calcd for $C_{53}H_{57}N_4$).

B. Synthesis of N,N'-Bis{(1R,2R)-2-[(triphenylmethyl) amino]cyclohexyl}-(1R)-methyl-1,2-diaminoethane.

To a stirred solution of N,N'-bis{(1R,2R)-2-[(triphenylmethyl)amino]-cyclohexyl}-(1R)-methyl-1,2-diiminoethane (170 g, 227 mmol) in a mixture of anhydrous THF (1.50 L) and MeOH (1.50 L) was added NaBH$_4$ (85.8 g, 2.27 mol) at −10° C. and the mixture was allowed to warm to room temperature. After 5 days, the solvents were removed in vacuo, the residue was dissolved in a mixture of H$_2$O (500 mL) and CH$_2$Cl$_2$ (1.00 L) and the layers were separated. The CH$_2$Cl$_2$ layer was washed with H$_2$O (500 mL), saturated NaCl (250 mL) and dried over MgSO$_4$.

Filtration and removal of the solvent in vacuo gave 178 g of the product in assumed quantitative yield as a yellow solid: $^1$H NMR (C$_6$D$_6$, 300 MHz) δ 7.66–7.80 (m, 12 H), 6.97–7.17 (m, 18 H), 3.88 (br s, 1 H), 3.28 (br s, 1 H), 2.43–2.63 (m, 2 H), 2.10–2.38 (m, 3 H), 1.64–1.90 (m, 5 H), 1.32–1.55 (m, 5 H), 0.94–1.21 (m, 7 H), 0.52–0.85 (m, 6 H); $^{13}$C NMR (C$_6$D$_6$, 75 MHz) δ 148.23, 147.99, 129.43, 129.35, 127.88, 127.82, 126.36, 126.26, 71.19, 71.13, 61.31, 58.88, 57.61, 50.90, 33.72, 33.31, 32.43, 31.14, 25.72, 24.92, 24.84, 24.61, 20.30; mass spectrum (ESI) m/z (relative intensity) 753 (3) [M+H]$^+$, 243 (100) [(C$_6$H$_5$)$_3$C]$^+$; HR mass spectrum (ESI) m/z 753.4900 [M+H]$^+$(753.4896 calcd for C$_{53}$H$_{61}$N$_4$).

C. Synthesis of N,N'-Bis[(1R,2R)-2-aminocyclohexyl]-(1R)-methyl-1,2-diaminoethane tetrahydrochloride.

To a flask containing N$_1$N'-Bis{(1R, 2R)-2-[(triphenylmethnyl)amino]cyclohexyl}-IR-methyl-1,2-diaminoethane, prepared as in Example 2B (40.0 g, 53.1 mmol) was added conc. HCl solution (250 mL), the suspension was stirred for 1 hour and then allowed to stand for 16 hours at room temperature. Following the addition of H$_2$O (250 mL), the solid was removed by filtration and the solvent was removed in vacuo. Remaining H$_2$O was removed by azeotroping with absolute ethanol (2×250 mL) to give 17.9 g (81.1% yield) of the product as a tan solid: $^1$H NMR (DMSO-d$_6$, 400 MHz) δ 10.22 (br s, 4 H), 8.94, (br s, 3 H), 8.81 (br s, 3 H), 3.07–3.75 (m, 7 H), 1.06–2.17 (m, 19 H); $^{13}$C NMR (DMSO-d$_6$, 100 MHz) δ 58.50, 54.95, 50.73, 50.09 br, 48.37 br, 47.16, 29.11 br, 28.87, 28.69, 28.58, 25.67 br, 22.65, 22.49, 22.37, 22.09, 14.28; HR mass spectrum (ESI) 269.2692 [M+H]$^+$ (269.2705 calcd for C$_{15}$H$_{33}$N$_4$).

D. Synthesis of Manganese(II)dichloro-(4R,9R,11R,14R,19R)-3,10,13,20,26-pentaaza-24-cyclohexyl-11-methyltetracyclo[20.3.1.0$^{4,9}$.0$^{14,19}$]hexacosa-1(25),22(26), 23-triene.

To a stirred solution of bis-cyclohexyl tetraamine tetrahydrochloride (4.29 g, 10.4 mmol) in absolute ethanol (100 mL) was added KOH (2.64 g—88%, 41.4 mmol) and the mixture was stirred at room temperature for 30 minutes under an argon atmosphere. MnCl$_2$ (1.30 g, 10.4 mmol) was then added and after stirring the suspension for an additional 30 minutes, 4-cyclohexyl-2,6-pyridinedicarboxaldehyde (2.25 g, 10.4 mmol) was added to the brown mixture which was then refluxed. After 24 hours, the reaction had gone to completion; only the bis(imine) was seen: mass spectrum (ESI) m/z (relative intensity) 539 (25) [M−Cl]$^+$, 252 (100) [M−2Cl]$^{++}$. After the addition of MeOH (50 mL), the mixture was cooled to 0° C., NaBH$_4$ (1.57 g, 41.4 mmol) was added and the mixture was stirred for 30 minutes. Additional NaBH$_4$ (1.57 g, 41.4 mmol) was then added at 0° C. and the mixture was allowed to warm to room temperature while stirring an additional 60 hours. The solvent was removed in vacuo and the residual oil was dissolved in a mixture of CH$_2$Cl$_2$ (250 mL) and H$_2$O (250 mL). The mixture was filtered to remove a small amount of brown solid, saturated NaCl (250 mL) was added and the layers were separated. The aqueous layer was extracted with CH$_2$Cl$_2$ (250 mL) and the extracts were combined. The combined extracts were washed with saturated NaCl (250 mL) and dried over MgSO$_4$. Filtration and removal of the solvent in vacuo gave 5.86 g of a brown foam. The crude product was purified by flash chromatography (silica gel, 98:2 CH$_2$Cl$_2$—MeOH) to give 1.78 g (29.7% yield) of the product as a pale yellow solid: HR mass spectrum (ESI) m/z (relative intensity) 543.2902 (100)/545.2892 (35) [M−Cl]$^+$ (543.2901/545.2871 calcd for C$_{28}$H$_{47}$N$_5$MnCl); Anal calcd for C$_{28}$H$_{47}$N$_5$MnCl$_2$: C, 58.03; H, 8.17; N, 12.08; Cl, 12.23. Found: C, 57.11; H, 8.12; N, 11.85; Cl, 11.95. HPLC (Vydac 218TP54 protein and peptide C18; 65% H$_2$O with 0.1% TFA/35% CH$_3$CN; flow=2 mL/min; 5 μL inj. vol.) T$_r$=7.58 min. (99.9% purity).

Example 6

Synthesis of Compound 1

A. Synthesis of 4-Chloro-2,6-dihydroxymethyl pyridine.

Dimethyl 4-chloro-2,6-pyridine dicarboxylate, prepared as in Example 4, (85.0 g, 370 mmol) was dissolved in MeOH (2.3 L). The solution was cooled to 0° C. To the cooled solution was added NaBH$_4$ (63.0 g, 167 mmol) in small portions. The reaction mixture stirred at 0° C. for 1 hour, then at room temperature for 2–3 hours. After about 3 hours, the mixture was allowed to reflux overnight. Acetone (425 mL) was added to the reaction mixture. The solution was heated to reflux for 1 hour, then was concentrated in vacuo. Saturated Na$_2$CO$_3$ solution (650 mL) was added to the concentrate and refluxed for 45 minutes. The flask was allowed to reach room temperature and left at room temperature for 16 h. The flask contained a white precipitate which was filtered and washed with chloroform (30 mL). The white solid was dissolved in hot THF (300 mL), dried over magnesium sulfate and filtered, then concentrated in vacuo to afford 32.1 g 4-chloro-2,6-dihydroxymethyl pyridine as a white solid. The filtrate was concentrated. The resulting white solid was heated in THF (500 mL), dried over magnesium sulfate and filtered. This process was repeated then the solid was stirred in 200 mL of CHCl$_3$ and filtered to afford an additional 23.6 g (87% overall yield) of pure 4-chloro-2,6-dihydroxymethyl pyridine as a white solid: $^1$H NMR (CD$_3$OD, 400 MHz) δ 7.62 (s, 2H), 5.02 (s, 2H), 4.83 (s, 4H). $^{13}$C NMR (CD$_3$OD, 100 MHz) δ 162.57, 145.75, 118.76, 63.74.

B. Synthesis of 4-Chloropyridine-2,6-dicarboxaldehyde.

Oxalyl chloride (126.93 g, 154 mmol) and CH$_2$Cl$_2$ (80 mL) were placed in a 1 L, 3-neck round bottomed flask. The solution was cooled to −60° C. To the cooled solution, DMSO (24 mL) in CH$_2$Cl$_2$ (80 mL) was added over a 5 minutes period via dropping funnel. After 10 minutes, 4-chloro-2,6-dihydroxymethyl pyridine (12.13 g, 69.9 mmol) in DMSO (40 mL) was added over 5 minutes, also via dropping funnel. After 20 min., triethylamine (200 mL) was added and the reaction was stirred at −60° C. for an additional 5 minutes. The reaction mixture was then allowed to reach room temperature. Water (400 mL) was added to the flask. The aqueous mixture was extracted with several portions of CH$_2$Cl$_2$ and the organic fractions were added together, dried over Na$_2$SO$_4$, filtered and concentrated. The crude product was eluted through a silica gel (Aldrich 200–400 mesh, 60 Å) column with CH$_2$Cl$_2$ to give 8.20 g (69% yield) of pure 4-chloropyridine-2,6-dicarboxaldehyde as a bright yellow solid. $^1$H NMR (300 MHz, CDCl$_3$) δ 10.12 (s), 8.11 (s). $^{13}$C NMR (CD$_3$OD, 100 MHz) δ 191.26, 154.24, 147.55, 125.53•mp=163° C.

C. Synthesis of Manganese(II)dichloro(4R,9R,14R,19R-24-chloro-3,10,13,20,26-pentaazatetracyclo-[20.3.1.0$^{4,9}$.0$^{14,19}$]hexacosa-1(26),22(23),24-triene).

N,N'-Bis{(1R,2R)-[2-(amino)]cyclohexyl}-1,2-diaminoethane tetrahydrochloride, prepared as in Example 1, (29.98 g, 72.4 mmol) was placed in a flask with EtOH (750 mL). To the stirred suspension was added KOH (18.90 g, 289.7 mmol). The KOH dissolved and finely divided KCl precipitated. After 30 minutes, MnCl$_2$ (9.18 g, 72.4 mmol) was added. The MnCl$_2$ slowly dissolved and gave a green suspension. After the MnCl₂ had dissolved, 4-chloropyridine dicarboxaldehyde, prepared as in Example 3B (12.28 g, 72.4 mmol) was added. The reaction mixture stirred at room temperature for an hour, then was heated to reflux for several days. The reaction mixture was cooled to room temperature and MeOH (350 mL) was added. The flask was cooled to 0° C. in an ice-water bath. To the reaction mixture was added NaBH₄ (5.57 g, 144.8 mmol) in small portions. The flask was allowed to reach room temperature. Water was added, and the reaction mixture was concentrated. The crude material was extracted with equal amounts (500 mL each) of CH₂Cl₂, H₂O and brine. The aqueous layer was washed with several portions of CH₂Cl₂. The organic fractions were added together, dried over Na₂SO₄, filtered and concentrated. The crude material was dissolved in CHCl₃ and purified by silica gel chromatography (Aldrich 200–400 mesh, 60 Å). The product was eluted through the column with 1% MeOH/CHCl₃, increasing to 2% MeOH/CHCl₃. Purification afforded 32.71 g (90% yield) of Manganese(II)dichloro(4R,9R,14R,19R-24-chloro-3,10,13,20,26-pentaazatetracyclo-[20.3.1.0$^{4,9}$.0$^{14,19}$]hexacosa-1(26),22(23),24-triene)]. MS (LR-ESI) m/z 481 (M−Cl)⁺, 445 (M−Cl−HCl)⁺, 223 (M−2Cl)⁺⁺. And. Cal. for $C_{21}H_{34}N_5M_nCl_3$•CH₃OH: C, 48.06; H, 6.87; N 12.74; Cl, 19.34. Found, C, 47.62; H, 6.79; N, 12.97; Cl, 19.77.

The synthesis is diagramed below:

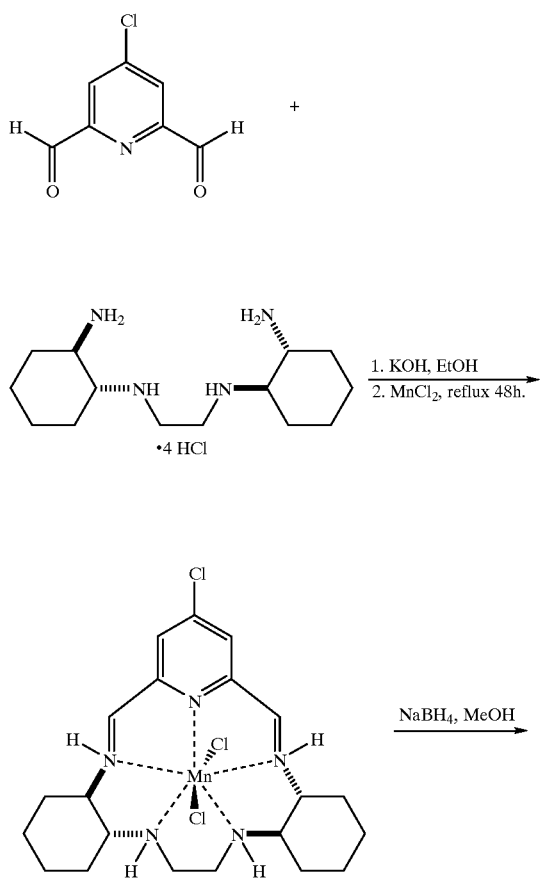

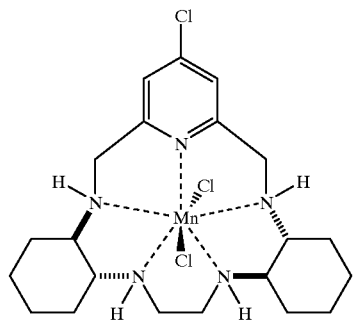

Example 7

Synthesis of Various Catalysts of the Present Invention from Compound 1 by Post-Chelation Substitution Reactions A. Synthesis of Compound 8 [Manganese(II)dichloro(4R,9R,14R,19R)-24-(2-aminoethylthio)-3,10,13,20,26-pentaazatetracyclo[20.3.1.0$^{4,9}$.0$^{14,19}$]hexacosa-1(26),22(23),24-triene)]

To a solution of 1.2% (w/v) 2-mercaptoethylamine (1 eq) in ethanol at 0° C. was added sodium ethoxide (1.1 eq) to generate the thiolate. After stirring for 1.75 h, the thiolate solution was added dropwise to a solution of 1.3% (w/v) Compound 1 (1 eq) in DMF at 0° C. The reaction mixture was allowed to stir overnight. The solvent was removed in vacuo, the product mixture was extracted with methylene chloride, and concentrated down in vacuo. Flash column chromatography using methylene chloride:methanol (9:1) as the eluent was used for purification, which was monitored via HPLC.

B. Synthesis of Compound 12 [Manganese(II)dichloro(4R,9R,14R,19R)-24-(N,N-diethyl-2-aminoethylthio)-3,10,13,20,26-pentaazatetracyclo[20.3.1.0$^{4,9}$.0$^{14,19}$]hexacosa-1(26),22(23),24-triene)].

Manganese(II)dichloro(4R,9R,14R,19R-24-chloro-3,10,13,20,26-pentaazatetracyclo-[20.3.1.0$^{4,9}$.0$^{14,19}$hexacosa-1(26),22(23),24-triene), prepared as in Example 6, (1.00 g, 1.94 mmol) was placed in a flask and dissolved in DMF (80 mL). In a separate flask, 2-diethylaminoethanethiol•HCl (364 mg, 2.14 mmol) was dissolved in DMF (20 mL). The flask was cooled to 0° C. in an ice-water bath. To the flask was added NaH (102 mg, 8.5 mmol). After stirring for 30 minutes, the 2-diethylaminoethanethiolate solution was added to the Manganese(II)dichloro(4R,9R,14R,19R-24-chloro-3,10,13,20,26-pentaazatetracyclo-[20.3.1.0$^{4,9}$.0$^{14,19}$] hexacosa-1(26),22(23),24-triene) solution via cannula. The reaction mixture was sampled after 2 hours of stirring to be analyzed by HPLC. HPLC analysis confirmed the presence of only starting material. The flask was equipped with a reflux condenser and heated to 80° C. in an oil bath overnight. The reaction mixture was cooled to room temperature and sampled for HPLC analysis. HPLC analysis confirmed the presence of only starting material. The flask was cooled to 0° C. in an ice-water bath. To a separate flask was added 2-diethylaminoethanethiol•HCl (725 mg, 4.27 mmol). The 2-diethylaminoethanethiol•HCl was dissolved in ethanol (45 mL). The flask was cooled to 0° C. in an ice-water bath. To the solution was added NaOEt (3 mL, 21 wt. %, 8.54 mmol). To the cooled manganese(II)dichloro-(4R,9R,14R,19R-24-diethylaminomercapto-3,10,13,20,26-pentaazatetracyclo[20.3.1.0$^{4,9}$.0$^{14,19}$]hexacosa-1(26),22 (23),24-triene) solution was added the 2-diethylaminoethanethiolate solution via cannula. The flask was heated to 80° C. while stirring overnight. The reaction mixture was sampled to be analyzed by HPLC. HPLC analysis confirmed the presence of product and the absence of starting material. Water (50 mL) was added to the reaction flask. The DMF, water and EtOH were removed in vacuo. The concentrate was extracted with saturated NaCl solution (250 mL), water (250 mL) and $CH_2Cl_2$ (250 mL). The water layer was washed with several portions of $CH_2Cl_2$. The organic fractions were combined, dried over $Na_2SO_4$ and concentrated in vacuo.

The crude material was purified by silica gel chromatography (Aldrich 200–400 mesh, 60 Å). The product was eluted through the column with 1% MeOH/$CH_2Cl_2$ increasing slowly to 6% MeOH/$CH_2Cl_2$. Fractions were analyzed by HPLC and combined to afford 504 mg (43% yield) of pure manganese(II)dichloro-(4R,9R,14R,19R)-24-(N,N-diethyl-2-aminoethylthio)-3,10,13,20,26-pentaazatetracyclo-[20.3.1.0$^{4,9}$.0$^{14,19}$]hexacosa-1(26),22 (23),24-triene). MS (LR-FAB) m/z 578 (M−Cl)$^+$. HRMS, Calcd. for $C_{24}H_{48}ClM_nN_6S$:578.2730. Found: 578.2764.

C. Synthesis of Compound 29 [Manganese(II)dichloro(4R, 9R,14R,19R-24-S-(2-thiopropane)-3,10,13,20,26-pentaazatetracyclo[20.3.1.0$^{4,9}$.0$^{14,19}$]hexacosa-1(26),22 (23),24-triene)].

Manganese(II)dichloro(4R,9R,14R,19R-24-chloro-3,10, 13,20,26-pentaazatetracyclo-[20.3.1.0$^{4,9}$.0$^{14,19}$]hexacosa-1 (26),22(23),24-triene) prepared as in Example 6 (1.01 g, 1.96 mmol) was placed in a flask and dissolved in DMF (60 mL). In a separate flask, 2-mercaptopropane (165 mg, 2.15mmol) was dissolved in DMF (60 mL). The flask was cooled to 0° C. in an ice-water bath. To the flask was added NaH (51 mg, 2.13 mmol). After stirring for 30 minutes, the 2-thiopropane solution was added to the Manganese(II) dichloro(4R,9R,14R,19R-24-chloro-3,10,13,20,26-pentaazatetracyclo-[20.3.1.0$^{4,9}$.0$^{14,19}$]hexacosa-1(26),22 (23),24-triene) solution via cannula. The flask was equipped with a reflux condenser and heated to 80° C. in an oil bath for 2 days. The reaction mixture was cooled to room temperature and sampled for HPLC analysis. HPLC analysis confirmed the presence of only starting material. The flask was cooled to 0° C. in an ice-water bath. To a flask containing EtOH (10 mL) was added 2-mercaptopropane (328 mg, 4.31 mmol). The flask was cooled to 0° C. in an ice-water bath. To the solution was added NaOEt (3 mL, 21 wt %, 8.62 mmol). To the cooled Manganese(II)dichloro (4R,9R,14R,19R-24-chloro-3,10,13,20,26-pentaazatetracyclo-[20.3.1.0$^{4,9}$.0$^{14,19}$]hexacosa-1(26),22 (23),24-triene) solution was added the 2-thioptopane solution via cannula. The flask was heated to 80° C. while stirring overnight. The reaction mixture was sampled to be analyzed by HPLC. HPLC analysis confirmed the presence of product and the absence of starting material. Water (50 mL) was added to the reaction flask. The DMF, water and EtOH were removed in vacuo. The concentrate was extracted with saturated NaCl solution (250 mL) and water (250 mL) then extracted with $CH_2Cl_2$ (250 mL). The aqueous layer was washed with several portions of $CH_2Cl_2$. The organic fractions were combined, dried over $Na_2SO_4$ and concentrated in vacuo. The crude material was purified by silica gel chromatography (Aldrich 200–400 mesh, 60 Å). The product was eluted through the column with 1% MeOH/$CH_2Cl_2$ increasing slowly to 2% MeOH/$CH_2Cl_2$. Fractions were analyzed by HPLC and combined to afford 504 mg (46.6% yield) of pure manganese(II)dichloro(4R,9R,14R, 19R)-24-S-(2-thiopropane)-3,10,13,20,26-pentaazatetracyclo-[20.3.1.0$^{4,9}$.0$^{14,19}$]hexacosa-1(26),22 (23),24-triene). MS (LR-FAB) m/z 578 (M−Cl)$^+$. HRMS. Calcd. for $C_{24}H_{41}N_5SM_nCl$: 521.2152. Found: 521.2136.

D. Synthesis of Compound 30 [Manganese(II)dichloro(4R, 9R,14R,19R-24-S-(2-thiobutane)-3,10,13,20,26-pentaazatetracyclo[20.3.1.0$^{4,9}$.0$^{14,19}$]hexacosa-1(26),22 (23),24-triene)].

Manganese(II)dichloro(4R,9R,14R,19R-24-chloro-3,10, 13,20,26-pentaazatetracyclo-[20.3.1.0$^{4,9}$.0$^{14,19}$]hexacosa-1 (26),22(23),24-triene), prepared as in Example 6, (1.01 g, 1.96 mmol) was placed in a flask and dissolved in DMF (80 mL). In a separate flask, 2-mercaptobutane (191 mg, 2.12 mmol) was dissolved in DMF (20 mL). The flask was cooled to 0° C. in an ice-water bath. To the flask was added NaH (51 mg, 2.13 mmol). After stirring for 30 minutes, the 2-thiobutane solution was added to the Manganese(II) dichloro(4R,9R,14R,19R-24-chloro-3,10,13,20,26-pentaazatetracyclo-[20.3.1.0$^{4,9}$.0$^{14,19}$]hexacosa-1(26),22 (23),24-triene) solution via cannula. The flask was equipped with a reflux condenser and heated to 80° C. in an oil bath overnight. The reaction mixture was cooled to room temperature and sampled for HPLC analysis. HPLC analysis confirmed the presence of only a small amount of product. The flask was cooled to 0° C. in an ice-water bath. To a flask containing EtOH (20 mL) was added 2-mercaptobutane (415 mg, 4.27 mmol). The flask was cooled to 0° C. in an ice-water bath. To the solution was added NaOEt (3 mL, 21 wt, %, 8.62 mmol). To the cooled Manganese(II)dichloro (4R,9R,14R,19R-24-chloro-3,10,13,20,26-pentaazatetracyclo-[20.3.1.0$^{4,9}$.0$^{14,19}$]hexacosa-1(26),22 (23),24-triene) solution was added the 2-mercaptobutane solution via cannula. The flask was heated to 80° C. while stirring overnight. The reaction mixture was sampled to be analyzed by HPLC. HPLC analysis confirmed the presence of product and the absence of starting material. Water (50 mL) was added to the reaction flask. The DMF, water and EtOH were removed in vacuo. The concentrate was extracted with saturated NaCl solution (250 mL), water (250 mL) and $CH_2Cl_2$ (250 mL). The aqueous layer was washed with several portions of $CH_2Cl_2$. The organic fractions were combined, dried over $Na_2SO_4$ and concentrated in vacuo. The crude material was purified by silica gel chromatography (Aldrich 200–400 mesh, 60 Å). The product was eluted through the column with 1% MeOH/$CH_2Cl_2$ increasing slowly to 2% MeOH/$CH_2Cl_2$. Fractions were analyzed by HPLC and combined to afford 680 mg (61% yield) of pure Manganese(II)dichloro(4R,9R,14R,19R)-24-(2-butanethio)-3,10,13,20,26-pentaazatetracyclo[20.3.1.0$^{4,9}$.0$^{14,19}$]hexacosa-1(26),22(23),24-triene). MS (LR-FAB) m/z 535 (M−Cl)$^+$. HRMS. Calc'd. for $C_{25}H_{43}ClM_nN_5S'$: 535.2308. Found: 535.2312.

E. Synthesis of Compound 14 [Manganese(II)dichloro(4R, 9R,14R,19R-24-S-(cyclohexylthio)-3,10,13,20,26-pentaazatetracyclo[20.3.1.0$^{4,9}$.0$^{14,19}$]hexacosa-1(26),22 (23),24-triene)].

Manganese(II)dichloro(4R,9R,14R,19R-24-chloro-3,10, 13,20,26-pentaazatetracyclo-[20.3.1.0$^{4,9}$.0$^{14,19}$]hexacosa-1 (26),22(23),24-triene), prepared as in Example 6, (1.00 g, 1.93 mmol) was placed in a flask and dissolved in DMF (80 mL). In a separate flask, cyclohexylmercaptan (247 mg, 2.12 mmol) was dissolved in DMF (20 mL). The flask was cooled to 0° C. in an ice-water bath. To the flask was added NaH (51 mg, 2.13 mmol). After stirring for 30 minutes, the cyclohexylthiolate solution was added to the Manganese(II) dichloro(4R,9R,14R,19R-24-chloro-3,10,13,20,26-pentaazatetracyclo-[20.3.1.0$^{4,9}$.0$^{14,19}$]hexaccosa-1(26),22 (23),24-triene) solution via cannula. The flask was allowed to stir at room temperature overnight. The reaction mixture was sampled for HPLC analysis. HPLC analysis confirmed the presence of only a small amount of product. The flask was cooled to 0° C. in an ice-water bath. To a flask containing EtOH (10 mL) was added cyclohexylmercaptan (475 mg, 4.25 mmol). The flask was cooled to 0° C. in an ice-water bath. To the solution was added NaOEt (3 mL, 21 WT. %, 8.62 mmol). To the cooled Manganese(II)dichloro (4R,9R,14R,19R-24-chloro-3,10,13,20,26-pentaazatetracyclo-[20.3.1.0$^{4,9}$.0$^{14,19}$]hexacosa-1(26),22 (23),24-triene) solution was added the 2-mercaptobutane solution via cannula. The flask was allowed to reach room temperature while stirring Manganese(II)dichloro(4R,9R,14R,19R-24-chloro-3,10, 13,20,26-pentaazatetracyclo-[20.3.1.0$^{4,9}$.0$^{14,19}$]hexacosa-1 (26),22(23),24-triene), prepared as in Example 6, (1.00 g, 1.93 mmol) was placed in a flask and dissolved in DMF (80 mL). In a separate flask, cyclohexylmercaptan (247 mg, 2.12 mmol) was dissolved in DMF (20 mL). The flask was cooled to 0° C. in an ice-water bath. To the flask was added NaH (51 mg, 2.13 mmol). After stirring for 30 minutes, the cyclohexylthiolate solution was added to the Manganese(II) dichloro(4R,9R,14R,19R-24-chloro-3,10,13,20,26-pentaazatetracyclo-[20.3.1.0$^{4,9}$.0$^{14,19}$]hexaccosa-1(26),22 (23),24-triene) solution via cannula. The flask was allowed to stir at room temperature overnight. The reaction mixture was sampled for HPLC analysis. HPLC analysis confirmed the presence of only a small amount of product. The flask was cooled to 0° C. in an ice-water bath. To a flask containing EtOH (10 mL) was added cyclohexylmercaptan (475 mg, 4.25 mmol). The flask was cooled to 0° C. in an ice-water bath. To the solution was added NaOEt (3 mL, 21 WT. %, 8.62 mmol). To the cooled Manganese(II)dichloro (4R,9R,14R,19R-24-chloro-3,10,13,20,26-pentaazatetracyclo-[20.3.1.0$^{4,9}$.0$^{14,19}$]hexacosa-1(26),22 (23),24-triene) solution was added the 2-mercaptobutane solution via cannula. The flask was allowed to reach room temperature while stirring overnight. The reaction mixture was sampled to be analyzed by HPLC. HPLC analysis confirmed the presence of product and the absence of starting material. Water (50 mL) was added to the reaction flask. The DMF, water and EtOH were removed in vacuo. The concentrate was diluted with $CH_2Cl_2$ (250 mL) then washed with combined saturated NaCl solution (250 mL) and water (250 mL). The aqueous layer was washed with several portions of $CH_2Cl_2$. The organic fractions were combined, dried over $Na_2SO_4$ and concentrated in vacuo. The crude material was purified by silica gel chromatography (Aldrich 200–400 mesh, 60 Å). The product was eluted through the column with 1% MeOH/$CH_2Cl_2$ increasing slowly to 2% MeOH/$CH_2Cl_2$. Fractions were analyzed by HPLC and combined to afford 675 mg (59% yield) of pure Manganese(II)dichloro(4R,9R,14R,19R)-24-(cyclohexylthio)-3,10,13,20,26-pentaazatetracyclo-[20.3.1.0$^{4,9}$.0$^{14,19}$]hexacosa-1(26),22(23),24-triene). MS (LR-ESI) m/z 561 (M–Cl)$^+$, 263 (M–2Cl)$^{++}$, 222 (M–2Cl-cyclohexene)$^{++}$. HRMS. Calc. for $C_{27}H_{45}ClM_nN_5S$•561.2465. Found: 561.2477.

F. Synthesis of Compound 31 [Manganese(II)dichloro(4R, 9R,14R,19R-24-S-(ethyl 2-thioacetate)-3,10,13,20,26-pentaazatetracyclo[20.3.1.0$^{4,9}$.0$^{14,19}$]hexacosa-1(26),22 (23),24-triene)].

Manganese(II)dichloro(4R,9R,14R,19R-24-chloro-3,10, 13,20,26-pentaazatetracyclo-[20.3.1.0$^{4,9}$.0$^{14,19}$]hexacosa-1 (26),22(23),24-triene) prepared as in Example 6 (22.26 g, 42.99 mmol) was placed in a dry, 5 L, four neck round bottomed flask equipped with a magnetic stirbar and under argon atmosphere. Anhydrous DMF (2 L) was added to the flask and the solid dissolved. The flask was placed in an ice-water bath. Sodium hydride (3.40 g, 142 mmol) was weighed into a 500 mL flask equipped with a stirbar under inert atmosphere. Anhydrous DMF (230 mL) was added to the sodium hydride and a slurry was created. The flask was cooled in a ice-water bath and ethyl thioglycolate (16.97 mL, 155 mmol) was gradually added to the slurry. After gas evolution ceased, the ice bath was removed and 120 mL of the thiolate solution was added to the solution of manganese complex. The cooling bath was removed. After 4.6 hours, an additional 100 mL of thiolate solution was added to the reaction. The reaction mixture was allowed to stir overnight. HPLC analysis indicated reaction completion. The DMF was removed in vacuo to give a residue which was dissolved in 850 mL of methylene chloride, 250 mL of water, and 250 mL of sat. NaCl. The layers were mixed and separated. The aqueous layer was extracted three times with 250 mL of methylene chloride. The methylene chloride layers were combined, dried over $Na_2SO_4$, filtered and concentrated to a crude, oily mixture, weight 40 g. The crude material was purified by silica gel chromatography using $CHCl_3$ then 1–2% EtOH in $CHCl_3$ to elute the product. Impure fractions were combined and concentrated to a solid which was triturated with ether in $CH_2Cl_2$ to give pure product which was combined with the pure fractions from the column and concentrated to yield 15.61 g (60%) of pure Manganese(II) dichloro(4R,9R,14R,19R-24-S-(ethyl 2-thioacetate)-3,10, 13,20,26-pentaazatetracyclo-[20.3.1.0$^{4,9}$.0$^{14,19}$]hexacosa-1 (26),22(23),24-triene) as a white solid. An x-ray crystal structure was obtained which confirms the structure of the product. MS ESI: m/z 565 (M–Cl)$^+$, 265 (M–Cl$_2$)$^{++}$, 251 (M–$C_2H_5$–Cl$_2$)$^{++}$, 222 (M–SCH$_2$CO$_2$C$_2$H$_5$–Cl$_2$)$^{++}$;

Anal.calcd for $C_{25}H_{41}N_5O_2SMnCl_2$ 0.5($C_2H_5OH$): C, 50.00; H, 7.10; N, 11.21; S, 5.13; Cl, 11.35. Found, C, 50.19; H, 7.14; N, 11.17; S, 5.29; Cl, 11.14.

G. Synthesis of Compound 16 [Manganese(II)dichloro(4R, 9R,14R,19R-24-S-(methyl 2-thioacetate)-3,10,13,20,26-pentaazatetracyclo[20.3.1.0$^{4,9}$.0$^{14,19}$]hexacosa-1(26),22 (23),24-triene)].

Methylthioglycolate (190 μL, 2.12 mmol) was added to a slurry of NaH (50.9 mg, 2.12 mmol) in 10 mL of anhydrous DMF which was cooled in an ice-water bath. The mixture was allowed to warm to room temperature. Manganese(II) dichloro(4R,9R,14R,19R-24-chloro-3,10,13,20,26-pentaazatetracyclo-[20.3.1.0$^{4,9}$.0$^{14,19}$]hexacosa-1(26),22 (23),24-triene), prepared as in Example 6, (1.00 g, 1.93 mmol) was added as a slurry in 10 mL of DMF to the thiolate solution. The mixture was stirred at room temperature then heated in a 80° C. oil bath for 2 hours. Additional DMF (100 mL) was added to the reaction and the reaction was stirred at room temperature for 4 days. Brine (20 mL) was added to the reaction mixture and solid precipitate was collected. The filtrate was concentrated and extracted with ether to give 962 mg of crude product. The crude product was purified by column chromatography on silica gel eluting with 1% MeOH in CHCl$_3$. Yield 627 mg (55%, 97% pure by HPLC). MS ESI: m/z 551 (M–Cl)$^+$, 258 (M–Cl$_2$)$^{++}$. HRMS. calcd. for $C_{24}H_{39}N_5O_2SM_nCl$: 551.1894. Found: 551.1886.

H. Synthesis of Compound 25 [Manganese(II)dichloro(4R, 9R,14R,19R-24-S-(3-hydroxypropanethio)-3,10,13,20, 26-pentaazatetracyclo[20.3.1.0$^{4,9}$.0$^{14,19}$]hexacosa-1(26), 22(23),24-triene)].

Sodium hydride (153 mg, 6.37 mmol) was added to a cooled solution of 3-mercapto-1-propanol (600 μL, 6.95 mmol) in DMF (150 mL). The ice bath was removed and after 10 minutes, manganese(II)dichloro(4R,9R,14R,19R-24-chloro-3,10,13,20,26-pentaazatetracyclo-[20.3.1.0$^{4,9}$.0$^{14,19}$]hexacosa-1(26),22(23),24-triene) prepared as in Example 6, (3.00 g, 5.79 mmol) was added to the suspension. The suspension turned a yellow-tan color. After stirring overnight, the reaction appeared purple-brown in color. Starting material and product were present according to HPLC and MS. An additional 200 μL of 3-mercapto-1-propanol and 51 mg of NaH in 40 mL of DMF were added to the reaction mixture followed by an additional 20 mL of DMF. After several hours another addition of thiolate was made consisting of 125 μL of 3-mercapto-1-propanol and 34 mg of NaH in DMF. The reaction was shown to be complete by HPLC. The reaction mixture was concentrated in vacuo and worked up with methylene chloride and brine. The aqueous layer was extracted several times with methylene chloride. The CH$_2$Cl$_2$ layers were combined, dried over Na$_2$SO$_4$, filtered and concentrated. The crude material was purified by column chromatography using silica gel and eluting with CH$_2$Cl$_2$ then 1–3% MeOH in CH$_2$Cl$_2$. The pure fractions were combined to yield Manganese(II)dichloro (4R,9R,14R,19R-24-S-(3-hydroxypropanethio)-3,10,13,20, 26-pentaazatetracyclo[20.3.1.0$^{4,9}$.0$^{14,19}$]hexacosa-1(26),22 (23),24-triene) as an off-white powder, weight 2.17 g (65%). HPLC indicates 99% purity. MS ESI: m/z 537 (M–Cl)$^+$, 501 (M–HCl—Cl)$^+$, 251 (M–2Cl)$^{++}$, 222 (M–2Cl–C$_3$H$_6$OH)$^{++}$. An X-ray crystal structure confirmed the structure of the product.

I. Synthesis of Compound 19 [Manganese(II)dichloro(4R, 9R,14R,19R-24-S-(N-methyl-2-thioacetamide)-3,10,13, 20,26-pentaazatetracyclo[20.3.1.0$^{4,9}$.0$^{14,19}$]hexacosa-1 (26),22(23),24-triene)].

According to the procedure for the preparation of manganese(II)dichloro(4R,9R,14R,19R-24-S-(3-hydroxypropanethio)-3,10,13,20,26-pentaazatetracyclo-[20.3.1.0$^{4,9}$.0$^{14,19}$]hexacosa-1(26),22(23),24-triene), (Example 7H), a thiolate solution was formed using N—Me mercaptoacetamide (196 μL, 2.22 mmol) and sodium hydride (51 mg, 2.12 mmol). Manganese(II)dichloro-(4R, 9R,14R,19R-24-chloro-3,10,13,20,26-pentaazatetracyclo [20.3.1.0$^{4,9}$.0$^{14,19}$]hexacosa-1(26),22(23),24-triene) prepared as in Example 6 (1.00 g, 1.93 mmol) was added to the thiolate solution. The reaction was worked up and purified to give 372 mg of Manganese(II)dichloro-(4R,9R,14R,19R-24-S-(N-methyl-2-thioacetamide)-3,10,13,20,26-pentaazatetracyclo-[20.3.1.0$^{4,9}$.0$^{14,19}$]hexacosa-1(26),22 (23),24-triene) (33%, 99% pure by HPLC) as an off-white solid. MS ESI: m/z 550 (M–Cl)$^+$, 258 (M–2Cl)$^{++}$. HRMS. calcd. for C$_{24}$H$_{40}$N$_6$OSM$_n$Cl: 550.2053. Found: 550.2062.

J. Synthesis of Compound 26 [Manganese(II)chloro(4R,9R, 14R,19R-3,10,13,20,26-pentaazatetracyclo-[20.3.1.0$^{4,}$ $_9$.0$^{14,19}$]hexacosa-1(26),22(23),24-triene-24-S-(2-thioacetic acid)].

Manganese(II)dichloro(4R,9R,14R,19R-24-S-(ethyl 2-thioacetate)-3,10,13,20,26-pentaazatetracyclo-[20.3.1.0$^{4,}$ $_9$.0$^{14,19}$]hexacosa-1(26),22(23),24-triene) prepared as in Example 7F (1.16 g, 1.93 mmol) was dissolved in THF (25 mL), sat. NaHCO$_3$ (50 mL), and water (50 mL). The mixture was stirred for several days until HPLC indicated complete ester hydrolysis. The THF was removed in vacuo, brine (50 mL) was added and the aqueous mixture was extracted with methylene chloride. The methylene chloride layer was dried over Na$_2$SO$_4$, filtered and concentrated to give the crude product. The crude material was purified by column chromatography using silica gel and eluting with 2–3% MeOH in CHCl$_3$. Yield, 820 mg of Manganese(II)chloro(4R,9R, 14R,19R-24-S-(2-thioacetate)-3,10,13,20,26-pentaazatetracyclo-[20.3.1.0$^{4,9}$.0$^{14,19}$]hexacosa-1(26),22 (23),24-triene) as an off-white solid.

Anal. calcd for C$_{23}$H$_{36}$N$_5$SO$_2$MnCl H$_2$O: C, 49.77; H, 6.90; N, 12.62; S, 5.78; Cl, 6.39. Found: C, 49.63; H, 6.91; N, 12.49; S, 5.78; Cl, 6.47.

K. Synthesis of Compound 32 [Manganese (II) dichloro [[(4R, 9R, 14R, 19R-3,10,13,20,26-pentaaztetracyclo [20.3.1.0$^{4,9}$.0$^{14,19}$]hexacosa-1(25), 22(26), 23-trien-24-ylthio)methyl]diethoxyphosphino-1-one]].

To a slurry of NaH (0.26 g, 11 mmol) in 5 mL of DMF at 0° C. was slowly added a solution of diethyl mercaptomethylphosphonate (2.2 g, 12 mmol) in 15 mL of DMF. The resulting slurry was stirred for 1 hour at room temperature and transferred via cannula to a solution of Manganese (II) dichloro(4R, 9R, 14R, 19R-24-chloro-3,10,13,20,26-pentaazatetracyclo-[20.3.1.0$^{4,9}$.0$^{14,19}$]hexacosa-1(26), 22(23), 24-triene), prepared as in Example 6, (2.84 g, 5.50 mmol) in 100 mL of DMF under nitrogen. The resulting mixture was stirred at room temperature for 48 hours. Additional thiolate, prepared as above from diethyl mercaptomethylphosphonate (0.43 g, 2.3 mmol) and NaH (53 mg, 2.2 mmol), in 4 mL of DMF was added to the reaction mixture, and the slurry heated to 60° C. for 18 hours, at which time mass spectral analysis confirmed that the starting 4-chloropyridine complex was fully consumed. The solvent was evaporated, and the residue partitioned between CH$_2$Cl$_2$ (100 mL) and brine (50 mL). The aqueous layer was separated and extracted with CH$_2$Cl$_2$ (3×50 mL). The organic layers were combined, dried over magnesium sulfate, and evaporated to a brown oil. Purification of the crude product was achieved by flash-column chromatography over 100 g of silica gel prepared in 100% ethanol. The product eluted in 100% chloroform. Fractions were analyzed by reverse-phase HPLC. Pure fractions were combined and concentrated to give a yellow oil. The oil was taken up in 5 mL of CH$_2$Cl$_2$ and crystallized by slow addition of diethyl ether (75 mL). The precipitate was isolated by filtration, washed with diethyl ether and dried in vacuo for 18 hours at room temperature to give the desired product as an off-white solid, 0.55 g (15%), m.p. >300° C.(d). FABMS m/z=664, 629 [M–Cl]$^+$.

Anal. calcd. for C$_{26}$H$_{46}$N$_5$Cl$_2$PSO$_3$Mn•1.0 H$_2$O: C, 45.68; H, 7.08; N, 10.25; S, 4.69; Cl, 10.37. Found: C, 45.69; H, 7.01; N, 10.10; S, 4.68; Cl, 10.41.

L. Synthesis of Compound 33 [Manganese (II) dichloro [[2-(4R, 9R, 14R, 19R-3,10,20,26-pentaazatetracyclo-20.3.1.0$^{4,9}$.0$^{14,15}$]hexacosa-1(25),22(26),23-trien-24-y (thio)phenyl]methan-1-ol]].

To a stirred, cooled suspension of sodium hydride (0.27 g, 6.75 mmol) under nitrogen in 15 mL of DMF at 0° C. was slowly added 2-mercaptobenzyl alcohol (1.04 g, 7.44 mmol) dissolved in 5 mL of DMF. The resulting solution was allowed to warm to room temperature and stirred for 30 minutes. It was then transferred via cannula into a stirring solution of Manganese (II) dichloro(4R, 9R, 14R, 19R-24-chloro-3,10,13,20,26-pentaazatetracyclo-[20.3.1.0$^{4,9}$.0$^{14,19}$] hexacosa-1(26), 22(23), 24-triene), prepared as in Example 6, (1.5 g, 2.89 mmol) in 80 mL of DMF under nitrogen at room temperature. During the addition a solid precipitate formed. The reaction was then stirred at 58° C. for three days at which time mass spectral analysis confirmed that the starting 4-chloropyridine complex was fully consumed. The solvent was removed in vacuo, and the resulting oil was washed with 100 mL of brine and extracted with dichloromethane (3×50 mL). The extracts were combined, dried over magnesium sulfate and filtered. Purification of the crude product was achieved by flash-column chromatography over 100 mL of silica gel eluting first with 100% dichloromethane and then with 2% methanol in dichloromethane. Fractions were analyzed by reverse-phase HPLC. Similar fractions were combined and concentrated to give an orange oil. This oil was taken up in methylene chloride/diethyl ether (60/40, v/v), decanted, and then diethyl ether was added to the solution until the product was fully precipitated. The resulting precipitate was collected by filtration and dried in vacuo at room temperature overnight affording 330 mg (18%) of the desired product as an amorphous light yellow solid (~87% pure by HPLC). FABMS m/z=620, 585 $[M-Cl]^+$; ESMS m/z=585 $[M-Cl]^+$, 275 $[M-2Cl]^{+2}$.

M. Synthesis of Compounds 34 and 35 [Manganese (II) dichloro [diethyl 4R, 9R, 14R, 19R-3,10,13,20,26-pentaazatetracyclo [20.3.1.0$^{4,9}$. 0$^{14,19}$]hexacosa-1(25),22(26),23-trien-24-phosphate] and Manganese (II) dichloro [(4R, 9R, 14R, 19R-3,10,13,20,26-pentaazatetracyclo-20.3.1.0$^{4,9}$.0$^{14,19}$]hexacosa-1(25),22(26),23-trien-24-yl) ethoxyphosphinic acid]].

To a solution of NaH (78 mg of a 60% dispersion in oil, 2.0 mmol) in DMF (4 mL) at 0° C. was added diethyl phosphite (0.27 ml of 98% purity, 2.1 mmol). The reaction mixture was allowed to warm to room temperature, and after approximately 45 min, gas evolution was no longer evident. The resultant anion was then added to a mixture of the complex of Example 6, (503 mg, 0.97 mmol) in DMF (30 mL). The reaction mixture was stirred overnight at room temperature. At this time mass spectral analysis indicated the presence of the 4-substituted diethyl phosphate ester, m/z=599 $[M-Cl]^+$, as well as the desired 4-phosphonate as the monoethyl ester product, m/z=555 $[M-Cl]^+$ and some unreacted manganese complex starting material m/z=481 ($[M-Cl]^+$ and 223 ($[M-2Cl]^{++}$.

N. Synthesis of Compound 37 [Manganese (II) dichloro [ethyl (4R, 9R, 14R, 19R-3,10,13,20,26-pentaazatetracyclo[20.3.1.0$^{4,9}$.0$^{14,19}$]hexacosa-1(25),22 (26),23-trien-24-ylthio)benzoate]].

To a stirred, cooled suspension of sodium hydride (0.32 g, 8.11 mmol) under nitrogen in 10 mL of DMF at 0° C. was slowly added ethyl 3-mercaptobenzoate (1.62 g, 8.88 mmol) dissolved in 5 mL of DMF. The resulting clear, yellow solution was allowed to warm to room temperature and stirred for 60 minutes. It was then transferred via cannula into a stirred solution of Manganese (II) dichloro(4R, 9R, 14R, 19R-24-chloro-3,10,13,20,26-pentaazatetracyclo-[20.3.1.0$^{4,9}$.0$^{14,19}$]hexacosa-1(26), 22(23), 24-triene), prepared as in Example 6, (2.0 g, 3.86 mmol) in 100 mL of DMF under nitrogen at room temperature. During the addition a solid precipitate formed. The reaction was then stirred at 58° C. for three days at which time MS confirmed that the starting complex was fully consumed. The solvent was removed in vacuo. The resulting oil was washed with 100 mL of brine and extracted with chloroform (3×50 mL). The extracts were combined, dried over magnesium sulfate and filtered. Purification of the crude product was achieved by flash-column chromatography over 200 mL of silica gel prepared in 100% ethanol. The product eluted in 100% chloroform. Fractions were analyzed by reverse-phase HPLC. Pure fractions were combined and concentrated to give an orange oil. This oil was taken up in 6 mL THF, 0.5 mL water was added, and then t-butylmethyl ether was added to the solution until the product was fully precipitated. The resulting light yellow solid was collected by filtration and dried in vacuo at room temperature overnight affording the desired pure product as a pale yellow solid, 835 mg (32%), m.p. >300° C.(d). ESMS m/z=662, 627 $[M-Cl]^+$, 296 $[M-2Cl]^{+2}$.

Anal. calcd. for $C_{30}H_{43}N_5Cl_2SO_2Mn\cdot 0.5H_2O$: C, 53.57; H, 6.59; N, 10.41; S, 4.77; Cl, 10.54. Found: C, 53.64; H, 6.62; N, 10.23; S, 4.82; Cl, 10.52.

O. Synthesis of Compound 38 [Manganese (II) dichloro[1-(4R, 9R, 14R, 19R-3,10,13,20,26-pentaazatetracyclo [20.3.1.0$^{4,9}$.0$^{14,19}$]hexacosa-1(25),22(26),23-trien-24-ylthio)]-3-methoxybenzene].

To a stirred, cooled suspension of sodium hydride (0.27 g, 6.75 mmol) under nitrogen in 10 mL of DMF at 0° C. was slowly added 3-methoxythiophenol (1.03 g, 7.34 mmol) dissolved in 5 mL of DMF. The resulting clear, colorless solution was allowed to warm to room temperature and stirred for 30 minutes. It was then transferred via cannula into a stirred solution of Manganese (II) dichloro(4R, 9R, 14R, 19R-24-chloro-3,10,13,20,26-pentaazatetracyclo-[20.3.1.0$^{4,9}$.0$^{14,19}$]hexacosa-1(26), 22(23), 24-triene), prepared as in Example 6, (1.51 g, 2.89 mmol) in 80 mL of DMF under nitrogen at room temperature. During the addition a solid precipitate formed. The reaction was then stirred at 58° C. for three days, at which time MS demonstrated the complete consumption of the starting 4-chloropyridine complex. The solvent was removed in vacuo. The resulting oil was washed with 100 mL of brine and extracted with chloroform (3×50 mL). The extracts were combined, dried over magnesium sulfate and filtered. Purification of the crude product was achieved by flash-column chromatography over 100 mL of silica gel eluting first with 100% chloroform and then with 2% methanol in chloroform. Fractions were analyzed by reverse-phase HPLC. Pure fractions were combined and concentrated to give an orange oil. This oil was taken up in chloroforn/diethyl ether (75/25, v/v), decanted, and then diethyl ether was added to the solution until the product was fully precipitated. The resulting light yellow crystals were collected by filtration and dried in vacuo at room temperature overnight affording the desired pure product as light yellow crystals, 555 mg (31%), m.p. >300° C.(d). ESMS m/z=620, 585 $[M-Cl]^+$, 275 $[M-2Cl]^{+2}$.

Anal. calcd. for $C_{28}H_{41}N_5Cl_2SOMn$: C, 54.11; H, 6.65; N, 11.27; S, 5.16; Cl, 11.41. Found: C, 54.11; H, 6.70; N, 11.15; S, 5.06; Cl, 11.47.

P. Synthesis of Compound 39 [Manganese (II) dichloro[1-(4R, 9R, 14R, 19R-3,10,13,20,26-pentaazatetracyclo [20.3.1.0$^{4,9}$.0$^{14,19}$]hexacosa-1(25),22(26),23-trien-24-ylthio)]-2-methoxybenzene].

To a stirred, cooled suspension of sodium hydride (0.27 g, 6.75 mmol) under nitrogen in 10 mL of DMF at 0° C. was slowly added 2-methoxythiophenol (1.04 g, 7.44 mmol) dissolved in 5 mL of DMF. The resulting solution was allowed to warm to room temperature and stirred for 30 minutes. It was then transferred via cannula into a stirred solution of Manganese (II) dichloro(4R, 9R, 14R, 19R-24-chloro-3,10,13,20,26-pentaazatetracyclo-[20.3.1.0$^{4,9}$.0$^{14,19}$] hexacosa-1(26), 22(23), 24-triene), prepared as in Example 6, (1.5 g, 2.89 mmol) in 80 mL of DMF under nitrogen at room temperature. During the addition a solid precipitate formed. The reaction was then stirred at 58° C. for three days, at which time MS confirmed the complete consumption of the starting complex. The solvent was removed in vacuo. The resulting oil was washed with 100 mL of brine and extracted with chloroform (3×50 mL). The extracts were combined, dried over magnesium sulfate and filtered. Purification of the crude product was achieved by flash-column chromatography over 100 mL of silica gel eluting first with 100% chloroform and then with 2% methanol in chloroform. Fractions were analyzed by reverse-phase HPLC. Pure fractions were combined and concentrated to give an orange oil. This oil was taken up in chloroform/diethyl ether (60/40, v/v), decanted, and then diethyl ether was added to the solution until the product was fully precipitated. The resulting light yellow solid was collected by filtration and dried in vacuo at room temperature overnight affording the desired pure product as an amorphous light yellow solid, 240 mg (13%), m.p. >300° C.(d). ESMS m/z=620, 585 [M−Cl]$^+$, 275 [M−2Cl]$^{+2}$.

Anal. calcd. for $C_{28}H_{41}N_5Cl_2SOMn \cdot 2H_2O$: C, 51.14; H, 6.90; N, 10.65; S, 4.88; Cl, 10.78. Found: C, 51.41; H, 6.82; N, 10.46; S, 4.88; Cl 10.62.

Q. Synthesis of Compound 36 and 35 [Manganese (II) dichloro [(4R, 9R, 14R, 19R-3,10,13,20,26-pentaazatetracyclo[20.3.1.0$^{4,9}$.0$^{14,19}$]hexacosa-1(25), 22(26), 23-trien-24-yl)diethoxyphosphino-1-one] and Manganese (II) dichloro[(4R, 9R, 14R, 19R-3,10,13,20, 26-pentaazatetracyclo[20.3.1.0$^{4,9}$.0$^{14,19}$]hexacosa-1(25), 22(26), 23-trien-24-yl) ethoxyphosphinic acid]].

To a solution of bis(acetonitrile)-dichloropalladium(II) (17 mg, 0.05 mmol) and tetraphenylphosphonium chloride (111 mg, 0.3 mmol) in DMF (5 mL) at room temperature was added triethylamine (170 μL of 99% purity, 1.2 mmol) followed by diethyl phosphite (160 μL of 98% purity, 1.2 mmol). To this mixture was added a solution of Manganese (II) dichloro(4R, 9R, 14R, 19R-24-chloro-3,10,13,20,26-pentaazatetracyclo-[20.3.1.0$^{4,9}$.0$^{14,19}$]hexacosa-1(26), 22(23), 24-triene), prepared as in Example 6, (500 mg, 1.0 mmol) in DMF (30 mL). The reaction mixture was heated to 90° C. and stirred overnight. At this time mass spectral analysis indicated the presence of the desired 4-diethyl phosphonate product, m/z=583 [M−Cl]$^+$, as well as the partially hydrolyzed product, m/z=555 [M−Cl]$^+$ along with some unreacted starting complex, MS (LRFAB) m/z=481 ([M−Cl]$^+$.

R. Synthesis of Compound 40 [Mangenese (II) dichloro [ethyl 4-(4R, 9R, 14R, 19R-3,10,13,20,26-pentaazatetracyclo [20.3.1.0$^{4,9}$.0$^{14,19}$]hexacosa-1(25),22 (26),23-trien-24-ylthio)benzoate]].

To a stirred, cooled suspension of sodium hydride (0.65 g, 16.22 mmol) under nitrogen in 15 mL of DMF at 0° C. was slowly added ethyl 4-mercaptobenzoate (3.2 g, 17.76 mmol) dissolved in 5 mL of DMF. The resulting solution was allowed to warm to room temperature and stirred for 60 minutes. It was then transferred via cannula into a stirred solution of Manganese (II) dichloro(4R, 9R, 14R, 19R-24-chloro-3,10,13,20,26-pentaazatetracyclo-[20.3.1.0$^{4,9}$.0$^{14,19}$] hexacosa-1(26), 22(23), 24-triene), prepared as in Example 6, (4.0 g, 7.72 mmol) in 80 mL of DMF under nitrogen at room temperature. During the addition a solid precipitate formed. The reaction was then stirred at 58° C. for three days at which time mass spectral analysis confirmed that the starting 4-chloropyridine complex was fully consumed. The solvent was removed in vacuo, and the resulting oil was washed with 100 mL of brine and extracted with chloroform (3×50 mL). The extracts were combined, dried over magnesium sulfate and filtered. Purification of the crude product was achieved by flash-column chromatography over 240 mL of silica gel prepared in 100% ethanol and eluting with 100% chloroform. Fractions were analyzed by reverse-phase HPLC. Similar fractions were combined and concentrated to give 1.8 g (35%) of the desired product as an orange oil (~87% pure by HPLC). FABMS m/z=662, 627 [M−Cl]$^+$.

Example 8

Synthesis of Compound 7

A. Diethyl 2,6-bis[(dimethoxy)methyl]-1,4-dihydropyridine-3,5-dicarboxylate.

To a solution of 10% ammonium acetate in water (31.0 ml, 3.10 g, 39.2 mmol) was rapidly added formaldehyde (394 mg, 13.1 mmol) and ethyl 4,4-dimethoxy-3-oxobutyrate (5.00 g, 26.3 mmol). This mixture was diluted with ethanol (30 ml) and refluxed for 16 hours. The ethanol was evaporated and the aqueous mixture was extracted with $CH_2Cl_2$ (3×100 ml). The combined extracts were dried (MgSO$^4$), filtered and concentrated to afford 3.8 g (78% yield) of the product as a yellow oil: $1_H$ NMR (300 MHz, CDCl$_3$) δ 7.41 (bs, 1H), 5.99 (s, 2 H), 4.25 (q, J=7.20 Hz, 4 H), 3.48 (s, 12 H), 3.42 (d, J=11.7 Hz, 2 H), 1.36 (t, J=7.2 Hz, 6 H). $13_C$ NMR (75 MHz, CDCl$_3$) dc 166.64 (s), 144.39 (s), 100.39 (s), 98.43 (d), 60.02 (t), 54.98 (q), 24.99 (t), 14.29 (q). MS (LR-ESI) m/z 374 [M+H]+.

B. Diethyl 2,6-bis[(dimethoxy)methyl]-3,5-pyridine dicarboxylate.

To a solution of diethyl 2,6-bis[(dimethoxy)methyl]-1 ,4-dihydropyridine-3,5-dicarboxylate (3.40 g, 9.10 mmol) in toluene (200 ml) was added activated manganese dioxide (3.96 g, 45.5 mmol) and the resulting mixture was heated to reflux for 2 hours. At this time another 3.96 g (45.5 mmol) of activated manganese dioxide was added and reflux was continued an additional 2 hours. The reaction was allowed to cool to room temperature, filtered through celite, and concentrated to afford 3.10 g (92% yield) of diethyl 2,6-bis [(dimethoxy)methyl]-3,5-pyridine dicarboxylate as a colorless oil: $1_H$ NMR (300 MHz, CDCl$_3$) δ 8.29 (s, 1 H), 5.93 (s, 2H), 4.40 (q, J=7.2 Hz, 4 H), 3.48 (s, 12 H), 1.41 (t, J=7.2 Hz, 6 H). $13_C$ NMR (75 MHz, CDCl$_3$) dc 165.68 (s), 156.25 (s), 138.52 (d), 126.59 (d), 101.26 (d), 61.50 (t), 54.08 (q), 13.75 (q). MS (LR-CI) m/z 372 [M+H]+.

C. 3,5-Bis(ethoxycarbonyl)-2,6-pyridine dicarboxaldehyde.

To a solution of diethyl 2,6-bis[(dimethoxy)methyl]-3,5-pyridine dicarboxylate (4.40 g, 11.9 mmol) in THF (80 ml) was added 2N HCl (80 ml), and the resulting mixture was heated to 50° C. for 30 minutes. At this time the reaction mixture was treated again with THF (80 ml) and 2N HCl (80 ml). After a total of 1.5 hours, TLC indicated that the reaction was complete (10/1 CHCl3/MeOH). The mixture was cooled and diluted with water (1 L). The pH was 0.94 and was therefore adjusted to 4.5 with solid $N_aHCO_3$. The mixture was extracted with EtOAc (2×300 ml) and the combined extracts were dried (MgSO$_4$), filtered and concentrated to afford 1.78 g of crude 3,5-bis(ethoxycarbonyl)-2,6-pyridine dicarboxaldehyde as a yellow oil: $1_H$ NMR (300 MHz, CDCl$_3$) δ 10.42 (s, 2 H), 8.49 (s, 1 H), 4.57 (q, J=7.2 Hz, 4 H), 1.51 (t, J=7.2 Hz, 6 H). $13_C$ NMR (75 MHz, CDCl$_3$) dc 189.83 (s), 164.67 (s), 152.17, 138.75, 130.64, 63.11 (t), 13.90 (q). MS (LR-CI) m/z 280 [M+H]+.

D. Manganese(II)dichloro(ethyl-3,10,13,20,26-pentaaza-25-(ethoxycarbonyl)tetracyclo [20.3.1.0$^{4,9}$.0$^{14,19}$] hexacosa-1(26),2,20,22(23),24-pentaene-23-carboxylate).

In a 500-mL flask N,N'-Bis{(1R,2R)-[2-(amino)] cyclohexyl}-1,2-diaminoethane tetrahydrochloride (860 mg, 2.15 mmol) was suspended in ethanol (30 mL) and treated with solid KOH (502 mg of 89%, 8.00 mmol) and the resultant mixture was stirred at 52° C. (bath temperature) for 20 minutes. At this time, $M_nCl_2$ (264 mg, 2.10 mmol) was added in one portion. After 5 minutes crude 3,5-bis(ethoxycarbonyl)-2,6-pyridine dicarboxaldehyde (930 mg of material that was estimated to be 65% pure, approximately 2.10 mmol) was added and the resulting mixture was refluxed for 16 hours thereafter. After this time, the orange-red template product Manganese(II)dichloro(ethyl-3,10,13,20,26-pentaaza-25-(ethoxycarbonyl)-tetracyclo[20.3.1.0$^{4,9}$.0$^{14,19}$]hexacosa-1(26),2,20,22(23),24-pentaene-23-carboxylate) was observed in the ethanolic reaction mixture as the only significant product: MS (LR-FAB) m/z 443 [M−Cl]+. HPLC (Vydac 218TP54 protein and peptide C18; 80% $H_2O$ with 0.1% TFA/20% Acetonitrile; flow=1 ml/min; 5 ml inj. vol.) TR=3.19 min. This mixture was taken on to the next step directly.

E. Manganese(II)dichloro(ethyl-3,10,13,20,26-pentaaza-25-(ethoxycarbonyl)tetracyclo [20.3.1.0$^{4,9}$.0$^{14,19}$]hexacosa-1 (26),22(23),24-triene-23-carboxylate)].

The ethanolic reaction mixture from step D above was treated (cautiously) under an argon atmosphere, with Pd(black) (500 mg), 10% Pd(C) (350 mg), and ammonium formate (1.6 g). The resulting mixture was heated to reflux under argon for 2 hours. HPLC (Vydac 218TP54 protein and peptide C18; 70% H2O with 0.1% TFA/30% Acetonitrile; flow=2 ml/min; 5 ml inj. vol.) at this time showed only product. The reaction mixture was cooled and filtered through a 1 inch pad of celite carefully under an argon blanket. The filtrate was concentrated purified by flash chromatography ($SiO_2$, 210:1 $CHCl_3$/methanol followed by 100:1 $CHCl_3$/methanol) to afford 450 mg of manganese(II) dichloro(ethyl 3,10,13,20,26-pentaaza-25-(ethoxycarbonyl) tetracyclo[20.3.1.0$^{4,9}$.0$^{14,19}$]hexacosa-1 (26),22(23),24-triene-23-carboxylate) as a yellow foam: MS (HR-ESI) m/z 591.2386 [M−Cl]+ (591.2384 calcd for $C_{27}H_{43}N_5O_4Cl$). HPLC (Vydac 218TP54 protein and peptide C18; 70% $H_2O$ with 0.1% TFA/30% Acetonitrile; flow=2 ml/min; 5 ml inj. vol.) TR=5.05 min (97.3% purity).

Example 9

Synthesis of Compound 42

A. Diethyl 4-cyclohexyl-2,6-bis(dimethoxymethyl)-1,4-dihydropyridine-3,5-dicarboxylate.

To aqueous ammonium acetate (310 mL–10% sol'n, 30.83 g, 400 mmol) was rapidly added cyclohexane carboxaldehyde (11.22 g, 100 mmol) and ethyl 4,4-dimethoxy-3-oxo-butyrate (38.04 g, 200 mmol). Ethanol (60 mL) was added and the reaction was heated to 80° C. in an oil bath for 16 hours. The reaction was evaporated to remove ethanol and water (200 mL) was added. The mixture was extracted with methylene chloride (3×500 mL). The organic phase was dried over $MgSO_4$, filtered, and evaporated to afford 41.1 g of diethyl 4-cyclohexyl-2,6-bis(dimethoxymethyl)-1,4-dihydropyridine-3,5-dicarboxylate as an oil. $1_H$ NMR ($CDCl_3$) δ 7.71 (s, 1H) 5.93 (s, 2H) 4.20–3.27 (m, 17H) 1.60–0.80 (m,16H); $13_C$ NMR ($CDCl_3$) δ 167.58, 143.62, 103.43, 98.75, 60.00, 54.70, 51.21, 44.57, 39.20, 28.88, 26.62, 14.32.

B. Diethyl 4-cyclohexyl-2,6-bis(dimethoxymethyl)pyridine-3,5-dicarboxylate.

To a solution of diethyl 4-cyclohexyl-2,6-bis(dimethoxymethyl)-1,4-dihydropyridine-3,5-dicarboxylate (30.7 g, 67.54 mmol) in acetone (450 mL) was added a solution of ceric ammonium nitrate (75.05 g, 135.08 mmol) in water (125 mL) fairly rapidly at room temperature. After stirring for 10 minutes, the resulting solution was concentrated to remove the acetone. Water (300 mL) was added and the mixture was extracted with $CH_2Cl_2$ (3×500 mL). The organic phase was washed with brine (600 mL), dried ($M_gSO_4$), and evaporated to afford 29.23 g of diethyl 4-cyclohexyl-2,6-bis(dimethoxymethyl)pyridine-3,5-dicarboxylate as an oil. The oil was chromatographed on silica gel using hexane/ethyl acetate mixtures to give single spot material: $1_H$ NMR ($CDCl_3$) δ 5.37 (s, 2H) 4.32 (q, J=7.2 Hz, 4H) 3.33 (s, 12H) 2.4–2.6 (m, 1H) 1.0–1.8 (m, 16H); $13_C$ NMR ($CDCl_3$) δ 167.79, 153.25, 151.44, 128.68, 104.01, 61.51, 54.41, 52.18, 44.41, 31.10, 27.19, 25.85, 14.04; MS (HR-ESI) m/z 460.2534 [M+Li]+ (460.2523 calcd for $C_{23}H_{35}NO_8Li$).

Anal. Calcd for $C_{23}H_{35}NO_8$: C, 60.91; H, 7.78; N, 3.09. Found: C, 60.34; H, 7.60; N, 3.04.

C. 8-Aza-6,10-dihydroxy-5,11-dioxatricyclo[7.3.0.0$^{3,7}$] dodeca-1(9),2,7(8)-triene-4,12-dione.

A solution of diethyl 4-cyclohexyl-2,6-bis(dimethoxymethyl)pyridine-3,5-dicarboxylate (4.8 g,10.58 mmol) in 1:4 concentrate. HCl:Acetic acid (1.5 L) was stirred for 16 hours at room temperature. The reaction was evaporated and coevaporated with water (500 mL) to afford 3.21 g of 8-Aza-6, 1 0-dihydroxy-5,11-dioxatricyclo [7.3.0.0$^{3,7}$]-dodeca-1(9),2,7(8)-triene-4,12-dione as a tan solid. $1_H$ NMR (DMSO) δ 8.8 (bs, 2H) 6.75 (m, 2H) 4.16–4.24 (m, 1H) 1.2–2.37 (m, 10H). $13_C$ NMR (DMSO) δ 172.70, 166.14, 160.27, 120.48, 96.75, 36.84, 28.87, 28.80, 28.74, 26.45, 25.41. MS, m/z (relative intensity) 306 [(M+H)+, 100]. MS (HR-ESI, negative ion) m/z 304.0830 [M−H]-(304.0821 calcd for $C_{15}H_{14}NO_6$).

D. Manganese(II)dichloro(3,10,13,20,26-pentaaza-24-cyclohexyltetracyclo [20.3.1.0$^{4,9}$.0$^{14,19}$]hexacosa-1(26), 2,20,22(23),24-pentaene-23,25-diammonium carboxylate).

To a suspension of N,N'-Bis{(1R,2R)-[2-(amino)] cyclohexyl}-1,2-diaminoethane tetrahydrochloride (4.01 g, 10.01 mmol) in ethanol (100 mL) was added potassium hydroxide (2.83 g, 50.54 mmol). The reaction was stirred for 30 minutes at room temperature and $MnCl_2$ (1.26 g, 10.01 mmol) was added. The reaction was stirred for an additional 30 minutes at room temperature. A solution of 8-aza-6,10-dihydroxy-5,11-dioxatricyclo[7.3.0.0$^{3,7}$]-dodeca-1(9),2,7(8)-triene-4,12-dione (3.21 g, 10.51 mmol) in ethanol (90 mL) was added and the reaction was refluxed for 16 hours. At this time HPLC analysis showed only template product manganese(II)dichloro(3,10,13,20,26-pentaaza-24-cyclohexyltetracyclo [20.3.1.0$^{4,9}$.0$^{14,19}$]hexacosa-1 (26),2,20,22(23),24-triene-23,25-diammonium carboxylate)]: HPLC (Vydac 218TP54 protein and peptide C18; 80% $H_2O$ with 0.1% TFA/20% Acetonitrile; flow=2 ml/min; 10 ml inj. vol.) TR=3.85 min. The reaction was cooled to room temperature taken on to the next step directly.

E. Manganese(II)dichloro(3,10,13,20,26-pentaaza-24-cyclohexyltetracyclo [20.3.1.0$^{4,9}$.0$^{14,19}$]hexacosa-1(26), 22(23),24-triene-23,25-diammonium carboxylate).

The orange-red ethanol solution from step D was diluted with water (200 mL). Palladium black (5 g) and ammonium formate (10 g) were added and the reaction was refluxed for 3 hours. The reaction was cooled to room temperature, filtered through celite, and the cake washed with water (500 mL) and ethanol (500 mL). The filtrate was evaporated to afford 10 g of Manganese(II)dichloro-(3,10,13,20,26-pentaaza-24-cyclohexyltetracyclo[20.3.1.0$^{4,9}$.0$^{14,19}$] hexacosa-1(26),22(23),24-triene-23,25-diammonium carboxylate). HPLCMS, m/z 695.4 [M−2Cl+TFA+.

F. Manganese(II)dichloro(ethyl 3,10,13,20,26-pentaaza-24-cyclohexyl-25-ethoxycarbonyl)tetracyclo[20.3.1.0$^{4,9}$.0$^{14,19}$]hexacosa-1 (26),22(23),24-triene-23-carboxylate).

To a suspension of manganese(II)dichloro-(3,10,13,20,
26-pentaaza-24-cyclohexyltetracyclo[20.3.1 .0$^{4,9}$.0$^{14,19}$]
hexacosa-1(26),22(23),24-triene-23,25-diammonium
carboxylate) (0.65 g,0.93 mmol) in DMF (15 mL) was added
ethyl iodide (1.49 g, 9.3 mmol) and the reaction was stirred
for 16 hours at room temperature. The reaction was concentrated and the residue was partitioned between brine (50
mL) and ethyl acetate (50 mL). The organic layer was dried
(MgSO$_4$), filtered, and evaporated to afford 0.7 g crude
material, which was chromatographed on silica gel using
100:1 CHCl$_3$/ethanol to pure manganese(II)dichloro(ethyl
3,10,13,20,26-pentaaza-24-cyclohexyl-25-ethoxycarbonyl)
tetracyclo-[20.3.1.0$^{4,9}$.0$^{14,19}$]hexacosa-1(26),22(23),24-
triene-23-carboxylate)]: MS (HR-ESI) m/z 673.3176
[M–Cl]$^+$ (673.3167 calcd for C$_{33}$H$_{53}$N$_5$O$_4$MnCl). A sample
was recrystallized as the hydrate from aqueous THF/methyl
t-butyl ether.

Anal. Calcd for C$_{33}$H$_{53}$N$_5$O$_4$MnCl$_2$ [H$_2$O]1.5: C, 53.80;
H, 7.66; N, 9.51; Cl, 9.62. Found: C, 53.90; H, 7.68; N, 9.30;
Cl, 9.40.

Example 10

Synthesis of Compound 15

Manganese(II)dichloro(methyl 3,10,13,20,26-pentaaza-
24-cyclohexyl-25-methoxycarbonyl)tetracyclo-[20.3.1.0$^{4,}$
$_9$.0$^{14,19}$]hexacosa-1(26),22(23),24-triene-23-carboxylate).

To a suspension of manganese(II)dichloro-(3,10,13,20,
26-pentaaza-24-cyclohexyltetracyclo[20.3.1.0$^{4,9}$.0$^{14,19}$]
hexacosa-1(26),22(23),24-triene-23,25-diammonium
carboxylate), described in Example 9, (6.62 g, 9.49 mmol)
in DMF (132 mL) was added methyl iodide (13.47 g, 94.9
mmol) and the reaction was stirred for 16 hours at room
temperature. The reaction was concentrated and the residue
was partitioned between brine (150 mL) and ethyl acetate
(150 mL). The organic layer was dried (MgSO$_4$), filtered,
and evaporated to afford 1.1 g crude material, which was
chromatographed on silica gel using 100:1 CHCl$_3$:methanol
to give pure manganese(II)dichloro(methyl 3,10,13,20,26-
pentaaza-24-cyclohexyl-25-methoxycarbonyl)tetracyclo-
[20.3.1.0$^{4,9}$.0$^{14,19}$]hexacosa-1(26), 22(23),24-triene-23-
carboxylate)]: MS (HR-ESI) m/z 645.2896 [M–Cl]$^+$
(645.2896 calcd for C$_{31}$H$_{49}$N$_5$O$_4$MnCl).

Example 11

Synthesis of Compound 17

[Manganese(II)dichloro-(4R,9R,14R,19R)-3,10,13,20,
26-pentaaza-24-piperidyltetracyclo[20.3.1.0$^{4,9}$.0$^{14,19}$]
hexacosa-1 (25),22(26),23-triene].

Manganese(II)dichloro-(4R,9R,14R,19R)-3,10,13,20,26-
pentaaza-24-bromotetracyclo[20.3.1.0$^{4,9}$.0$^{14,19}$]hexacosa-1
(26),22(23),24-triene (2.0 9, 3.56 mmol) (Compound 23)
was added to a round bottom flask (200 mL), and cesium
carbonate (1.62 g, 0.267 mmol), palladium acetate (0.060 g,
0.267 mmol), and S-2,2'-bis(diphenylphosphino)-1,1'-
binaphthyl (0.155 g, 0.249 mmol), were added, followed by
dioxane (30 mL). Piperidine (0.36 g, 4.26 mmol) was added,
the system was inerted (nitrogen), and the reaction mixture
was heated to 105° C. After stirring overnight, additional
palladium acetate (0.028 g, 0.124 mmol) and S-2,2'-bis
(diphenylphosphino)-1,1'-binaphthyl (0.080 g, 0.124 mmol)
were added. At the end of the reaction, determined by the
absence of the starting bromo complex, the reaction mixture
was cooled to room temperature, filtered, and the solvent
was removed under reduced pressure. The residue was
partitioned between water (60 mL) and dichloromethane
(150 mL). The layers were separated and the aqueous layer
was washed with dichloromethane (50 mL). The combined
dichloromethane layers were stirred with saturated sodium
chloride solution (50 mL), the organic layer was separated
and stirred again with another volume of sodium chloride
solution. After drying (magnesium sulfate) and filtration, the
solvent was removed under reduced pressure. Chromatography was performed on silica gel eluting with from 2% to
4% methanol in dichloromethane. Fractions 77 to 100 were
combined and treated with manganese dichloride in three
portions (0.053 g, 0.152 g, and 0.53 g) in dioxane over three
days at 45° C. due to evidence that free ligand was present.
After the last addition, the reaction mixture was refluxed
overnight. After cooling to room temperature and filtering,
the solvent was removed under reduced pressure. The residue was dissolved in dichloromethane (50 mL) and stirred
with saturated aqueous sodium chloride. The layers were
separated, and the solvent was removed under reduced
pressure and the residue was purified by chromatography on
silica eluting with 99/1 dichloromethane/methanol, 0.073 g,
(0.129 mmol, 3.6% yield). HRMS (electrospray)(M$^+$–Cl),
calcd. for C$_{26}$H$_{44}$O$_{35}$ClN$_6$Mn, 530.2697, found, 530.2709;
calcd. for C$_{26}$H$_{44}$O$_{37}$ClN$_6$Mn, 532.2667, found, 532.2679.

Example 12

Synthesis of Compound 41

[Manganese(II)dichloro-(4R,9R,14R,19R)-3,10,13,20,
26-pentaaza-23-benzyloxy-25-chlorotetracyclo[20.3.1.0$^{4,}$
$_9$.0$^{14,19}$]hexacosa-1(26),22(23),24-triene].

In a 2 liter four necked round bottom flask, N,N'-bis{(1R,
2R)-[2-(amino)]cyclohexyl}-1,2-
diaminoethanetetrahydrochloride (10.88 g, 27.22 mmol)
was suspended in absolute ethanol (500 mL) and stirred at
room temperature while powdered potassium hydroxide
(6.94 g, 123.65 mmol) was added. After 1 hour, manganese
dichloride (3.42 g, 27.2 mmol) was added, and the reaction
mixture was stirred for 0.5 hour at room temperature. The
3-benzyloxy-5-chloro pyridine dicarboxaldehyde (7.5 g,
27.2 mmol) was added along with ethanol (200 mL) and the
reaction mixture was stirred at reflux overnight. After cooling to room temperature, methanol (175 mL) was added. The
reaction mixture was cooled to about –5° C. and sodium
borohydride (3.30 g, 87.2 mmol) was added in small portions so as to control frothing. The reaction mixture was
allowed to slowly warm to room temperature overnight.
After removal of solvent under reduced pressure, the crude
product was partitioned between water (100 mL) and dichloromethane (300 mL). The organic layer was washed with
saturated sodium chloride (2×80 mL). The aqueous layer
was washed with dichloromethane (2×100 mL). The combined organic layers were dried over magnesium sulfate and
filtered. The solvent was removed under reduced pressure.
Chromatography on silica eluting with pure
dichloromethane, gradually changing (in 0.1% increments)
to 96% dichloromethane/4% methanol gave pure product,
6.95 g, 11.13 mmol, 41.0% yield. HRMS (electrospray)
(M$^+$–Cl) calc. for C$_{28}$H$_{40}$MnN$_5$O$^{35}$Cl$_2$, 587.1990, found
587.2000; calc. for C$_{28}$H$_{40}$MnN$_5$O$^{37}$Cl$_2$, 589.1961, found
589.1983.

Example 13

Exemplary Formulation for Topical Application

Oil in water emulsion, as percentages by weight.

| | |
|---|---|
| SOD mimic | 0.25 |
| Polyethylene glycol polyoxyethylenated with 50 moles of ethylene oxide | 1.50 |
| Diglyeryl monosterate | 1.50 |
| Liquid paraffin | 24.00 |
| Cetyl alcohol | 2.50 |
| Triethanolamine | to pH 7.0 |
| Water | Balance to 100% |

Water in oil emulsion, as percentages by weight

| | |
|---|---|
| SOD mimic | 0.25 |
| Polyglyceryl sesquiisosterate | 4.0 |
| White beeswax | 0.5 |
| Magnesium stearate | 1.5 |
| Aluminum stearate | 1.0 |
| Hydrogenated castor oil, polyoxyethyleneated (with 7 moles of ethylene oxide | 3.0 |
| Isopropyl palmitrate | 10.0 |
| Perhydrosqualene | 15.0 |
| Water | Balance to 100% |

Example 14

Use of the Sod Mimics of the Invention as Analgesics in the Rat Paw Carrageenan Model Male Sprague-Dawley rats (175–200 g, Harlan Sprague Dawley, Indianapolis, Ind., USA) were housed and cared for in accordance with the guidelines of the Institutional Animal Care and Use Committee and in accordance with NIH guidelines on laboratory animal welfare. Rats received a subplantar injection of carrageenan (0.1 ml of a 1% suspension in 0.85% saline) into the right hind paw. Paw volume was measured using plethysmometer (Ugo-Basile, Varese, Italy) immediately prior to the injection of carrageenan and thereafter at hourly intervals for up to 6 h. Edema was expressed as the increase in paw volume (ml) after carrageenan injection relative to the pre-injection value for each animal. Drugs were administered intravenously (iv) in a volume of 2.5 ml/kg, 30 min prior or at least 3 h post carrageenan injection. A hyperalgesic response to heat was determined in the same animals by Hargreaves method (Hargreaves et al., 1988). Rats were individually confined and acclimated to plexiglass chambers for 30 min. A mobile unit consisting of a high intensity projector bulb was positioned to deliver a thermal stimulus directly to an individual hind paw from beneath the chamber. The withdrawal latency period of injected and contralateral paws was determined to the nearest 0.1 sec with an electronic clock circuit and thermocouple. If the animal failed to respond by 20 sec the test was terminated. Each point will represent the change in withdrawal latency compared with control measurements taken prior to carrageenan injection.

The intraplantar injection of carrageenan in rats resulted in a time-dependent increase in paw volume and hyperalgesia that was maximal after 3–6 h. As shown in FIGS. 4–8, several SOD mimics of the present invention administered in iv 15 minutes before the injection of carrageenan inhibited edema. When the SOD mimics of the present invention were given therapeutically at the time of maximal hyperalgesia (that is, at 3 h after carrageenan) they inhibited the hyperalgesic response maximally with a very rapid onset of action (5 min onset of action), as shown in the following tables (SE=Cardiovascular Side Effect observed, ND=Not Determined):

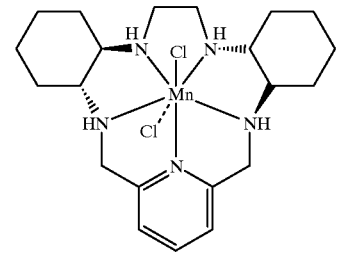

Compound A
% Inhibition of Pain

| mg/kg | 5 min. | 15 min. | 30 min. | 60 min. | 120 min. | 180 min. |
|---|---|---|---|---|---|---|
| 1 | 9 | 11 | 7 | 21 | 6 | 0 |
| 3 | 8 | 63 | 51 | 88 | 85 | 51 |
| 6 | 117 | 148 | 139 | 138 | 145 | 152 |
| 10 | SE | | | | | |

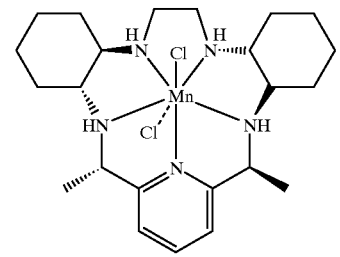

Compound B
% Inhibition of Pain

| mg/kg | 5 min. | 15 min. | 30 min. | 60 min. | 120 min. | 180 min. |
|---|---|---|---|---|---|---|
| 1 | | | | | | |
| 3 | 10 | 3 | 38 | 59 | 87 | 52 |
| 10 | 75 | 101 | 190 | 144 | 132 | 69 |
| 20 | SE | | | | | |

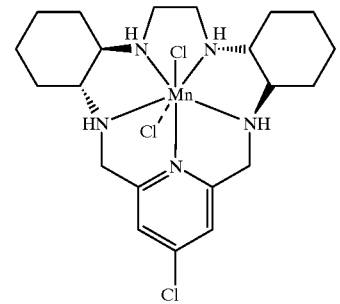

Compound 1
% Inhibition of Pain

| mg/kg | 5 min. | 15 min. | 30 min. | 60 min. | 120 min. | 180 min. |
|---|---|---|---|---|---|---|

-continued
| | | | | | |
|---|---|---|---|---|---|
| 1 | SE | 30 | 14 | 25 | 13 |
| 3 | | | | | |
| 6 | SE | 49 | 127 | 108 | 63 |
| 10 | SE | | | | |
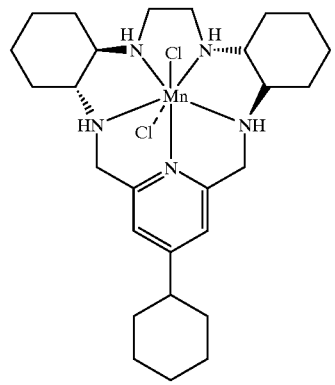
Compound 3
% Inhibition of Pain
| mg/kg | 5 min. | 15 min. | 30 min. | 60 min. | 120 min. | 180 min. |
|---|---|---|---|---|---|---|
| 1 | | 5 | 20 | 0 | 2 | 19 |
| 3 | | 74 | 49 | 21 | 53 | 0 |
| 6 | | | | | | |
| 10 | | 130 | 114 | 99 | 109 | 89 |
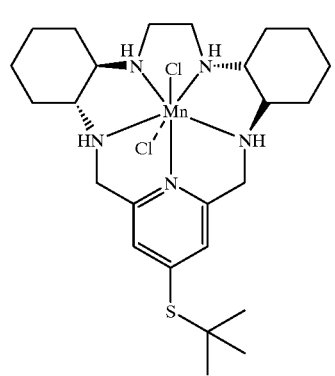
Compound 6
% Inhibition of Pain
| mg/kg | 5 min. | 15 min. | 30 min. | 60 min. | 120 min. | 180 min. |
|---|---|---|---|---|---|---|
| 1 | | 35 | 10 | 7 | 23 | 0 |
| 3 | | | | | | |
| 6 | | | | | | |
| 10 | ND | 68 | 70 | 81 | 94 | 94 |
-continued
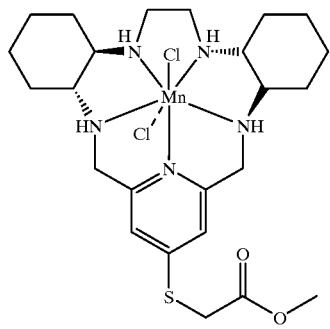
Compound 16
% Inhibition of Pain
| mg/kg | 5 min. | 15 min. | 30 min. | 60 min. | 120 min. | 180 min. |
|---|---|---|---|---|---|---|
| 1 | | 103 | 44 | 54 | 27 | 0 |
| 3 | | | | | | |
| 10 | ND | 110 | 31 | 25 | 47 | 0 |
| 20 | | 84 | 28 | 1 | 17 | 8 |
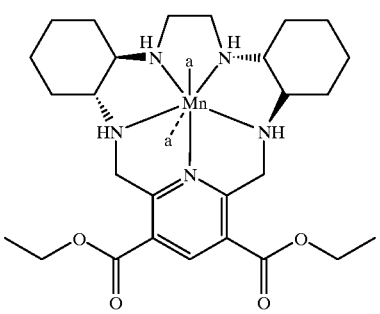
Compound 7
% Inhibition of Pain
| mg/kg | 5 min. | 15 min. | 30 min. | 60 min. | 120 min. | 180 min. |
|---|---|---|---|---|---|---|
| 1 | | | | | | |
| 3 | | 48 | 68 | 16 | 0 | 0 |
| 6 | | | | | | |
| 10 | | 84 | 89 | 108 | 74 | 80 |
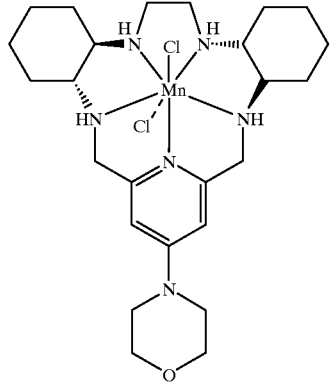
Compound 11
% Inhibition of Pain
| mg/kg | 5 min. | 15 min. | 30 min. | 60 min. | 120 min. | 180 min. |
|---|---|---|---|---|---|---|

-continued
| mg/kg | 5 min. | 15 min. | 30 min. | 60 min. | 120 min. | 180 min. |
|---|---|---|---|---|---|---|
| 1 | | | | | | |
| 3 | | | | | | |
| 6 | | | | | | |
| 10 | | 42 | 39 | 0 | 33 | 0 |
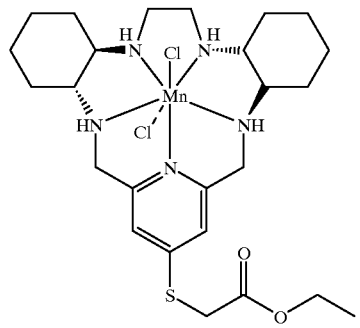
Compound 31
% Inhibition of Pain
| mg/kg | 5 min. | 15 min. | 30 min. | 60 min. | 120 min. | 180 min. |
|---|---|---|---|---|---|---|
| 1 | | 67 | 31 | 0 | 0 | 0 |
| 3 | | 85 | 63 | 8 | 0 | 0 |
| 6 | | | | | | |
| 10 | | 74 | 58 | 52 | 63 | 40 |
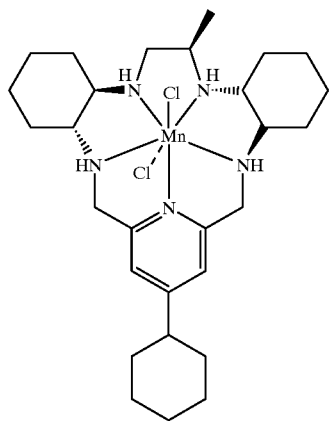
Compound 28
% Inhibition of Pain
| mg/kg | 5 min. | 15 min. | 30 min. | 60 min. | 120 min. | 180 min. |
|---|---|---|---|---|---|---|
| 1 | | 44 | 35 | 24 | 59 | 21 |
| 3 | | | | | | |
| 6 | | | | | | |
| 10 | | 53 | 64 | 84 | 99 | 73 |
-continued
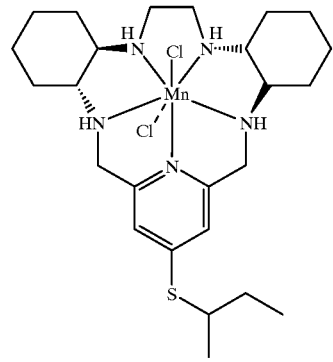
Compound 30
% Inhibition of Pain
| mg/kg | 5 min. | 15 min. | 30 min. | 60 min. | 120 min. | 180 min. |
|---|---|---|---|---|---|---|
| 1 | | 56 | 67 | 0 | 10 | 0 |
| 3 | | | | | | |
| 6 | | | | | | |
| 10 | | 78 | 104 | 89 | 143 | 102 |
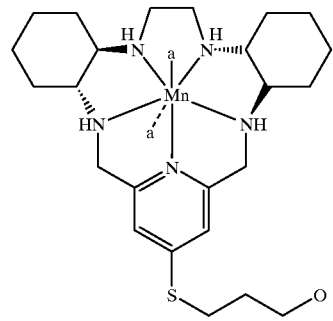
Compound 25
% Inhibition of Pain
| mg/kg | 5 min. | 15 min. | 30 min. | 60 min. | 120 min. | 180 min. |
|---|---|---|---|---|---|---|
| 1 | | 68 | 31 | 19 | 8 | 0 |
| 3 | | | | | | |
| 6 | | | | | | |
| 10 | | 77 | 7 | 23 | 42 | 8 |
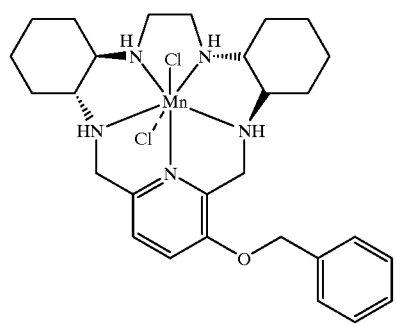
Compound 13
% Inhibition of Pain
| mg/kg | 5 min. | 15 min. | 30 min. | 60 min. | 120 min. | 180 min. |
|---|---|---|---|---|---|---|

-continued

| | | | | | | |
|---|---|---|---|---|---|---|
| 1 | | | | | | |
| 3 | 109 | 76 | 34 | 120 | 101 | |
| 6 | | | | | | |
| 10 | 86 | 93 | 93 | 80 | 110 | |

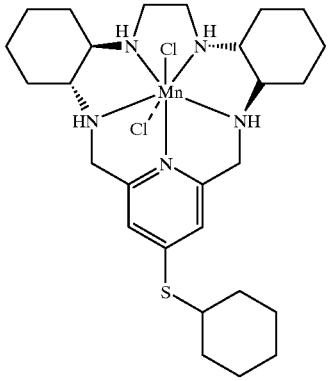

Compound 14
% Inhibition of Pain

| mg/kg | 5 min. | 15 min. | 30 min. | 60 min. | 120 min. | 180 min. |
|---|---|---|---|---|---|---|
| 1 | | | | | | |
| 3 | | | | | | |
| 6 | | | | | | |
| 10 | 93 | 103 | 93 | 110 | 141 | |

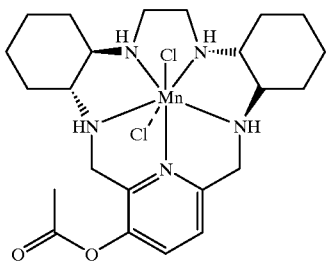

Compound 21
% Inhibition of Pain

| mg/kg | 5 min. | 15 min. | 30 min. | 60 min. | 120 min. | 180 min. |
|---|---|---|---|---|---|---|
| 1 | | | | | | |
| 3 | | | | | | |
| 6 | | | | | | |
| 10 | 117 | 47 | 46 | 57 | 11 | |

Example 15

Use of the Sod Mimics of the Invention in the Prevention of Opioid Tolerance in Mice Male CD-1 mice (Charles River, 28–35 gm) were allowed to feed ad libitum. Mice were housed 5–7 per cage in a temperature-controlled room with a 12-hr light-dark cycle. Nociceptive thresholds were measured by comparing hind paw escape latencies on a hot plate (Model 35, IITC Inc., Woodland Hills, Calif.) maintained at 57° C. Mice were placed on the heated surface enclosed by a transparent glass cylinder 25 cm high and 15 cm in diameter. Latency response was reported as the time to intermittent lifting or licking of the hind paws. A cut off latency of 20 sec was employed to prevent tissue damage in non-responsive animals. Determination of antinociception was assessed between 7:00 and 10:00 AM. Groups consisted of 7–14 mice, and each animal was used for one experimental condition. Mice were rendered tolerant by twice daily subcutaneous injections of morphine (2×10 mg/kg day) for a four day period as evidenced by a decreased antinociceptive response to a 3 mg/kg challenge dose to morphine on day 5. The latency to 3.0 mg/kg morphine in naive mice ranged from 11–13 sec. 50 min. post injection and was assigned a maximal antinociceptive score of 100%. Morphine was obtained from Mallinckrodt (St. Louis). Drugs were dissolved in saline except for the SOD mimic which was dissolved in sodium bicarbonate (26 mM, pH 8.3). Injection volumes were 0.01 mL/gm body weight.

The latency for naive mice (5.4±0.7 sec) was denoted as 0% analgesia. The latency for naive mice after 3 mg/kg morphine (10.4±0.8 sec) was denoted as 100%. See IV ADMINISTRATION and SUBCUTANEOUS ADMINISTRATION tables below. Tolerant mice exhibited latencies of 6.8±0.7 sec after 3 mg/kg morphine as measured on day 5 (time when tolerance was observed). On day 5, the SOD mimics (mg/kg) were injected 5 min (iv studies) or 40 min (sc studies) prior to morphine and antinociception was measured 50 min later. 9–20 mice were used at each dose. As can be seen in the tables here below, the SOD mimics attenuated the development of tolerance to morphine analgesia in a dose dependent manner (see table below). The SOD mimics did not elicit antinociception in naive mice indicating that, at the doses utilized, they do not behave as opioid-like analgesics.

| IV ADMIMSTRATION [SOD mimic, mg/kg] | | | | | | | | | | | |
|---|---|---|---|---|---|---|---|---|---|---|---|
| Comp. | .0001 | .0003 | .001 | .003 | .01 | .03 | .1 | .3 | 1 | 3 | 10 |
| A | | | | 0 | 10 | 40 | | | 100 | | |
| 3 | | 20 | | 56 | 70 | 88 | 94 | 134 | | | |
| 7 | | | 0 | | 42 | | 73 | | 100 | | |
| 13 | 27 | | 75 | | 73 | | 90 | | | | |
| 14 | 55 | | 71 | | 73 | | 92 | | 69 | | |
| 16 | | | | 2.5 | | 7.5 | 30 | 58 | | 102 | 165 |
| 25 | | | | 58 | | 70 | | 97 | | 95 | |

-continued

| | IV ADMIMSTRATION [SOD mimic, mg/kg] | | | | | | | | | |
|---|---|---|---|---|---|---|---|---|---|---|
| Comp. | .0001 | .0003 | .001 | .003 | .01 | .03 | .1 | .3 | 1 | 3 | 10 |
| 28 | | | 0 | | 106 | | | 94 | | 120 | |
| 31 | | | 35 | | 82 | 74 | | | | | |

| | SUBCUTANEOUS ADMINISTRATION [SOD mimic, mg/kg] | | | | | | | |
|---|---|---|---|---|---|---|---|---|
| Comp. | .05 | .1 | .3 | 1 | 3 | 5 | 10 | 30 | 100 |
| A | | | | 58 | 65 | | 94 | 102 | |
| B | | | | 92 | 100 | | 109 | | |
| 3 | 55 | | 122 | 106 | 122 | 100 | 108 | | |
| 6 | | | | | | 38 | 74 | | |
| 7 | | | 17 | 112 | 114 | | | | |
| 10 | | | | 90 | | | 73 | | |
| 16 | | | 0 | 30 | 76 | | 66 | 91 | |
| 31 | | | | 85 | | | 123 | | |

Example 16

Use of the Sod Mimics of the Invention in the Treatment of Refractory Hypotension in Endotoxemic Rats Male Sprague-Dawley rats (175–200 g, Harlan Sprague Dawley, Indianapolis, Ind., USA) were housed and cared for in accordance with the guidelines of the Institutional Animal Care and Use Committee and in accordance with NIH guidelines on laboratory animal welfare. Rats were anesthetized with inactin (100 mg/kg intraperitoneally). The trachea was cannulated to facilitate respiration and body temperature maintained at 37° C. by means of a heating pad for the entire duration of the experiment (9 hours). The left femoral vein was cannulated for the administration of drugs. After a 30 min stabilization period, lipopolysaccharide from E. coli (LPS; 4 mg/kg, serotype 0111:B4) was administered as a bolus intravenous (iv) injection at a volume of 0.3 ml and mean arterial pressure/heart rate monitored for 9 hours. Control animals received isotonic saline at the same volume and by the same route. 1, 3, or 5 hours after LPS, SOD mimic or vehicle (26 mM sodium bicarbonate buffer, pH 8.,3) was infused for a period of 6 hours.

LPS (4 mg/Kg, serotype 0111:B4) led to a profound fall in blood pressure associated with a high mortality rate (99±5% mortality at 9 hours, n=10). The administration of Compound A at 0.25 mg/kg/h prevented the development of hypotension (SEE FIG. 1) and greatly decreased mortality (20% mortality at 9 h, n=10). When Compound 25 (0.075 mg/kg/h) was administered as an iv infusion 3 hours post LPS for the duration of the experimental protocol the further development of hypotension (SEE FIG. 2) and the mortality rate were completely prevented (0% mortality at 9 h, n=10). Similar results were obtained with Compound 31 (SEE FIG. 3). Thus, improved results were obtained with less SOD mimic when the compounds of the present invention are used.

The foregoing description of the preferred embodiments of the present invention has been presented for purposes of illustration and description. They are not intended to be exhaustive or to limit the invention to the precise form disclosed, and many modifications and variations are possible in light of the above teaching. Such modifications and variations which may be apparent to a person skilled in the art are intended to be within the scope of this invention. It is also apparent to a person skilled in the art that combinations of any analgesic or anti-inflammatory agent with the SOD mimics of the present invention would be desirable, and would likely exhibit synergistic effects.

In view of the above, it will be seen that the several objects of the invention are achieved and other advantageous results attained.

We claim:

1. A catalyst for the dismutation of superoxide having the following formula:

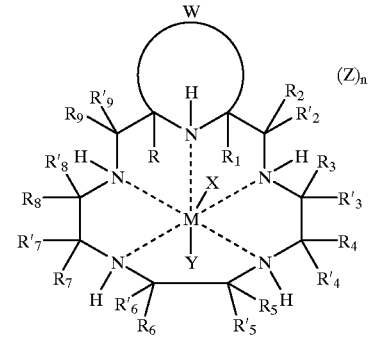

wherein a nitrogen of the macrocycle and the two adjacent carbon atoms to which it is attached independently form a substituted, unsaturated, nitrogen-containing heterocycle W having 2 to 20 carbon atoms, which may be an aromatic heterocycle, in which case the hydrogen attached to the nitrogen which is both part of the heterocycle and the macrocycle and the R groups attached to the carbon atoms which are both part of the heterocycle and the macrocycle are absent;

and wherein R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently represent hydrogen, or substituted or unsubstituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals;

and, optionally, one or more of $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 2 to 20 carbon atoms, which may be an aromatic heterocycle, in which case the hydrogen attached to the nitrogen which is both part of the heterocycle and the macrocycle and the R groups attached to the carbon atoms which are both part of the heterocycle and the macrocycle are absent;

and, optionally, one or more of $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a saturated, partially saturated, or unsaturated cyclic or heterocyclic having 3 to 20 carbon atoms;

and, optionally, one of R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula

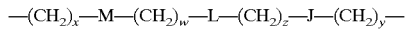

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof;

and combinations of any of the above;

wherein M is a cation of a transition metal selected from the group consisting of manganese and iron;

and wherein X, Y and Z represent suitable ligands or charge-neutralizing anions which are derived from any monodentate or polydentate coordinating ligand or ligand system or the corresponding anion thereof.

2. The catalyst of claim 1, being further described by the formula:

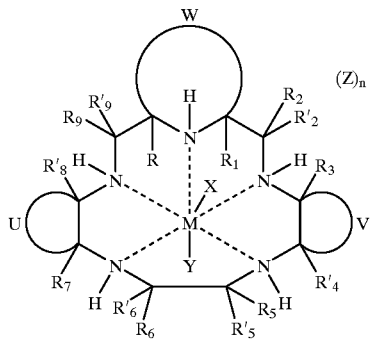

wherein U and V are saturated cyclic structures containing between 3 and 20 carbon atoms and form a cycloalkyl ring with the carbon atoms of the macrocycle to which they are attached.

3. The catalyst of claim 2, wherein U and V are saturated cyclic structures containing between 4 and 10 carbon atoms and form a cycloalkyl ring with the carbon atoms of the macrocycle to which they are attached.

4. The catalyst of claim 2, wherein U and V are trans-cyclohexanyl fused rings.

5. The catalyst of claim 2, wherein W is a substituted pyridino moiety.

6. The catalyst of claim 2, wherein U and V are trans-cyclohexanyl fused rings and W is a substituted pyridino moiety.

7. The catalyst of claim 2, wherein W is a substituted pyridino moiety with one to three substituents selected from the group consisting of cyclohexyl and benzyloxy.

8. The catalyst of claim 2, wherein W is a substituted pyridino moiety with one to three substituents selected from the group consisting of alkyl (2-thioacetic acid) esters and aryl (2-thioacetic acid) esters.

9. The catalyst of claim 2, wherein W is a substituted pyridino moiety with one to three substituents selected from the group consisting of hydroxyl alkyl thio, methoxyarylthio, and alkoxycarbonylarylthio.

10. The catalyst of claim 1, wherein the catalyst is selected from the group consisting of Compounds 1, 3, 4, 7, 10, 13, 15, 14, 16, 25, 28, 31, and 42.

11. A macrocyclic organic ligand with the following formula:

wherein a nitrogen of the macrocycle and the two adjacent carbon atoms to which it is attached independently form a substituted, unsaturated, nitrogen-containing heterocycle W having 2 to 20 carbon atoms, which may be an aromatic heterocycle, in which case the hydrogen attached to the nitrogen which is both part of the heterocycle and the macrocycle and the R groups attached to the carbon atoms which are both part of the heterocycle and the macrocycle are absent;

and wherein R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently represent hydrogen, or substituted or unsubstituted alkyl, alkenyl, alkynyl, cycloalkyl, cycloalkenyl, cycloalkylalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals;

and, optionally, one or more of $R_2$ or $R'_2$ and $R_3$ or $R'_3$, $R_4$ or $R'_4$ and $R_5$ or $R'_5$, $R_6$, or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 2 to 20 carbon atoms, which may be an aromatic heterocycle, in which case the hydrogen attached to the nitrogen which is both part of the heterocycle and the macrocycle and the R groups attached to the carbon atoms which are both part of the heterocycle and the macrocycle are absent;

and, optionally, one or more of $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a saturated, partially saturated, or unsaturated cyclic or heterocyclic having 3 to 20 carbon atoms;

and, optionally, one of R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula $$-(CH_2)_x-M-(CH_2)_w-L-(CH_2)_z-J-(CH_2)_y-$$

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza and combinations thereof;
and combinations of any of the above.

12. The ligand of claim 11, being further described by the formula:

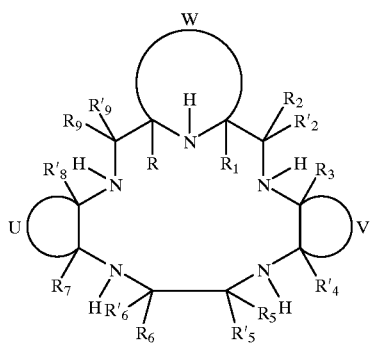

wherein U and V are saturated cyclic structures containing between 3 and 20 carbon atoms and form a cycloalkyl ring with the carbon atoms of the macrocycle to which they are attached.

13. The ligand of claim 12, wherein U and V are saturated cyclic structures containing between 4 and 10 carbon atoms and form a cycloalkyl ring with the carbon atoms of the macrocycle to which they are attached.

14. The ligand of claim 12, wherein U and V are trans-cyclohexanyl fused rings.

15. The ligand of claim 12, wherein W is a substituted pyridino moiety.

16. The ligand of claim 12, wherein U and V are trans-cyclohexanyl fused rings and W is a substituted pyridino moiety.

17. The ligand of claim 12, wherein W is a substituted pyridino moiety with at least one substituent selected from the group consisting of cyclohexyl and benzyloxy.

18. The ligand of claim 12, wherein W is a substituted pyridino moiety with at least one substituent selected from the group consisting of alkyl (2-thioacetic acid) esters and aryl (2-thioacetic acid) esters.

19. The ligand of claim 12, wherein W is a substituted pyridino moiety with at least one substituent selected from the group consisting of hydroxyl alkyl thio, methoxyarylthio, and alkoxycarbonylarylthio.

20. The ligand of claim 11, wherein the ligand is selected from the group consisting of the precursor ligands of Compounds 1, 3, 4, 7, 10, 13, 15, 14, 16, 25, 28, 31, and 42.

21. A pharmaceutical composition comprising the catalyst of claim 1 and a pharmaceutically acceptable carrier.

22. The pharmaceutical composition of claim 21 wherein the composition is formulated for topical application.

23. The pharmaceutical composition of claim 21 wherein the composition is formulated for parenteral administration.

24. A pharmaceutical composition comprising the catalyst of claim 2 and a pharmaceutically acceptable carrier.

25. The pharmaceutical composition of claim 24 wherein the composition is formulated for topical application.

26. The pharmaceutical composition of claim 24 wherein the composition is formulated for parenteral administration.

27. A method for dismutating superoxide anions comprising adding a compound of claim 1 to an aqueous environment containing superoxide anions.

28. A method of preventing or treating a disease or disorder in which superoxide anions are implicated, comprising administering to a subject in need of such prevention or treatment, a therapeutically, prophylactically, pathologically, or resuscitative effective amount of at least one compound of claim 1.

29. The method of claim 28 wherein said disease or disorder is selected from the group consisting of reperfusion injury to the ischemic myocardium, general inflammation, inflammatory bowel disease, rheumatoid arthritis, osteoarthritis, hypertension, psoriasis, organ transplant rejections, organ preservation, radiation-induced injury, platelet aggregation, stroke, autoimmune diseases, refractory hypotension, adult respiratory distress, carcinogenesis, severe chronic pain, reversal of opioid tolerance, hyperalgesia, and sepsis.

30. The method of claim 28 wherein said disease or disorder is selected from the group consisting of ischemic reperfusion injury, inflammation, hyperalgesia, sepsis, refractory hypotension, stroke, reversal of opioid tolerance, and hypertension.

31. A method of synthesizing a compound of claim 1 having the formula:

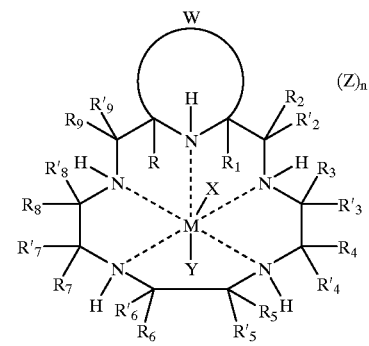

wherein W is an aromatic nitrogen containing heterocycle consisting of six atoms in the heterocyclic ring and substituted opposite the nitrogen which is a member of the macrocycle with a nucleophile, and wherein R, $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ are as defined in claim 1, while maintaining the chelated complex of the transition metal ion and the ligand, the method comprising:

a) providing a compound of the formula:
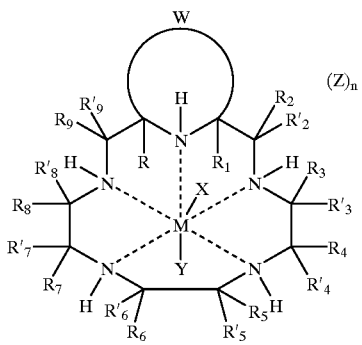
b) adding a nucleophile to the compound in a); and
c) stirring the reaction mixture until the completion of the reaction.
wherein W is a an aromatic nitrogen containing heterocycle consisting of six atoms in the heterocyclic ring and substituted opposite the nitrogen which is a member of the macrocycle with a halide;
* * * * *

UNITED STATES PATENT AND TRADEMARK OFFICE
CERTIFICATE OF CORRECTION

PATENT NO. : 6,214,817 B1
DATED : April 10, 2001
INVENTOR(S) : Riley et al.

It is certified that error appears in the above-identified patent and that said Letters Patent is hereby corrected as shown below:

Column 9, first compound after line 38: -- Compound 1 --

Column 11, first compound:      -- Compound 2 --
Column 11, second compound:   -- Compound 3 --
Column 11, third compound :     -- Compound 4 --
Column 11, fourth compound:    -- Compound 5 --

Column 13, first compound:      -- Compound 6 --
Column 13, second compound:   -- Compound 7 --
Column 13, third compound:      -- Compound 8 --
Column 13, fourth compound:    -- Compound 9 --

Column 15, first compound:      -- Compound 10 --
Column 15, second compound:   -- Compound 11 --
Column 15, third compound:      -- Compound 12 --
Column 15, fourth compound:    -- Compound 13 --

Column 17, first compound:      -- Compound 14 --
Column 17, second compound:   -- Compound 15 --
Column 17, third compound:      -- Compound 16 --

Column 19, first compound:      -- Compound 17 --
Column 19, second compound:   -- Compound 18 --
Column 19, third compound:      -- Compound 19 --
Column 19, fourth compound:    -- Compound 20 --

Column 21, first compound:      -- Compound 21 --
Column 21, second compound:   -- Compound 22 --
Column 21, third compound:      -- Compound 23 --
Column 21, fourth compound:    -- Compound 24 --

UNITED STATES PATENT AND TRADEMARK OFFICE
CERTIFICATE OF CORRECTION

PATENT NO.    : 6,214,817 B1
DATED         : April 10, 2001
INVENTOR(S)   : Riley et al.

It is certified that error appears in the above-identified patent and that said Letters Patent is hereby corrected as shown below:

Column 23, first compound:      -- Compound 25 --
Column 23, second compound:     -- Compound 26 --
Column 23, third compound :     -- Compound 28 --

Column 25, first compound:      -- Compound 29 --
Column 25, second compound:     -- Compound 30 --
Column 25, third compound:      -- Compound 31 --
Column 25, fourth compound:     -- Compound 33 --

Column 27, first compound:      -- Compound 37 --
Column 27, second compound:     -- Compound 38 --
Column 27, third compound:      -- Compound 39 --

Column 29, first compound:      -- Compound 40 --
Column 29, second compound:     -- Compound 41 --
Column 29, third compound:      -- Compound 42 --

Column 31, first compound:      -- Compound 43 --
Column 31, second compound:     -- Compound 44 --
Column 31, third compound:      -- Compound 45 --

Signed and Sealed this

First Day of April, 2003

JAMES E. ROGAN
*Director of the United States Patent and Trademark Office*